US011525825B2

(12) United States Patent
Aghvanyan et al.

(10) Patent No.: US 11,525,825 B2
(45) Date of Patent: *Dec. 13, 2022

(54) ASSAY KITS

(71) Applicant: MESO SCALE TECHNOLOGIES, LLC., Rockville, MD (US)

(72) Inventors: Anahit Aghvanyan, Gaithersburg, MD (US); Eli N. Glezer, Del Mar, CA (US); John Kenten, Boyds, MD (US); George Sigal, Rockville, MD (US); Martin Stengelin, Gaithersburg, MD (US); David Routenberg, Gaithersburg, MD (US)

(73) Assignee: MESO SCALE TECHNOLOGIES, LLC., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/564,208

(22) Filed: Sep. 9, 2019

(65) Prior Publication Data

US 2019/0391140 A1    Dec. 26, 2019

Related U.S. Application Data

(62) Division of application No. 15/311,309, filed as application No. PCT/US2015/030925 on May 15, 2015, now Pat. No. 10,408,823.

(60) Provisional application No. 62/055,093, filed on Sep. 25, 2014, provisional application No. 62/049,520, filed on Sep. 12, 2014, provisional application No.
(Continued)

(51) Int. Cl.
*C12Q 1/6832* (2018.01)
*C12Q 1/6837* (2018.01)
*C12Q 1/6844* (2018.01)
*G01N 33/543* (2006.01)

(52) U.S. Cl.
CPC ..... *G01N 33/54306* (2013.01); *C12Q 1/6832* (2013.01); *C12Q 1/6837* (2013.01); *C12Q 1/6844* (2013.01); *C12Q 2525/197* (2013.01)

(58) Field of Classification Search
CPC ............ G01N 33/54306; C12Q 1/6837; C12Q 1/6844; C12Q 2565/514; C12Q 2531/125
See application file for complete search history.

(56) References Cited

U.S. PATENT DOCUMENTS 3,996,345 A    7/1976  Ullman et al.
4,342,566 A    3/1982  Theofilopoulos et al.
(Continued)

FOREIGN PATENT DOCUMENTS

CN    1446050 A    10/2003
CN    101198707 A    6/2008
(Continued)

OTHER PUBLICATIONS

Baner J. et al., "Signal Amplification of Padlock Probes by Rolling Circle Replication", Nucleic Acids Research 26(22):5073-5078 (1998).

(Continued)

*Primary Examiner* — Joseph G. Dauner
(74) *Attorney, Agent, or Firm* — Medler Ferro Woodhouse & Mills

(57) ABSTRACT

The present invention is directed to kits for improving assay specificity and performance in binding assays.

40 Claims, 30 Drawing Sheets
(28 of 30 Drawing Sheet(s) Filed in Color)
Specification includes a Sequence Listing.

Related U.S. Application Data

62/048,489, filed on Sep. 10, 2014, provisional application No. 62/013,823, filed on Jun. 18, 2014, provisional application No. 61/993,581, filed on May 15, 2014.

(56) References Cited

U.S. PATENT DOCUMENTS

| | | |
|---|---|---|
| 4,595,661 A | 6/1986 | Cragle et al. |
| 4,988,617 A | 1/1991 | Landegren et al. |
| 5,026,653 A | 6/1991 | Lee et al. |
| 5,093,268 A | 3/1992 | Leventis et al. |
| 5,147,806 A | 9/1992 | Kamin et al. |
| 5,185,243 A | 2/1993 | Ullman et al. |
| 5,200,314 A | 4/1993 | Urdea |
| 5,238,808 A | 8/1993 | Bard et al. |
| 5,240,863 A | 8/1993 | Shibue et al. |
| 5,308,754 A | 5/1994 | Kankare et al. |
| 5,324,457 A | 6/1994 | Zhang et al. |
| 5,561,043 A | 10/1996 | Cantor et al. |
| 5,589,136 A | 12/1996 | Northrup et al. |
| 5,591,581 A | 1/1997 | Massey et al. |
| 5,597,910 A | 1/1997 | Gudibande et al. |
| 5,620,851 A | 4/1997 | Axelrod et al. |
| 5,629,156 A | 5/1997 | Shah et al. |
| 5,629,157 A | 5/1997 | Goodman et al. |
| 5,635,347 A | 6/1997 | Link et al. |
| 5,641,623 A | 6/1997 | Martin |
| 5,643,713 A | 7/1997 | Liang et al. |
| 5,652,107 A | 7/1997 | Lizardi et al. |
| 5,656,731 A | 8/1997 | Urdea |
| 5,660,991 A | 8/1997 | Lakowicz et al. |
| 5,665,539 A | 9/1997 | Sano et al. |
| 5,667,974 A | 9/1997 | Birkenmeyer et al. |
| 5,679,519 A | 10/1997 | Oprandy |
| 5,705,402 A | 1/1998 | Leland et al. |
| 5,714,320 A | 2/1998 | Kool |
| 5,731,147 A | 3/1998 | Bard et al. |
| 5,759,773 A | 6/1998 | Tyagi et al. |
| 5,776,672 A | 7/1998 | Hashimoto et al. |
| 5,786,141 A | 7/1998 | Bard et al. |
| 5,837,446 A | 11/1998 | Cozzette et al. |
| 5,846,485 A | 12/1998 | Leland |
| 5,854,033 A | 12/1998 | Lizardi |
| 5,866,434 A | 2/1999 | Massey et al. |
| 5,871,921 A | 2/1999 | Landegren et al. |
| 5,942,391 A | 8/1999 | Zhang et al. |
| 6,054,274 A | 4/2000 | Sampson et al. |
| 6,066,448 A | 5/2000 | Wohlstadter et al. |
| 6,077,668 A | 6/2000 | Kool |
| 6,136,268 A | 10/2000 | Ala-Kleme et al. |
| 6,140,135 A | 10/2000 | Landegren et al. |
| 6,143,495 A | 11/2000 | Lizardi et al. |
| 6,183,960 B1 | 2/2001 | Lizardi |
| 6,207,369 B1 | 3/2001 | Wohlstadter et al. |
| 6,210,884 B1 | 4/2001 | Lizardi |
| 6,214,552 B1 | 4/2001 | Heroux et al. |
| 6,235,472 B1 | 5/2001 | Landegren et al. |
| 6,287,824 B1 | 9/2001 | Lizardi |
| 6,291,187 B1 | 9/2001 | Kingsmore et al. |
| 6,316,229 B1 | 11/2001 | Lizardi et al. |
| 6,323,009 B1 | 11/2001 | Lasken et al. |
| 6,329,150 B1 | 12/2001 | Lizardi et al. |
| 6,344,329 B1 | 2/2002 | Lizardi |
| 6,368,801 B1 | 4/2002 | Faruqi |
| 6,511,809 B2 | 1/2003 | Baez et al. |
| 6,531,283 B1 | 3/2003 | Kingsmore et al. |
| 6,558,928 B1 | 5/2003 | Landegren |
| 6,569,647 B1 | 5/2003 | Zhang et al. |
| 6,632,609 B2 | 10/2003 | Lizardi |
| 6,646,118 B2 | 11/2003 | Kwiatkowski et al. |
| 6,673,533 B1 | 1/2004 | Wohlstadter et al. |
| RE38,442 E | 2/2004 | Zhang et al. |
| 6,709,815 B1 | 3/2004 | Dong et al. |
| 6,797,474 B2 | 9/2004 | Lizardi |
| 6,878,515 B1 | 4/2005 | Landegren |
| 6,939,720 B2 | 9/2005 | Chandler et al. |
| 6,977,722 B2 | 12/2005 | Wohlstadter et al. |
| 7,074,564 B2 | 7/2006 | Landegren |
| 7,192,703 B2 | 3/2007 | Sun et al. |
| 7,306,904 B2 | 12/2007 | Landegren et al. |
| 7,320,860 B2 | 1/2008 | Landegren et al. |
| 7,351,528 B2 | 4/2008 | Landegren |
| 7,618,776 B2 | 11/2009 | Lizardi |
| 7,790,388 B2 | 9/2010 | Landegren et al. |
| 7,842,246 B2 | 11/2010 | Wohlstadter et al. |
| 7,883,848 B2 | 2/2011 | Ericsson |
| 7,883,849 B1 | 2/2011 | Dahl |
| 7,932,060 B2 | 4/2011 | Nadeau et al. |
| 8,013,134 B2 | 9/2011 | Fredriksson et al. |
| 8,053,188 B2 | 11/2011 | Gullberg et al. |
| 8,080,393 B2 | 12/2011 | Koch et al. |
| 8,163,499 B2 | 4/2012 | Singh et al. |
| 8,222,047 B2 | 7/2012 | Duffy et al. |
| 8,236,574 B2 | 8/2012 | Duffy et al. |
| 8,268,554 B2 | 9/2012 | Schallmeiner |
| 8,338,776 B2 | 12/2012 | Walt et al. |
| 8,741,559 B2 | 6/2014 | Treiber et al. |
| 9,618,510 B2 | 4/2017 | Aghvanyan et al. |
| 9,777,338 B2 | 10/2017 | Glezer et al. |
| 10,114,015 B2 | 10/2018 | Glezer et al. |
| 11,242,570 B2 | 2/2022 | Glezer |
| 2002/0035247 A1 | 3/2002 | Kwiatkowski et al. |
| 2002/0051986 A1 | 5/2002 | Baez et al. |
| 2002/0064779 A1 | 5/2002 | Landegren et al. |
| 2002/0102592 A1 | 8/2002 | Landegren |
| 2002/0155490 A1 | 10/2002 | Skinner et al. |
| 2004/0023271 A1 | 2/2004 | Kurn et al. |
| 2004/0121382 A1 | 6/2004 | Liu et al. |
| 2004/0142323 A1 | 7/2004 | Boyde |
| 2004/0209261 A1 | 10/2004 | Keys et al. |
| 2004/0248103 A1 | 12/2004 | Feaver et al. |
| 2004/0265897 A1 | 12/2004 | Lizardi |
| 2005/0003432 A1 | 1/2005 | Hall et al. |
| 2005/0009050 A1* | 1/2005 | Nadeau ............... C12Q 1/6804 435/6.18 |
| 2005/0014140 A1 | 1/2005 | Erikson et al. |
| 2005/0282158 A1 | 12/2005 | Landegren |
| 2005/0287526 A1 | 12/2005 | Landegren et al. |
| 2007/0161029 A1* | 7/2007 | Li ....................... C12Q 1/6834 435/6.12 |
| 2007/0178934 A1 | 8/2007 | Sun |
| 2007/0259381 A1 | 11/2007 | Rissin et al. |
| 2007/0259385 A1 | 11/2007 | Rissin et al. |
| 2007/0259448 A1 | 11/2007 | Rissin et al. |
| 2009/0176318 A1 | 7/2009 | Kolpashchikov |
| 2010/0075862 A1 | 3/2010 | Duffy et al. |
| 2010/0129819 A1 | 5/2010 | Hu et al. |
| 2010/0261292 A1 | 10/2010 | Glezer et al. |
| 2011/0177054 A1 | 7/2011 | Gibbings et al. |
| 2011/0212537 A1 | 9/2011 | Rissin et al. |
| 2012/0196774 A1 | 8/2012 | Fournier et al. |
| 2012/0252692 A1 | 10/2012 | Kutyavin |
| 2012/0289428 A1 | 11/2012 | Duffy et al. |
| 2013/0059741 A1 | 3/2013 | Weiner |
| 2013/0323756 A1 | 12/2013 | Tullis et al. |
| 2014/0194311 A1 | 7/2014 | Gullberg et al. |
| 2014/0272939 A1 | 9/2014 | Aghvanyan et al. |
| 2014/0274775 A1 | 9/2014 | Glezer et al. |
| 2014/0315189 A1 | 10/2014 | Glezer et al. |
| 2015/0044674 A1 | 2/2015 | Fredriksson et al. |
| 2017/0089892 A1 | 3/2017 | Aghvanyan et al. |
| 2017/0168047 A1 | 6/2017 | Aghvanyan et al. |
| 2017/0362668 A1 | 12/2017 | Glezer et al. |
| 2019/0011441 A1 | 1/2019 | Glezer et al. |
| 2022/0033918 A1 | 2/2022 | Glezer |

FOREIGN PATENT DOCUMENTS

| | | |
|---|---|---|
| CN | 101988920 A | 3/2011 |
| CN | 102317779 A | 1/2012 |
| CN | 103703145 A | 4/2014 |
| CN | 104114718 A | 10/2014 |
| EP | 1 985 714 A1 | 10/2008 |

(56) References Cited

FOREIGN PATENT DOCUMENTS

| | | |
|---|---|---|
| EP | 2 500 435 A1 | 9/2012 |
| JP | H04-262799 A | 9/1992 |
| JP | H08-505050 A | 6/1996 |
| JP | 11-508040 | 7/1999 |
| JP | 2005-521409 A | 7/2005 |
| JP | 2006-511807 A | 4/2006 |
| JP | 2007-525661 A | 9/2007 |
| JP | 2009/106220 A | 5/2009 |
| JP | 2009-222712 A | 10/2009 |
| WO | 90/05910 A1 | 5/1990 |
| WO | 91/17442 A1 | 11/1991 |
| WO | 94/14961 A1 | 7/1994 |
| WO | 95/35390 A1 | 12/1995 |
| WO | 97/36931 A1 | 10/1997 |
| WO | 98/12539 A1 | 3/1998 |
| WO | 98/57154 A1 | 12/1998 |
| WO | 99/14599 A1 | 3/1999 |
| WO | 99/32662 A1 | 7/1999 |
| WO | 99/49079 A1 | 9/1999 |
| WO | 99/58962 A1 | 11/1999 |
| WO | 99/63347 A2 | 12/1999 |
| WO | 00/03233 A1 | 1/2000 |
| WO | 00/04193 A1 | 1/2000 |
| WO | 01/35100 A2 | 5/2001 |
| WO | 01/84146 A2 | 11/2001 |
| WO | 03/033722 A2 | 4/2003 |
| WO | 2004/061131 A1 | 7/2004 |
| WO | 2004/094456 A2 | 11/2004 |
| WO | 2005/059509 A2 | 6/2005 |
| WO | 2009/029073 A1 | 3/2009 |
| WO | 2009/067009 A1 | 5/2009 |
| WO | 2009/092386 A2 | 7/2009 |
| WO | 2010/059820 A1 | 5/2010 |
| WO | 2011/047087 A2 | 4/2011 |
| WO | 2011/143583 A1 | 11/2011 |
| WO | 2012/007511 A1 | 2/2012 |
| WO | 2012/049316 A1 | 4/2012 |
| WO | 2012/104261 A1 | 8/2012 |
| WO | 2012/152942 A1 | 11/2012 |
| WO | 2012/160083 A1 | 11/2012 |
| WO | 2013/113699 A2 | 8/2013 |
| WO | 2014/031984 A1 | 2/2014 |
| WO | 2014/160192 A1 | 10/2014 |
| WO | 2014/165061 A1 | 10/2014 |
| WO | 2015/175856 A1 | 11/2015 |

OTHER PUBLICATIONS

Darmanis S. et al., "Sensitive Plasma Protein Analysis by Microparticle-based Proximity Ligation Assays", Molecular & Cellular Proteomics 9:327-335 (2010).

Dean F.B. et al., "Rapid Amplification of Plasmid and Phage DNA Using Phi29 DNA Polymerase and Multiply-Primed Rolling Circle Amplification", Genome Research 11:1095-1099 (2001).

Faruqi F A. et al., "High-Throughput Genotyping of Single Nucleotide Polymorphisms With Rolling Circle Amplification", BMC Genomics, vol. 2(4) (Aug. 2001).

Lizardi P.M. et al., "Mutation Detection and Single-Molecule Counting Using Isothermal Rolling-Circle Amplification", Nature Genetics 19:225-232 (Jul. 1998).

Nallur G. et al., "Signal Amplification by Rolling Circle Amplification on DNA Microarrays", Nucleic Acids Research 29(23):e118 (2001).

Nong R Y. et al., "Solid-Phase Proximity Ligation Assays for Individual or Parallel Protein Analyses With Readout Via Real-Time PCR or Sequencing", Nature Protocols 8(6):1234-1248 (May 2013).

Schweitzer B. et al., "Multiplexed Protein Profiling on Microarrays by Rolling-Circle Amplification", Nature Biotechnology 20:359-365 (Apr. 2002).

Schweitzer B. et al., "Immunoassays With Rolling Circle DNA Amplification: A Versatile Platform for Ultrasensitive Antigen Detection", PNAS 97(18):10113-10119 (Aug. 29, 2000).

Söderbergo et al., "Characterizing Proteins and Their Interactions in Cells and Tissues Using the in situ Proximity Ligation Assay", Methods 45:227-232 (2008).

International Search Report dated Aug. 27, 2015 received in International Application No. PCT/US2015/030925.

Extended Supplementary European Search Report dated Sep. 13, 2017 received in European Patent Application No. 15 79 3097.5.

European Communication dated Jul. 10, 2018 received in European Patent Application No. 15 793 097.5.

European Communication dated Jun. 6, 2019 received in European Patent Application No. 15 793 097.5.

English-language translation of Chinese Office Action dated Jan. 22, 2018 received in Chinese Patent Application No. 201580037961.2.

Japanese Notice of Reasons for Rejection dated Apr. 2, 2019 received in Japanese Patent Application No. 2016-567814, together with an English-language translation.

Final U.S. Office Action dated Oct. 26, 2018 received in U.S. Appl. No. 15/311,309.

Non-Final U.S. Office Action dated May 4, 2018 received in U.S. Appl. No. 15/311,309.

Final Office Action in U.S. Appl. No. 15/440,191, dated May 22, 2020.

Andras et al., "Strategies for Signal Amplification in Nucleic Acid Detection," Mol Biotechnol 19: 29-44 (2001).

Baner et al., "Signal Amplification of Padlock Probes by Rolling Circle Replication," Nucleic Acid Res 26(22): 5073-5078 (1998).

Dahl et al., "Circle-to-Circle Amplification for Precise and Sensitive DNA Analysis," PNAS 101(13): 4548-4553 (2004).

Darmanis et al., "Self-Assembly of Proximity Probes for Flexible and Modular Proximity Ligation Assays," Biotechniques 46(4): 443-450 (2007).

Duolink II Probemaker PLUS, Duolink II Probemaker MINUS, Product Insert Doc No. 0564, OLINK Bioscience, cited in U.S. Appl. No. 14/208,040, filed May 8, 2014.

Ericsson et al., "A Dual-Tag Microarray Platform for High-Performance Nucleic Acid and Protein Analyses," Nucleic Acid Res. 36(8): e45 (2008).

Fire et al., "Rolling Replication of Short DNA Circles," PNAS 92: 4641-4645 (1995).

Fredriksson et al., "Protein Detection Using Proximity-Dependent DNA Ligation Assays," Nature Biotech. 20: 473-477 (2002).

Fredriksson et al., "Multiplexed Protein Detection by Proximity Ligation for Cancer Biomarker Validation," Nat Methods 4(4): 327-329 (2007).

Fredriksson et al. Supplementary Table 2 in "Multiplexed Protein Detection by Proximity Ligation for Cancer Biomarker Validation," Nat Methods 4(4): 327-329 (2007).

Gajadhar et al., "A proximity Ligation Assay Using Transiently Transfected, Epitope-Tagged Proteins: Application for In Situ Detection of Dimerized Receptor Tyrosine Kinases," Biotechniques 48(2): 145-151 (2010).

Gill et al., "Nucleic Acid Isothermal Amplification Technologies—A Review," Nucleosides, Nucleotides & Nucleic Acids, 27(3): 224-243 (2008).

Griffiths et al., "Miniaturising the Laboratory in Emulsion Droplets," Trends in Biotechn. 24(9): 395-402 (2006).

Gullberg et al., "A Sense of Closeness: Protein Detection by Proximity Ligation," Curr Opin Biotechnol 14: 82-86 (2003).

Gustafsdottir et al., "Detection of Individual Microbial Pathogens by Proximity Ligation," Clin Chem 52(6): 1152-1160 (2006).

Hochman et al., "An Active Antibody Fragment (Fv) Composed of the Variable Portions of Heavy and Light Chains," Biochemistry 12(6): 1130-1135 (1973).

Holder et al., "Assignment of Neisseria Meningitidis Serogroup A and C Class-Specific Anticapsular Antibody Concentrations to the New Standard Reference Serum CDC1992," Clinical and Diagnostic Laboratory Immunology 2(2):132-137 (1995).

Jeong et al., "Isothermal DNA Amplification In Vitro: The Helicase-Dependent Amplification System," Cell Mol Life Sci 66: 3325-3336 (2009).

Landegren et al., "A Ligase-Mediated Gene Detection Technique," Science 241: 1077-1080 (1988).

(56) References Cited

OTHER PUBLICATIONS

Leuchowius et al., "Parallel Visualization of Multiple Protein Complexes in Individual Cells in Tumor Tissue," Mol Cell Proteomics 12: 1563-1571 (2013).

Marchese et al., "Optimization and Validation of a Multiplex, Electrochemiluminescence-Based Detection Assay for the Quantitation of Immunoglobulin G Serotype-Specific Antipneumococcal Antibodies in Human Serum," Clinical and Vaccine Immunology 16(3):387-396 (2009).

Mendoza et al., "High-Throughput Microarray-Based Enzyme-Linked Immunosorbent Assay (ELISA)", BioTechniques 27(4)778-788 (1999).

Meso Scale Discovery Inc: "Sandwich Immunogenicity Assays for Protein Drugs," Meso Scale Discovery, Inc. Rockville, Maryland, USA (1 page) (Nov. 1, 2012).

Nilsson et al., "Padlock Probes: Circularizing Oligonucleotides for Localized DNA Detection," Science 265: 2085-2088 (1994).

Nolan et al., "Multiplexed and Microparticle-Based Analyses: Quantitative Tools for the Large-Scale Analysis of Biological Systems", Cytometry Part A 69A:318-325 (2006).

Nordengrahn et al., "Evaluation of a Novel Proximity Ligation Assay for the Sensitive and Rapid Detection of Food-and-Mouth Disease Virus," Vet Microbiol 127: 227-236 (2008).

Porter et al., "Subunits of Immunoglobulins and Their Relationship to Antibody Specificity," J Cell Physiol 67(Sup 1): 51-64 (1966).

Samiotaki et al., "Dual-Color Detection of DNA Sequence Variants by Ligase-Mediated Analysis," Genomics 20: 238-242 (1994).

Schallmeiner et al., "Sensitive Protein Detection Via Triple-Binder Proximity Ligation Assay," Nat Methods 4(2): 135-137 (2007).

Spits et al., "Whole-Genome Multiple Displacement Amplification from Single Cells," Nat Protocols 1(4): 1965-1970 (2006).

Vincent et al., "Helicase-Dependent Isothermal DNA Amplification," European Molecular Biology Organization 5(8): 795-800 (2004).

Vuoriluoto et al., "Spatio-Temporal Composition of the Mitotic Chromosomal Passenger Complex Detected Using In Situ Proximity Ligation Assay," Mol Oncol 5: 105-111 (2011).

Weibrecht et al., "Proximity Ligation Assays: A Recent Addition to the Proteomics Toolbox," Expert Rev Proteomics 7(3): 401-409 (2010).

Yamada et al., "Detection of Methicillin-Resistant *Staphylococcus aureus* Using a Specific Anti-PBP2a Chicken IgY Antibody," Japan J Infect Dis 66: 103-108 (2013).

Zhang et al., "Amplification of Circularizable Probes for the Detection of Target Nucleic Acids and Proteins," Clinica Chimica Acta 363: 61-70 (2006).

Zhou et al., "Two-Color, Rolling-Circle Amplification on Antibody Microarrays for Sensitive, Multiplexed Serum-Protein Measurements," Genome Biol 5:R28 (2004).

Non-final Office Action in U.S. Appl. No. 14/206,284, dated Oct. 16, 2015.

Final Office Action in U.S. Appl. No. 14/206,284, dated Jul. 6, 2016.

Non-final Office Action in U.S. Appl. No. 14/208,040, dated Dec. 30, 2015.

Final Office Action in U.S. Appl. No. 14/208,040, dated Oct. 11, 2016.

Non-final Office Action in U.S. Appl. No. 14/208,040, dated Feb. 7, 2017.

Final Office Action in U.S. Appl. No. 14/208,040, dated Jul. 27, 2017.

Non-final Office Action in U.S. Appl. No. 14/208,040, dated Jan. 16, 2018.

Non-final Office Action in U.S. Appl. No. 15/440,191, dated Jun. 20, 2019.

Final Office Action in U.S. Appl. No. 15/440,191, dated Dec. 16, 2019.

International Search Report issued in PCT/US14/26010, dated Jul. 7, 2014.

International Search Report issued in PCT/US14/24279, dated Jul. 17, 2014.

Darmanis et al., "ProteinSeq: High-Performance Proteomic Analyses by Proximity Ligation and Next Generation Sequencing," PLOS One 6(9) p.e25583 (2011).

Heyduk et al., "Molecular Pincers: Antibody-Based Homogeneous Protein Sensors," Analytical Chemistry 80(13):5152-5159 (2008).

Hu et al., "Quantitation of Femtomolar Protein Levels Via Direct Readout With the Electrochemical Proximity Assay," Journal of the American Chemical Society 134(16):7066-7072 (2012).

Tavoosidana et al. "Multiple Recognition Assay Reveals Prostasomes as Promising Plasma Biomarkers for Prostate Cancer," PNAS 108(21):8809-8814 (2011).

International Search Report issued in PCT/US2012/064263, dated Mar. 15, 2013.

Chan, "General principle of immunoassay." *Immunoassay: a practical guide* pp. 1-23 (1987).

Restriction Requirement in U.S. Appl. No. 16/136,498, dated Mar. 19, 2021.

Restriction Requirement in U.S. Appl. No. 14/357,653, dated Jul. 31, 2015.

Non-Final Office Action in U.S. Appl. No. 14/357,653, dated Oct. 26, 2015.

Final Office Action in U.S. Appl. No. 14/357,653, dated Jun. 22, 2016.

Non-Final Office Action in U.S. Appl. No. 14/357,653, dated Jan. 31, 2017.

Non-Final Office Action in U.S. Appl. No. 15/696,953, dated Mar. 27, 2019.

Final Office Action in U.S. Appl. No. 15/696,953, dated Nov. 25, 2019.

Final Office Action in U.S. Appl. No. 15/696,953, dated Jun. 15, 2020.

Non-Final Office Action in U.S. Appl. No. 15/696,953, dated Mar. 9, 2021.

Adler et al., "Detection of rViscumin in plasma samples by immuno-PCR," Biochemical and Biophysical Research Communications 300:757-763 (2003).

He, "Development of on-chip proximity ligation assay with in situ single molecule sequencing readout," Masters Dissertation, Uppsala University (2011).

Niemeyer et al., "Fluorometric Polymerase Chain Reaction (PCR) Enzyme-Linked Immunosorbent Assay for Quantification of Immuno-PCR Products in Microplates," Analytical Biochemistry 246:140-145 (1997).

Soderberg et al., "Direct observation of individual endogenous protein complexes in situ by proximity ligation," Nature Methods 3(12):995-1000 (2006).

Non-final Office Action issued in U.S. Appl. No. 16/136,498, dated Oct. 13, 2021.

Notice of Allowance issued in U.S. Appl. No. 15/696,953, dated Sep. 27, 2021.

Final Office Action issued in U.S. Appl. No. 16/136,498, dated Apr. 20, 2022.

Advisory Action issued in U.S. Appl. No. 16/136,498, dated Jul. 5, 2022.

Lee et al., "Diffractometric Detection of Proteins using Microbead-based Rolling Circle Amplification," Analytical Chemistry 82(1):197 (2010).

\* cited by examiner

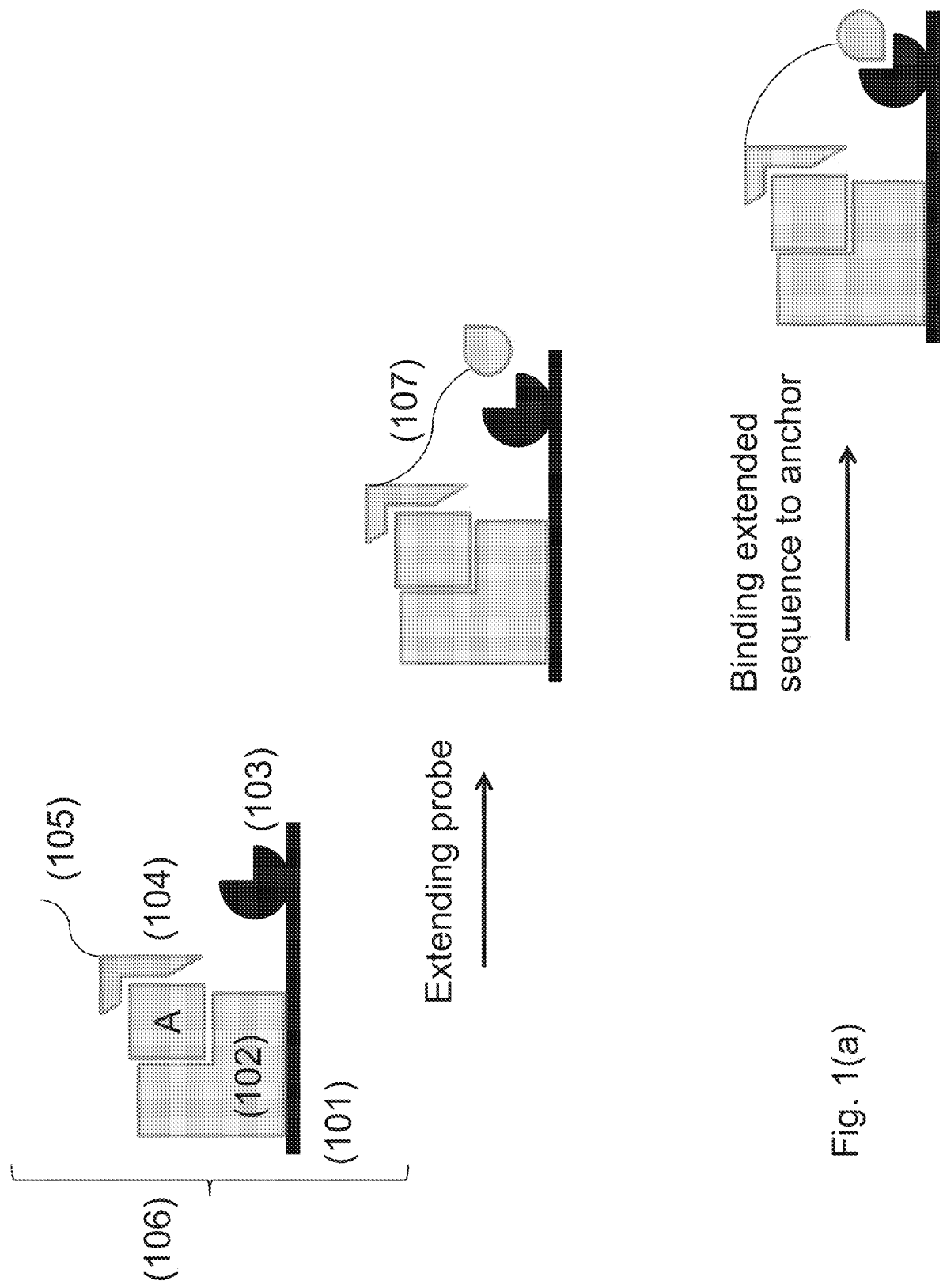

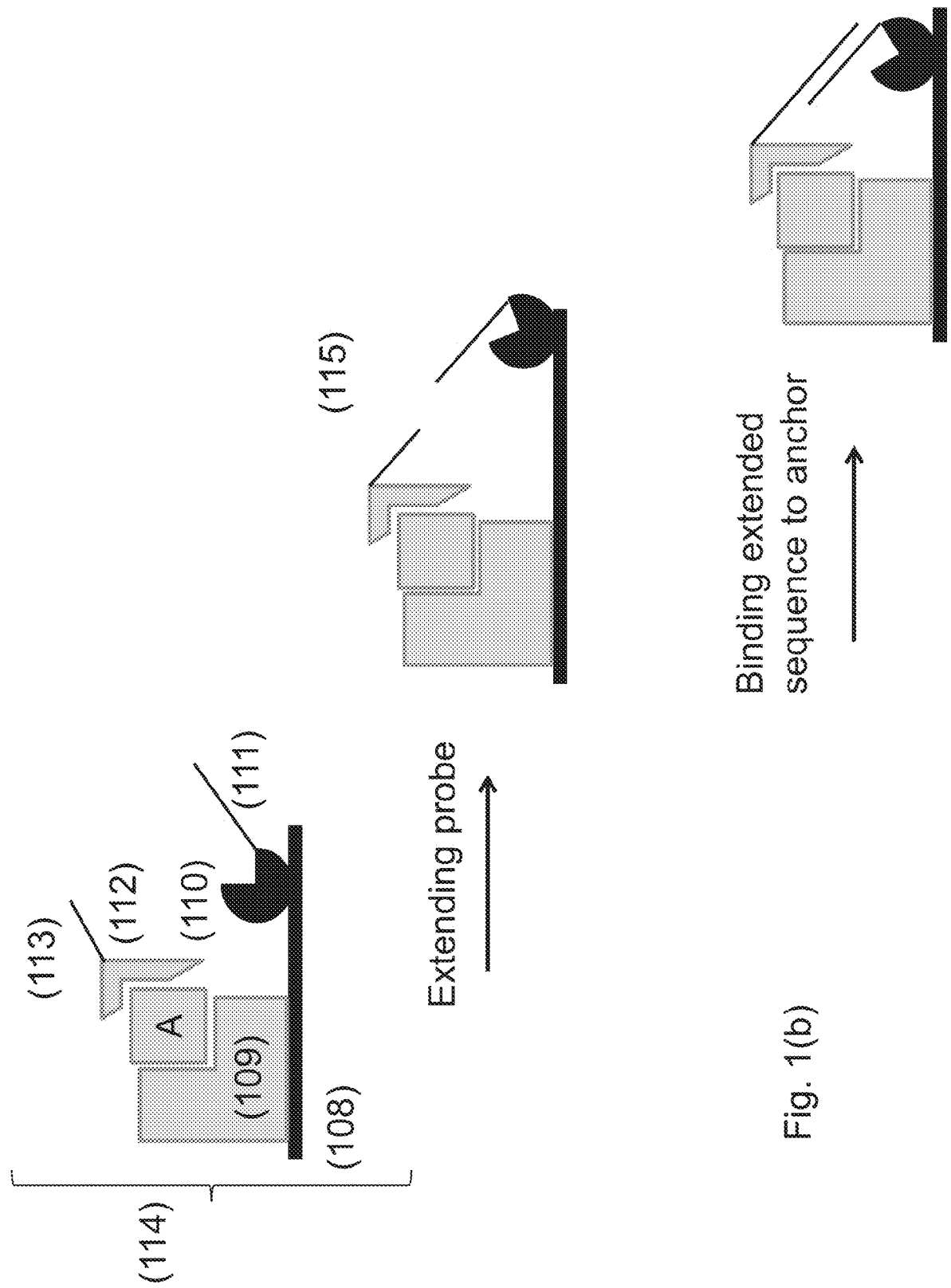

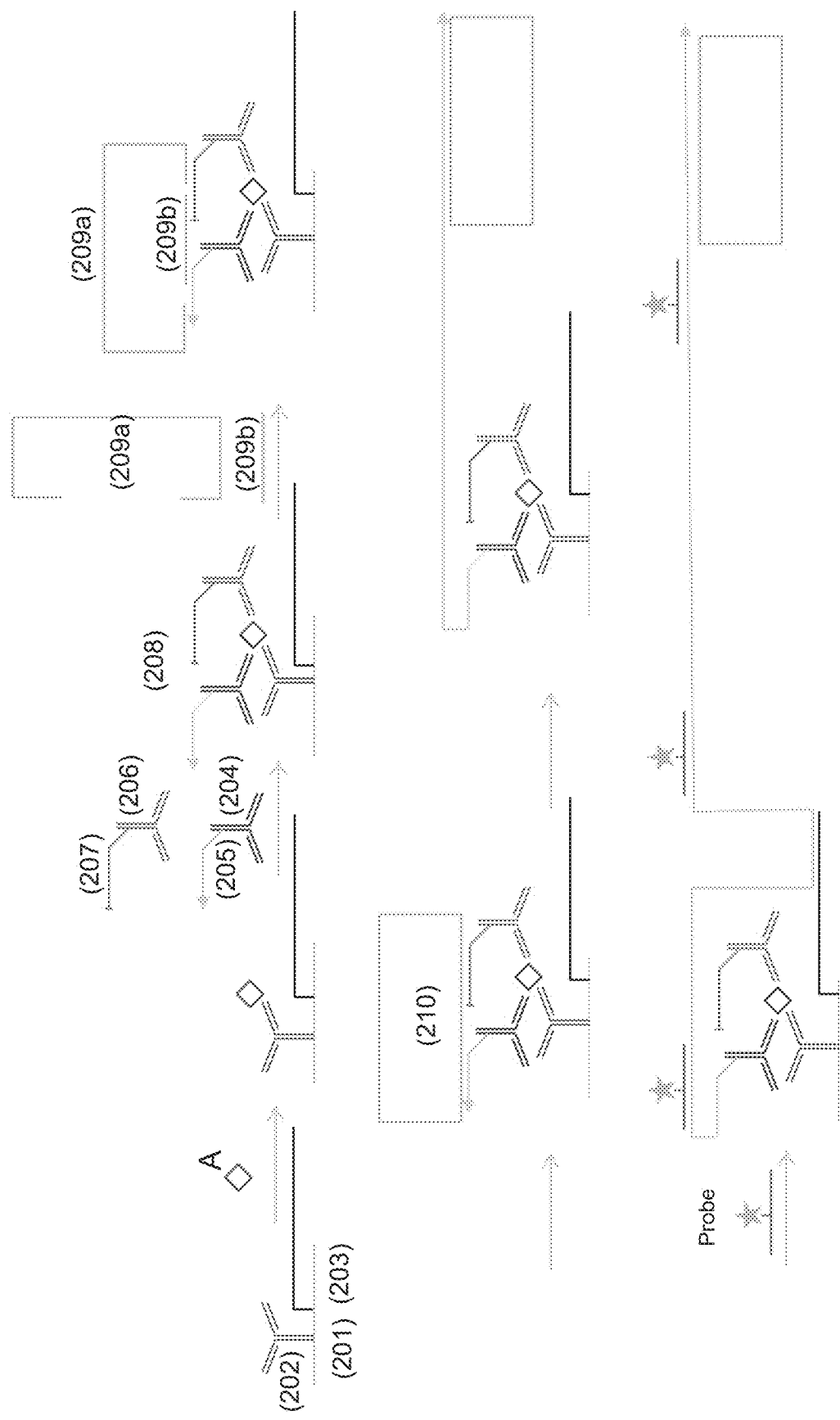

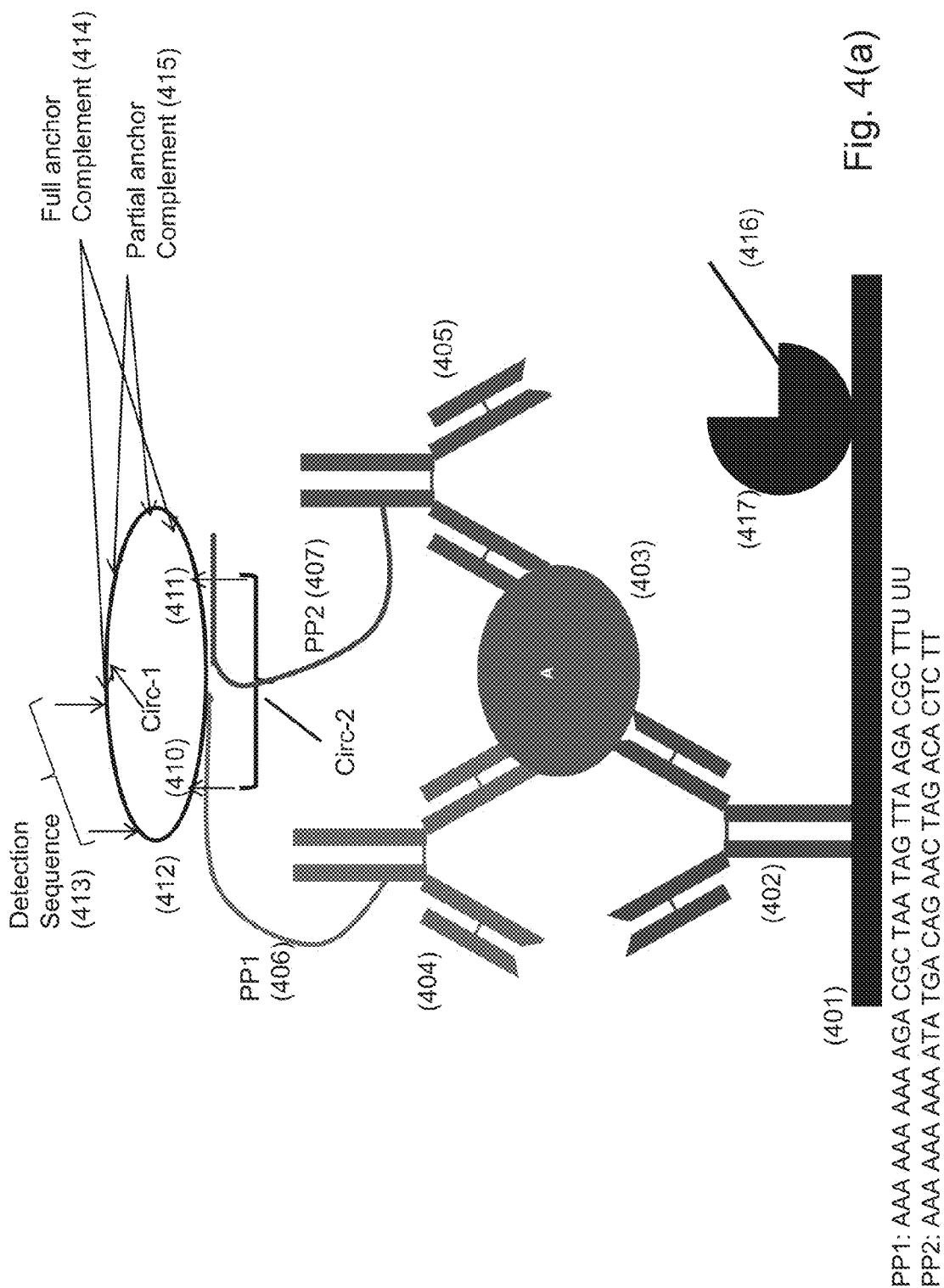

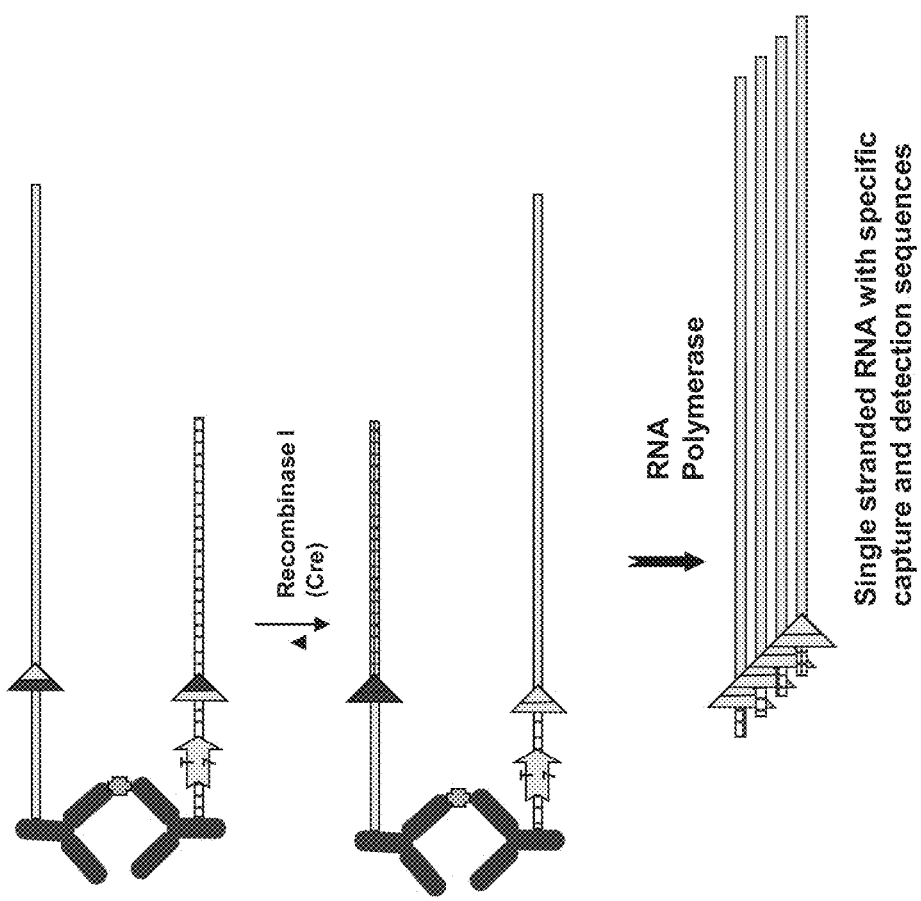

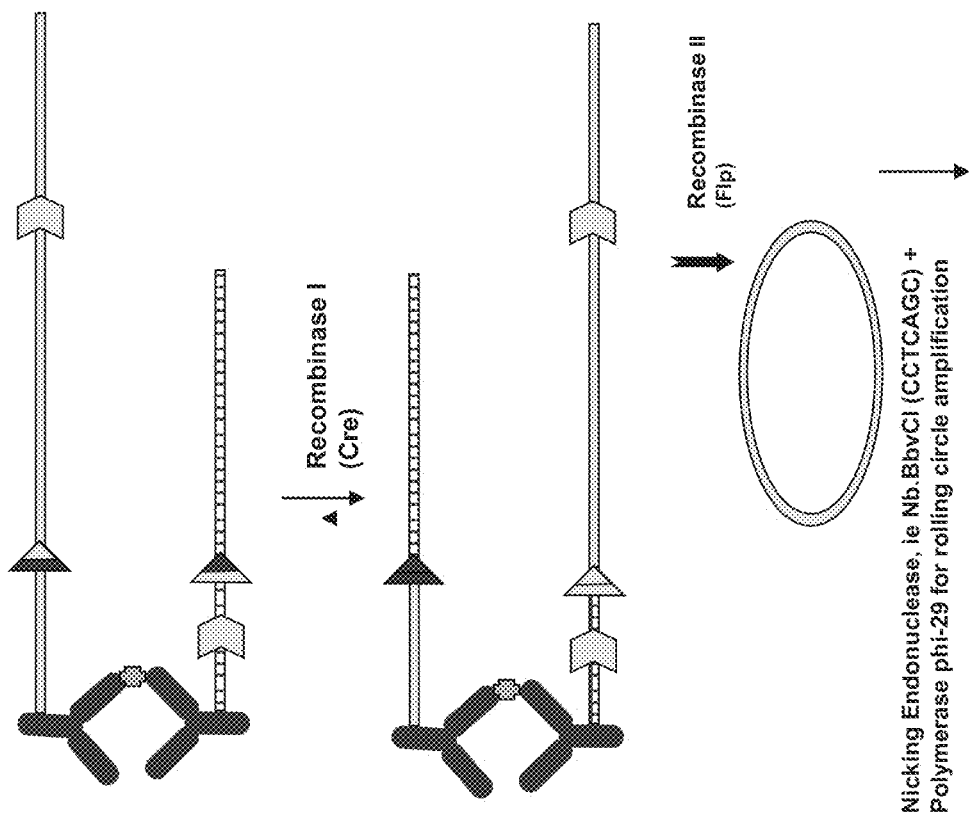

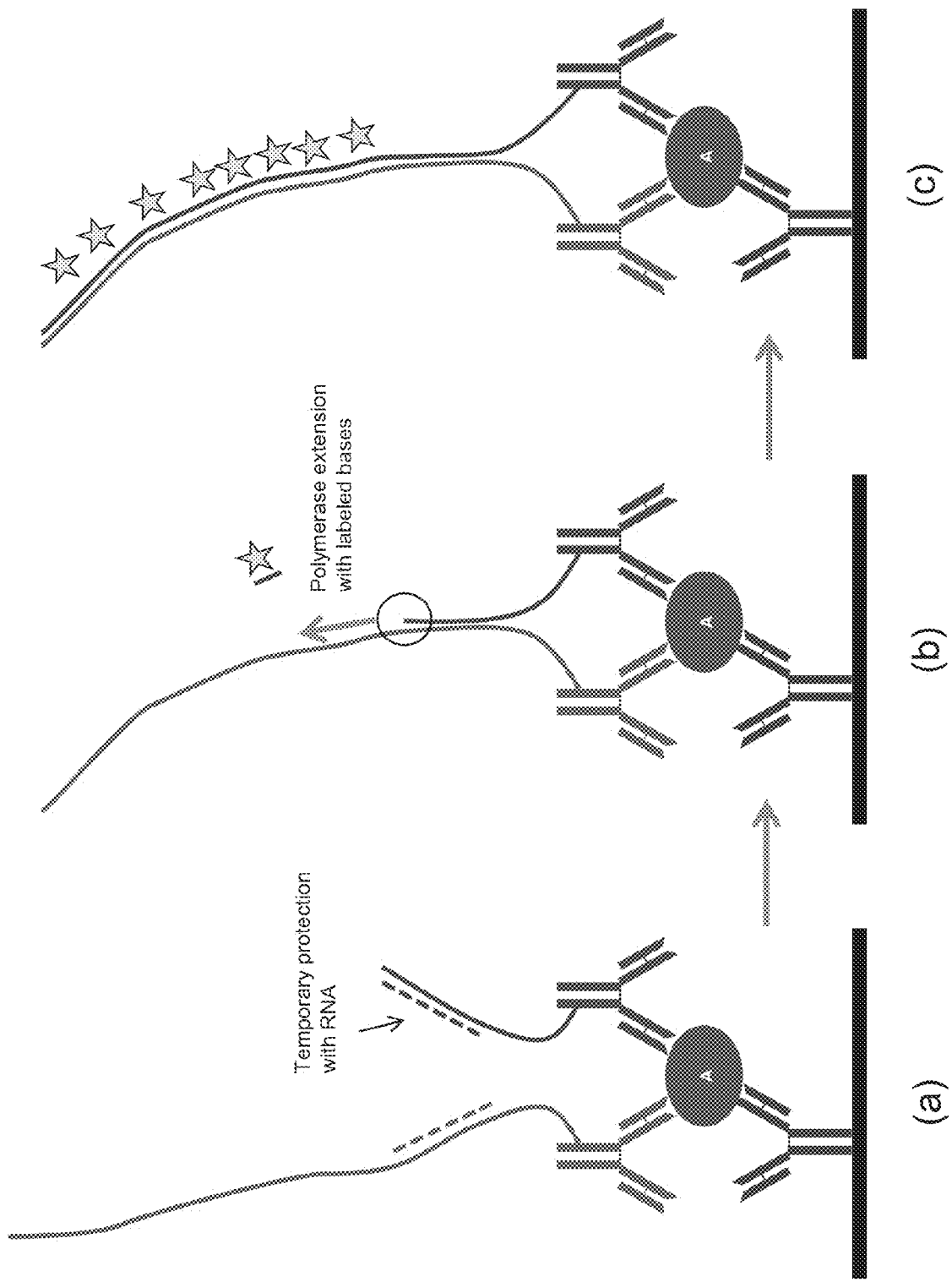

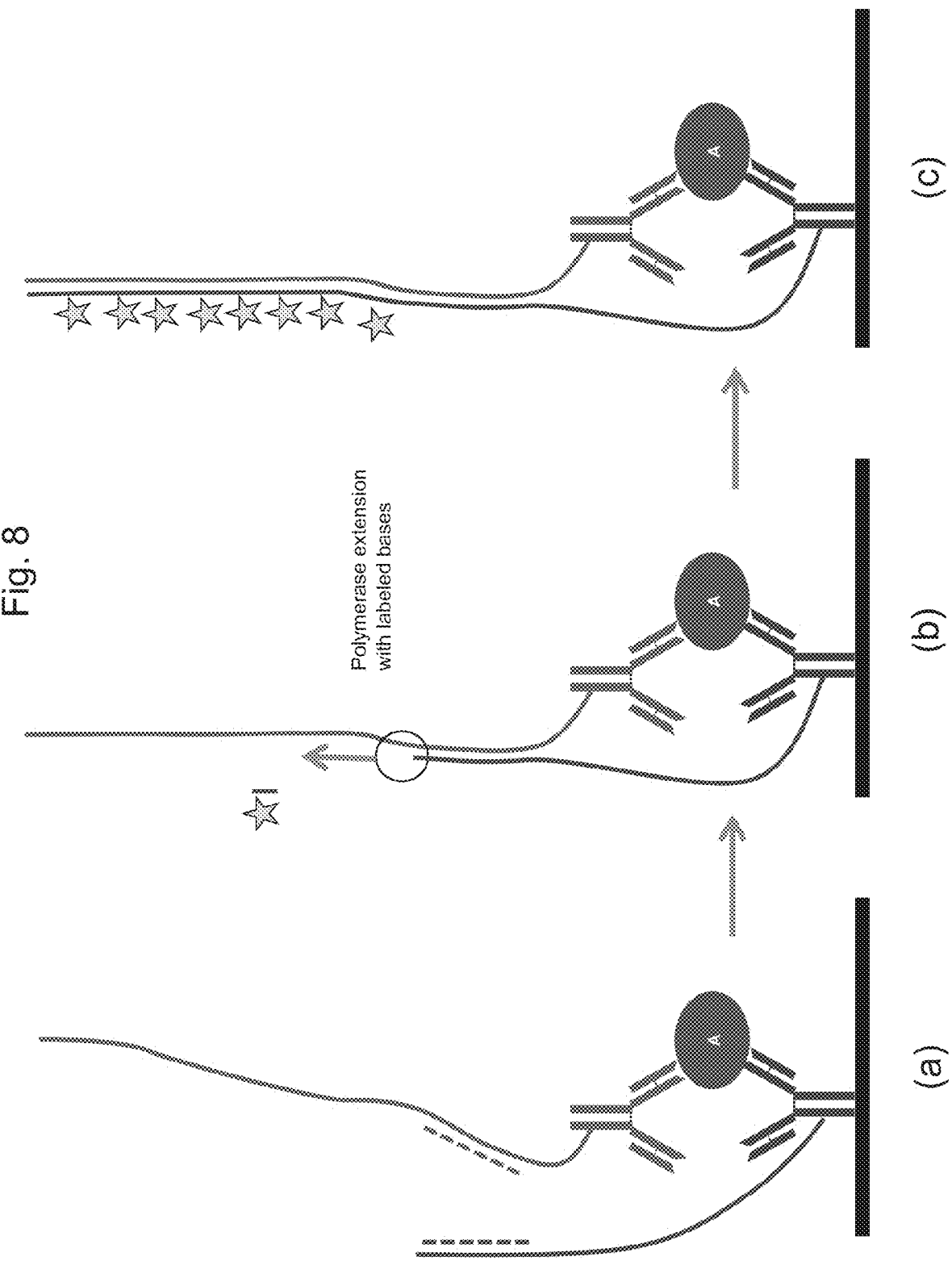

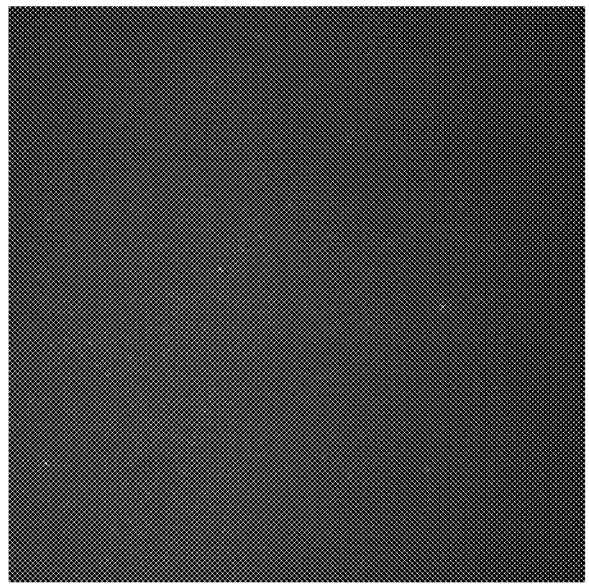
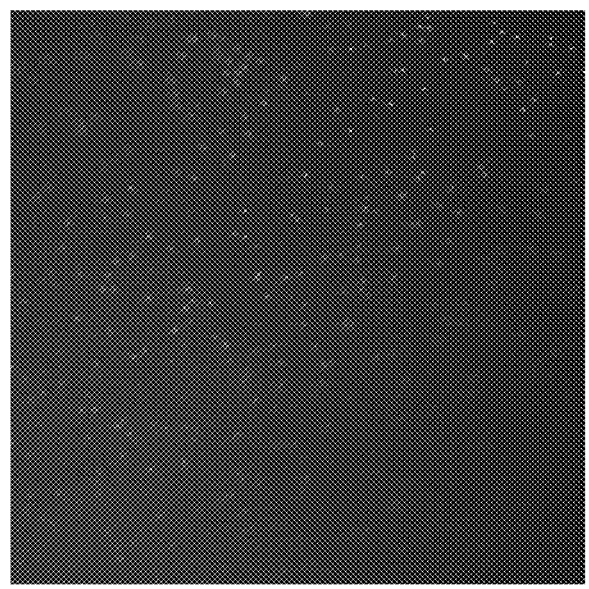
Fig. 10(a)-(b)

(a)

| Assay | HIV-1 p24 assay | | Release salt [C], Temperature | | | | | | | | Release salt [C], Temperature | | | | | | | |
|---|---|---|---|---|---|---|---|---|---|---|---|---|---|---|---|---|---|---|
| | | | 0 salt | | | 10mM | | | | | 0 salt | | | 10mM | | | | |
| | Binding [Mono+] | Bead-Capture oligo | 25C | 30C | 37C | 25C | 30C | 37C | | | 25C | 30C | 37C | 25C | 30C | 37C | | |
| Bead Cap-Release | 1M | Cap 1:13 | | 17,429 | 45,572 | | 8,236 | 32,704 | | | 8% | 4% | 13% | 20% | 9% | 28% | | |
| | | Cap 1:11 | 22,642 | 42,265 | 34,946 | 20,260 | 32,714 | 22,385 | | | 14% | 9% | 7% | 14% | 12% | 11% | | |
| | | Cap 1:10 | 43,019 | 43,260 | 34,771 | 41,851 | 37,504 | 33,651 | | | 15% | 7% | 14% | 4% | 27% | 15% | | |
| | | Cap 1:9 | 45,161 | 42,934 | 42,337 | 43,245 | 42,635 | 40,488 | | | 10% | 12% | 4% | 8% | 9% | 4% | | |
| | 0.5M | Cap 1:13 | | 9,082 | 40,514 | | 11,878 | 37,773 | | | 20% | 9% | 12% | 17% | 15% | 13% | | |
| | | Cap 1:11 | 13,016 | 35,286 | 33,755 | 25,633 | 32,878 | 24,881 | | | 3% | 16% | 19% | 12% | 11% | 14% | | |
| | | Cap 1:10 | 28,898 | 38,518 | 37,488 | 45,106 | 44,400 | 35,133 | | | 12% | 11% | 15% | 11% | 15% | 12% | | |
| | | Cap 1:9 | 30,627 | 38,024 | 40,903 | 48,526 | 44,581 | 42,991 | | | 17% | 17% | 29% | 10% | 13% | 9% | | |

(b)

| Cntrl - beads w/o cap oligo | | | |
|---|---|---|---|
| No low salt treatment | 25C | 30C | 37C |
| Binding [Mono+] | | | |
| 1M | | | |
| 0.5M | | 47,212 | 7% |
| 1M | 13% | 9% | 8% |
| 0.5M | 18% | 8% | |

(c)

| Direct plate assay | | ECL | NSB |
|---|---|---|---|
| | Dil 2/11 | 241,492 | 80 |
| | 1M | 107,573 | |
| | 0.5M | 213,186 | 105 |
| | Dil 2/11 | | 32 |
| | 1M | 6% | |
| | 0.5M | 5% | |
| | | 9% | 32 |

Fig. 14(a)-(c)

SEQUENCE LISTING

<160> NUMBER OF SEQ ID NOS: 32

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (33)..(35)
<223> OTHER INFORMATION: 2' O-methyl nucleotide

<400> SEQUENCE: 1
aaaaaaaaaa gacgctaata gttaagacgc ttuuu                             35

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Thiol-modified proximity probe 2

<400> SEQUENCE: 2
aaaaaaaaaa tatgacagaa ctagacactc tt                                32

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Anchoring oligonucleotide

<400> SEQUENCE: 3
aagagagtag tacagcagcc gtcaaaaaaa aaaaa                             35

<210> SEQ ID NO 4
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Circ-1

<400> SEQUENCE: 4
ctattagcgt ccagtgaatg cgagtccgtc taagagagta gtagagcagc cgtcaagagt   60
gtcta                                                              65

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Circ-2

```
<400> SEQUENCE: 5
gttctgtcat atttaagcgt cttaa                                          25

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Detection probe

<400> SEQUENCE: 6
cagtgaatgc gagtccgtct                                                20

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Detection oligonucleotide

<400> SEQUENCE: 7
acatcggtag tt                                                        12

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Proximity oligonucleotide 1
<220> FEATURE:
<221> NAME/KEY: misc_feature
<222> LOCATION: (1)..(10)
<223> OTHER INFORMATION: PolyA site
<220> FEATURE:
<221> NAME/KEY: modified_base
<222> LOCATION: (35)..(37)
<223> OTHER INFORMATION: 2' O-methyl nucleotide

<400> SEQUENCE: 8
aaaaaaaaaa cactaagctg ttagtccatt accguuu                             37

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Proximity oligonucleotide 2
<220> FEATURE:
<221> NAME/KEY: misc_feature
<222> LOCATION: (1)..(10)
<223> OTHER INFORMATION: PolyA site

<400> SEQUENCE: 9
aaaaaaaaaa gctggaggtt cagacgattt tgcg                                34
```

<210> SEQ ID NO 10
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Circ-1a

<400> SEQUENCE: 10
aacagcttag tgacatcggt agttaacaga ttgatcttga cacatcggta gttcgcaaaa    60
tcgtc                                                                65

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Circ-2a

<400> SEQUENCE: 11
tgaacctcca gctttcggta atggact                                        27

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Anchor oligonucleotide

<400> SEQUENCE: 12
acagattgat cttgaaaaaa aaaaaaaaaa aaaaa                               35

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Proximity oligonucleotide 1
<220> FEATURE:
<221> NAME/KEY: misc_feature
<222> LOCATION: (1)..(10)
<223> OTHER INFORMATION: PolyA site
<220> FEATURE:
<221> NAME/KEY: modified_base
<222> LOCATION: (35)..(37)
<223> OTHER INFORMATION: 2' O-methyl nucleotide

<400> SEQUENCE: 13
aaaaaaaaaa agagtccaga ggcaaagcgt gaatuuu                             37

<210> SEQ ID NO 14
<211> LENGTH: 34
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Proximity oligonucleotide 2
<220> FEATURE:
<221> NAME/KEY: misc_feature
<222> LOCATION: (1)..(10)
<223> OTHER INFORMATION: PolyA site

<400> SEQUENCE: 14
aaaaaaaaaa gataaggaag gggccttagc gaca                                    34

<210> SEQ ID NO 15
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Circ-1b

<400> SEQUENCE: 15
cctctggact ctacatcggt agtttggaac attttattct aacatcggta gtttgtcgct        60
aaggc                                                                    65

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Circ-2b

<400> SEQUENCE: 16
cccttcctta tctttattca cgctttg                                            27

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Anchor oligonucleotide

<400> SEQUENCE: 17
ggaacatttt attctaaaaa aaaaaaaaaa aaaaa                                   35

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Proximity oligonucleotide 1
<220> FEATURE:
<221> NAME/KEY: misc_feature
<222> LOCATION: (1)..(10)
<223> OTHER INFORMATION: PolyA site
<220> FEATURE:
```

```
<221> NAME/KEY: modified_base
<222> LOCATION: (35)..(37)
<223> OTHER INFORMATION: 2' O-methyl nucleotide

<400> SEQUENCE: 18
aaaaaaaaaa aacaactccg attgcttgct tcttuuu                               37

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Proximity oligonucleotide 2
<220> FEATURE:
<221> NAME/KEY: misc_feature
<222> LOCATION: (1)..(10)
<223> OTHER INFORMATION: PolyA site

<400> SEQUENCE: 19
aaaaaaaaaa tagccctacg tgccctgcat agac                                  34

<210> SEQ ID NO 20
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Circ-1c

<400> SEQUENCE: 20
atcggagttg ttacatcggt agttcgcgca ggtcgggaat tacatcggta gttgtctatg      60
caggg                                                                  65

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Circ-2c

<400> SEQUENCE: 21
cacgtagggc tatttaagaa gcaagca                                          27

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Anchor oligonucleotide

<400> SEQUENCE: 22
gcgcaggtcg ggaataaaaa aaaaaaaaaa aaaaa                                 35

<210> SEQ ID NO 23
<211> LENGTH: 35
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: PP1 sequence
<220> FEATURE:
<221> NAME/KEY: modified_base
<222> LOCATION: (33)..(35)
<223> OTHER INFORMATION: 2' O-methyl nucleotide

<400> SEQUENCE: 23
aaaaaaaaaa gacgctaata gttaagacgc ttuuu                                35

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
aagcgtctta actatt                                                     16

<210> SEQ ID NO 25
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Capture oligonucleotide 2

<400> SEQUENCE: 25
aagcgtctta act                                                        13

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Capture oligonucleotide 3

<400> SEQUENCE: 26
aagcgtctta ac                                                         12

<210> SEQ ID NO 27
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Capture oligonucleotide 4

<400> SEQUENCE: 27
aagcgtctta a                                                          11
```

```
<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Capture oligonucleotide 5

<400> SEQUENCE: 28
aagcgtctta                                                                  10

<210> SEQ ID NO 29
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Capture oligonucleotide 6

<400> SEQUENCE: 29 aagcgtctt                                                                    9

<210> SEQ ID NO 30
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Capture oligonucleotide 7

<400> SEQUENCE: 30 aagcgtct                                                                     8

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Thiol-modified proximity probe 1
<220> FEATURE:
<221> NAME/KEY: modified_base
<222> LOCATION: (25)..(27)
<223> OTHER INFORMATION: 2' O-methyl nucleotide

<400> SEQUENCE: 31
aagacgctaa tagttaagac gcttuuu                                               27

<210> SEQ ID NO 32
<211> LENGTH: 31
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Thiol-modified proximity probe 2

<400> SEQUENCE: 32
aaaaaaaaaa atatgacaga actagacact c                                   31
```

ASSAY KITS

CROSS REFERENCE TO RELATED APPLICATIONS

The present application is a divisional of copending U.S. patent application Ser. No. 15/311,309, filed Nov. 15, 2016, which claims benefit of U.S. Provisional Application Nos. 61/993,581 filed May 15, 2014; 62/013,823 filed Jun. 18, 2014; 62/048,489 filed Sep. 10, 2014; 62/049,520 filed Sep. 12, 2014; and 62/055,093 filed Sep. 25, 2014, the entire contents of which are incorporated herein by reference. Reference is also made to U.S. Ser. No. 14/206,284 (Publication No. US-2014/0272939); U.S. Ser. No. 14/208,040 (Publication No. US-2014/0274775); and U.S. Ser. No. 14/203,638 (Publication No. US-2014/0256588), the disclosures of which are also incorporated herein by reference.

REFERENCE TO AN ELECTRONIC SEQUENCE LISTING

The instant application contains a Sequence Listing which has been submitted electronically in ASCII format and is hereby incorporated by reference in its entirety. Said ASCII copy, created on Jul. 27, 2021, is named 0076-0025US2_SL.txt and is 10,916 bytes in size.

FIELD OF THE INVENTION

The present invention is directed to improved methods for conducting immunoassays. The methods are designed to amplify signals in immunoassays and anchor immunoassay complexes employed therein.

BACKGROUND OF THE INVENTION

A substantial body of literature has been developed concerning techniques that employ binding reactions, e.g., antigen-antibody reactions, nucleic acid hybridization and receptor-ligand reactions, for the sensitive measurement of analytes of interest in samples. The high degree of specificity in many biochemical binding systems has led to many assay methods and systems of value in a variety of markets including basic research, human and veterinary diagnostics, environmental monitoring and industrial testing. The presence of an analyte of interest may be measured by directly measuring the participation of the analyte in a binding reaction. In some approaches, this participation may be indicated through the measurement of an observable label attached to one or more of the binding materials.

While the sandwich immunoassay format provides excellent sensitivity and specificity in many applications, some analytes are present at concentrations that are too low for detection by conventional immunoassay techniques. The performance of sandwich immunoassays can also be limited by the non-specific binding of detection antibodies and by the instability of sandwich complexes comprising high off-rate antibodies. However, efforts to modify conventional immunoassay techniques to improve sensitivity and specificity often yield more complex, labor intensive protocols that can be hampered by inefficiencies at each step that can greatly impact the sensitivity and specificity of an assay. For example, in a complex assay requiring multiple binding events and/or reactions, if any one event or reaction is less than optimal, the sensitivity and specificity of the overall assay can suffer. There is a need for new techniques for improving sandwich immunoassay performance by improving sensitivity, reducing non-specific binding and improving the stability of sandwich complexes.

SUMMARY OF THE INVENTION

The present invention contemplates the following specific embodiments. Various modifications, additions and alterations may be made to embodiments described herein by one skilled in the art without departing from the spirit and scope of the invention. Such modifications, additions, and alterations are intended to fall within the scope of the claims.

Embodiment (1): a method of detecting an analyte of interest in a sample comprising: binding the analyte to: (i) a capture reagent on a surface comprising the capture reagent for the analyte, and an anchoring reagent; and (ii) a detection reagent for the analyte that is linked to a nucleic acid probe; thereby forming a complex on the surface comprising the capture reagent, the analyte and the detection reagent; extending the probe to form an extended sequence comprising an anchoring region that binds the anchoring reagent; binding the extended sequence to the anchoring reagent; and measuring the amount of extended sequence bound to the surface.

In embodiment (1), the capture reagent can be an antibody, antigen, ligand, receptor, oligonucleotide, hapten, epitope, mimitope, or an aptamer. In a specific embodiment, the capture reagent is an antibody. The detection reagent can be an antibody, antigen, ligand, receptor, oligonucleotide, hapten, epitope, mimitope, or an aptamer, and in a specific embodiment, the detection reagent is an antibody. In one specific example of embodiment (1), the capture and detection reagents are antibodies to the analyte. The anchoring reagent can include an oligonucleotide sequence, aptamer, aptamer ligand, antibody, antigen, ligand, receptor, hapten, epitope, or a mimetope; and optionally, the anchoring region can include an aptamer and the anchoring reagent can include an aptamer ligand. The anchoring region can comprise a nucleic acid sequence and the anchoring reagent can include a DNA-binding protein. The anchoring reagent can include an oligonucleotide sequence and the anchoring reagent can include a complementary oligonucleotide sequence. The anchoring region can include a single stranded oligonucleotide sequence or a double stranded oligonucleotide sequence.

The binding step of embodiment (1) can further include forming a triple helix between the anchoring region and the anchoring reagent. The method can also further comprise denaturing the anchoring region to expose a single stranded sequence prior to the binding step; exposing the anchoring region to helicase activity prior to the binding step; and/or exposing the anchoring region to nuclease treatment prior to the binding step. In this embodiment, the anchoring region can comprise one or more hapten-modified bases and the anchoring reagent can include one or more antibodies specific for the hapten; and/or the anchoring region can include one or more ligand-modified bases and the anchoring reagent can include one or more receptors specific for the ligand. The extended sequence can further comprise one or more detection sequences and the measuring step can include contacting the extended sequence with a plurality of labeled probes complementary to the one or more detection sequences; the extended sequence can include one or more modified bases and the measuring step can include contacting the extended sequence with a plurality of detectable moieties capable of binding to the one or more modified bases; and/or the extended sequence can comprise one or more labeled bases and the measuring step can further include detecting the presence of the one or more labeled bases. In this embodiment, the one or more modified bases comprise an aptamer, aptamer ligand, antibody, antigen, ligand, receptor, hapten, epitope, or a mimetope and the plurality of detectable moieties each comprise a binding partner of the one or more modified bases and a detectable label. The one or more modified bases can comprise streptavidin and the plurality of detectable moieties each comprise biotin and a detectable label; and/or the one or more modified bases can comprise biotin and the plurality of detectable moieties each comprise streptavidin and a detectable label; and/or the one or more modified bases can comprise avidin and the plurality of detectable moieties each comprise biotin and a detectable label; and/or the one or more modified bases can comprise biotin and the plurality of detectable moieties each comprise avidin and a detectable label.

The first step of embodiment (1) can comprise binding the analyte to the following species in the following order: (i) the capture reagent on a surface; and (ii) the detection reagent for the analyte; or the first step of embodiment (1) can comprise binding the analyte to the following species in the following order: (i) the detection reagent for the analyte; and (ii) the capture reagent on the surface; and/or the first step can comprise binding the analyte to the following species simultaneously or substantially simultaneously: (i) the capture reagent on a surface; and (ii) the detection reagent for the analyte.

The extending step of embodiment (1) can comprise binding the probe to a template nucleic acid sequence and extending the probe by polymerase chain reaction; and/or binding the probe to a template nucleic acid sequence, forming a circular nucleic acid template, and extending the circular template by rolling circle amplification. In this embodiment, the extended probe can remain localized on the surface following probe extension. Therefore, the complex can remain bound to the surface after the extending step, e.g., the extended probe is bound to the anchoring reagent at a position within 10-100 um of the location of the complex on the surface. In one specific embodiment, the extended probe is bound to the anchoring reagent at a position less than 100 um, less than 50 um, or more particularly, less than 10 um from the location of the complex on the surface.

The extending step of embodiment (1) can comprise PCR (Polymerase Chain Reaction), LCR (Ligase Chain Reaction), SDA (Strand Displacement Amplification), 3SR (Self-Sustained Synthetic Reaction), or isothermal amplification methods. In one embodiment, the extending step can include isothermal amplification methods, e.g., helicase-dependent amplification or rolling circle amplification (RCA).

The surface referenced in embodiment (1) can comprise a particle and/or a well of a multi-well plate. The surface can comprise a plurality of distinct binding domains and the capture reagent and the anchoring reagent are located on two distinct binding domains on the surface. If the surface is a well of a plate, the well can comprise a plurality of distinct binding domains and the capture reagent and the anchoring reagent are located on two distinct binding domains within the well; and/or the surface can include a plurality of distinct binding domains and the capture reagent and the anchoring reagent are located on the same binding domain on the surface. In one embodiment, the well can include a plurality of distinct binding domains and the capture reagent and the anchoring reagent are located on the same binding domain within the well. The capture reagent and the anchoring reagent may be within 10-100 nm on the surface. The surface can include an electrode and the measuring step further can include applying a voltage waveform to the electrode to generate an electrochemiluminesce signal, and optionally, the method includes collecting the particle on an electrode and applying a voltage waveform to the electrode to generate an electrochemiluminescence signal.

The measuring step of embodiment (1) can further comprise binding the extended sequence to a detection probe having a detectable label, measuring the detectable label and correlating the measurement to the amount of analyte in the sample, wherein the detection probe comprising a nucleic acid sequence that is complementary to a region of the extended sequence. The detectable label can be measured by a measurement of light scattering, optical absorbance, fluorescence, chemiluminescence, electrochemiluminescence, bioluminescence, phosphorescence, radioactivity, magnetic field, or combinations thereof. In a particular example of embodiment (1), the detectable label is an ECL label and the measuring step can include measuring an ECL signal.

Embodiment (2): a kit for the detection of an analyte of interest in a sample comprising, in one or more vials, containers, or compartments: (a) a surface comprising (i) a capture reagent for the analyte, and (ii) an anchoring reagent; and (b) a detection reagent for the analyte that is linked to a nucleic acid probe.

The anchoring reagent of embodiment (2) can comprise an oligonucleotide sequence, aptamer, aptamer ligand, antibody, antigen, ligand, receptor, hapten, epitope, or a mimetope, and the capture reagent can comprise an antibody, antigen, ligand, receptor, oligonucleotide, hapten, epitope, mimitope, or aptamer. In a particular embodiment, the capture reagent can include an antibody and/or the detection reagent can include an antibody, antigen, ligand, receptor, oligonucleotide, hapten, epitope, mimitope, or aptamer. In a specific embodiment of the kit, the detection reagent is an antibody.

The surface of the kit of embodiment (2) can include a particle and/or a well of a multi-well plate. The surface can comprise a plurality of distinct binding domains and the capture reagent and the anchoring reagent are located on two distinct binding domains on the surface. If the surface of the kit is a well of a plate, the surface can comprise a plurality of distinct binding domains and the capture reagent and the anchoring reagent are located on two distinct binding domains within the well; and/or the surface can include a plurality of distinct binding domains and the capture reagent and the anchoring reagent are located on the same binding domain on the surface. In a particular example of the kit, the surface is a well and the well can include a plurality of distinct binding domains and the capture reagent and the anchoring reagent are located on the same binding domain within the well. The capture reagent and the anchoring reagent can be within 10-100 nm on the surface. Moreover, the surface of the kit can comprise an electrode.

Embodiment (3): a method of detecting an analyte of interest in a sample comprising: (a) binding the analyte to: (i) a capture reagent on a surface comprising the capture reagent for the analyte, and an anchoring reagent comprising an anchoring oligonucleotide sequence; and (ii) a detection reagent for the analyte that is linked to a nucleic acid probe; thereby forming a complex on the surface comprising the capture reagent, the analyte and the detection reagent; (b) extending the probe to form an extended sequence comprising an anchoring sequence complement that is complementary to the anchoring sequence; (c) hybridizing the anchoring sequence to the anchoring sequence complement; and (d) measuring the amount of extended sequence bound to the surface.

In embodiment (3), the capture reagent can be an antibody, antigen, ligand, receptor, oligonucleotide, hapten, epitope, mimitope, or an aptamer, and in a particular example, the capture reagent is an antibody. Likewise, the detection reagent is an antibody, antigen, ligand, receptor, oligonucleotide, hapten, epitope, mimitope, or an aptamer, and in a particular example of embodiment (3), the detection reagent is an antibody. In one example of embodiment (3), the capture and detection reagents are antibodies to the analyte. The anchoring oligonucleotide sequence can comprise a single stranded oligonucleotide sequence or a double stranded oligonucleotide sequence. The extended sequence may further comprise one or more detection sequences and the measuring step further can include contacting the extended sequence with a plurality of labeled probes complementary to the one or more detection sequences; alternatively or additionally, the extended sequence further can include one or more modified bases and the measuring step further can include contacting the extended sequence with a plurality of detectable moieties capable of binding to the one or more modified bases. In a particular example, the extended sequence further can include one or more labeled bases and the measuring step further can include detecting the presence of the one or more labeled bases. The one or more modified bases comprise an aptamer, aptamer ligand, antibody, antigen, ligand, receptor, hapten, epitope, or a mimetope and the plurality of detectable moieties each comprise a binding partner of the one or more modified bases and a detectable label. The one or more modified bases can comprise streptavidin and the plurality of detectable moieties each comprise biotin and a detectable label; the one or more modified bases comprise biotin and the plurality of detectable moieties each comprise streptavidin and a detectable label; the one or more modified bases comprise avidin and the plurality of detectable moieties each comprise biotin and a detectable label; and/or the one or more modified bases comprise biotin and the plurality of detectable moieties each comprise avidin and a detectable label.

Step (a) of embodiment (3) can include binding the analyte to the following species in the following order: (i) the capture reagent on a surface; and (ii) the detection reagent for the analyte. Alternatively, step (a) can include binding the analyte to the following species in the following order: (i) the detection reagent for the analyte; and (ii) the capture reagent on the surface. In yet another example, step (a) can include binding the analyte to the following species simultaneously or substantially simultaneously: (i) the capture reagent on a surface; and (ii) the detection reagent for the analyte.

The extending step of embodiment (3) can include binding the probe to a template nucleic acid sequence and extending the probe by polymerase chain reaction. Alternatively, the extending step can include binding the probe to a template nucleic acid sequence, forming a circular nucleic acid template, and extending the circular template by rolling circle amplification. The extended probe can remain localized on the surface following probe extension, e.g., the complex remains bound to the surface after the extending step. In one example, the extended probe is bound to the anchoring reagent at a position within 10-100 um of the location of the complex on the surface. In one specific embodiment, the extended probe is bound to the anchoring reagent at a position less than 100 um, less than 50 um, or more particularly, less than 10 um from the location of the complex on the surface. In this particular embodiment, the extending step can include PCR (Polymerase Chain Reaction), LCR (Ligase Chain Reaction), SDA (Strand Displacement Amplification), 3SR (Self-Sustained Synthetic Reaction), or isothermal amplification methods. For example, the extending step can include isothermal amplification methods, e.g., helicase-dependent amplification or rolling circle amplification (RCA).

The surface of embodiment (3) can comprise a particle and/or a well of a multi-well plate. The surface can comprise a plurality of distinct binding domains and the capture reagent and the anchoring reagent are located on two distinct binding domains on the surface. If the surface is a well of a plate, it can comprise a plurality of distinct binding domains and the capture reagent and the anchoring reagent are located on two distinct binding domains within the well. The surface can comprise a plurality of distinct binding domains and the capture reagent and the anchoring reagent are located on the same binding domain on the surface. If the surface is a well, it can comprise a plurality of distinct binding domains and the capture reagent and the anchoring reagent are located on the same binding domain within the well. The capture reagent and the anchoring reagent can be within 10-100 nm on the surface. In a particular example, the surface can include an electrode and the measuring step further can include applying a voltage waveform to the electrode to generate an electrochemiluminesce signal. The method can further include collecting the particle on an electrode and applying a voltage waveform to the electrode to generate an electrochemiluminescence signal. The measuring step can further comprise binding the extended sequence to a detection probe having a detectable label, measuring the detectable label and correlating the measurement to the amount of analyte in the sample, wherein the detection probe comprising a nucleic acid sequence that is complementary to a region of the extended sequence. In this embodiment, the detectable label is measured by a measurement of light scattering, optical absorbance, fluorescence, chemiluminescence, electrochemilumin-escence, bioluminescence, phosphorescence, radioactivity, magnetic field, or combinations thereof. For example, the detectable label is an ECL label and the measuring step can include measuring an ECL signal.

Embodiment (4): a kit for the detection of an analyte of interest in a sample comprising, in one or more vials, containers, or compartments: (a) a surface comprising (i) a capture reagent for the analyte, and (ii) an anchoring reagent comprising an anchoring oligonucleotide sequence; and (b) a detection reagent for the analyte that is linked to a nucleic acid probe.

The kit of embodiment (4) includes a capture reagent comprising an antibody, antigen, ligand, receptor, oligonucleotide, hapten, epitope, mimitope, or aptamer. In a specific example, the capture reagent can include an antibody. Likewise, the detection reagent can include an antibody, antigen, ligand, receptor, oligonucleotide, hapten, epitope, mimitope, or aptamer, and particularly, the detection reagent can include an antibody.

The kit of embodiment (4) includes a surface that can comprise a particle and/or a well of a multi-well plate. The surface can include a plurality of distinct binding domains and the capture reagent and the anchoring reagent are located on two distinct binding domains on the surface. If the surface is a well, the well can include a plurality of distinct binding domains and the capture reagent and the anchoring reagent are located on two distinct binding domains within the well. The surface can comprise a plurality of distinct binding domains and the capture reagent and the anchoring reagent are located on the same binding domain on the surface, e.g., if the surface is a well, the well can include a plurality of distinct binding domains and the capture reagent and the anchoring reagent are located on the same binding domain within the well. For example, the capture reagent and the anchoring reagent are within 10-100 nm on the surface. The surface of embodiment (4) can include an electrode.

Embodiment (5): a method of detecting an analyte of interest in a sample comprising: (a) binding the analyte to: (i) a capture reagent on a surface comprising the capture reagent for the analyte, and an anchoring reagent comprising an anchoring oligonucleotide sequence; (ii) a first detection reagent for the analyte that is linked to a first nucleic acid probe; and (iii) a second detection reagent for the analyte that is linked to a second nucleic acid probe; thereby forming a complex on the surface comprising the binding reagent, the analyte and the first and second detection reagents; (b) using an extension process that requires the first and second probes to be in proximity, extending the second probe to form an extended sequence comprising an anchoring sequence complement that is complementary to the anchoring sequence; (c) hybridizing the anchoring sequence to the anchoring sequence complement; and (d) measuring the amount of extended sequence bound to the surface.

The capture reagent of embodiment (5) can be an antibody, antigen, ligand, receptor, oligonucleotide, hapten, epitope, mimitope, or an aptamer. In a specific example, the capture reagent is an antibody. Likewise, the first detection reagent is an antibody, antigen, ligand, receptor, oligonucleotide, hapten, epitope, mimitope, or an aptamer, and in a particular example, the first detection reagent is an antibody. The second detection reagent can be an antibody, antigen, ligand, receptor, oligonucleotide, hapten, epitope, mimitope, or an aptamer, and in a particular example, the second detection reagent is an antibody. More particularly, the capture reagent and the first and second detection reagents are antibodies to the analyte.

In embodiment (5), the anchoring oligonucleotide sequence can include a single stranded oligonucleotide sequence or a double stranded oligonucleotide sequence. In this embodiment, the extended sequence further can include one or more detection sequences and the measuring step further can include contacting the extended sequence with a plurality of labeled probes complementary to the one or more detection sequences. The extended sequence can also include one or more modified bases and the measuring step further can include contacting the extended sequence with a plurality of detectable moieties capable of binding to the one or more modified bases. The extended sequence can further comprise one or more labeled bases and the measuring step further can include detecting the presence of the one or more labeled bases. The one or more modified bases can comprise an aptamer, aptamer ligand, antibody, antigen, ligand, receptor, hapten, epitope, or a mimetope and the plurality of detectable moieties each comprise a binding partner of the one or more modified bases and a detectable label. For example, the one or more modified bases comprise streptavidin and the plurality of detectable moieties each comprise biotin and a detectable label; the one or more modified bases comprise biotin and the plurality of detectable moieties each comprise streptavidin and a detectable label; the one or more modified bases comprise avidin and the plurality of detectable moieties each comprise biotin and a detectable label; and/or the one or more modified bases comprise biotin and the plurality of detectable moieties each comprise avidin and a detectable label.

Step (a) of embodiment (5) can include binding the analyte to the following species in the following order: (i) the capture reagent on a surface; and (ii) the detection reagent for the analyte. Alternatively, step (a) can include binding the analyte to the following species in the following order: (i) the detection reagent for the analyte; and (ii) the capture reagent on the surface; or step (a) can include binding the analyte to the following species simultaneously or substantially simultaneously: (i) the capture reagent on a surface; and (ii) the detection reagent for the analyte.

The extending step of embodiment (5) can include binding the probe to a template nucleic acid sequence and extending the probe by polymerase chain reaction. The extending step can further include binding the probe to a template nucleic acid sequence, forming a circular nucleic acid template, and extending the circular template by rolling circle amplification. The extended probe can remain localized on the surface following probe extension, e.g., the complex remains bound to the surface after the extending step. The extended probe can be bound to the anchoring reagent at a position within 10-100 um of the location of the complex on the surface. In one specific embodiment, the extended probe is bound to the anchoring reagent at a position less than 100 um, less than 50 um, or more particularly, less than 10 um from the location of the complex on the surface. The extending step can include PCR (Polymerase Chain Reaction), LCR (Ligase Chain Reaction), SDA (Strand Displacement Amplification), 3SR (Self-Sustained Synthetic Reaction), or isothermal amplification methods. In a particular example, the extending step can include isothermal amplification methods, e.g., is helicase-dependent amplification or rolling circle amplification (RCA).

The extension process of embodiment (5) can include contacting the complex formed in step (a) with a connector sequence comprising (i) an interior sequence complementary to the second probe and (ii) two end sequences complementary to non-overlapping regions of the first probe. The method can further include ligating the two end sequences of the connector oligonucleotide to form a circular target sequence that is hybridized to both the first and second probes. Alternatively, the extension process can include contacting the complex formed in step (a) of embodiment (5) with a first connector oligonucleotide sequence including a first connector probe sequence complementary to a first region of the first probe and a first region on the second probe, and a second connector oligonucleotide comprising a second probe sequence complementary to a second non-overlapping region of the first probe and a second non-overlapping region of the second probe; and optionally, ligating the first and second connector oligonucleotides to form a circular target sequence that is hybridized to both the first and second probes.

The surface of embodiment (5) can include a particle and/or a well of a multi-well plate. The surface can include a plurality of distinct binding domains and the capture reagent and the anchoring reagent are located on two distinct binding domains on the surface. If the surface is a well of a plate, the well can include a plurality of distinct binding domains and the capture reagent and the anchoring reagent are located on two distinct binding domains within the well. The surface can also include a plurality of distinct binding domains and the capture reagent and the anchoring reagent are located on the same binding domain on the surface. If the surface is a well of a plate, the well can include a plurality of distinct binding domains and the capture reagent and the anchoring reagent are located on the same binding domain within the well. The capture reagent and the anchoring reagent can be within 10-100 nm on the surface. In a specific example, the surface can include an electrode and the measuring step further can include applying a voltage waveform to the electrode to generate an electrochemiluminesce signal, and optionally, the method of embodiment (5) further includes collecting the particle on an electrode and applying a voltage waveform to the electrode to generate an electrochemiluminescence signal.

The measuring step of embodiment (5) further can include binding the extended sequence to a detection probe having a detectable label, measuring the detectable label and correlating the measurement to the amount of analyte in the sample, wherein the detection probe comprising a nucleic acid sequence that is complementary to a region of the extended sequence. The detectable label can be measured by a measurement of light scattering, optical absorbance, fluorescence, chemiluminescence, electrochemiluminescence, bioluminescence, phosphorescence, radioactivity, magnetic field, or combinations thereof. In a particular example, the detectable label is an ECL label and the measuring step can include measuring an ECL signal.

Embodiment (6): a kit for the detection of an analyte of interest in a sample comprising, in one or more vials, containers, or compartments: (a) a surface comprising (i) a capture reagent for the analyte, and (ii) an anchoring reagent comprising an anchoring oligonucleotide sequence; (b) a first detection reagent for the analyte that is linked to a first nucleic acid probe; and (c) a second detection reagent for the analyte that is linked to a second nucleic acid probe.

The capture reagent of embodiment (6) can include an antibody, antigen, ligand, receptor, oligonucleotide, hapten, epitope, mimitope, or aptamer, and in a specific example the capture reagent can include an antibody. Likewise, the first detection reagent can include an antibody, antigen, ligand, receptor, oligonucleotide, hapten, epitope, mimitope, or aptamer, and in a specific example, the first detection reagent can include an antibody. Similarly, the second detection reagent can include an antibody, antigen, ligand, receptor, oligonucleotide, hapten, epitope, mimitope, or aptamer, and in a specific example, the second detection reagent can include an antibody.

The surface of embodiment (6) can comprise a particle and/or a well of a multi-well plate. The surface can include a plurality of distinct binding domains and the capture reagent and the anchoring reagent are located on two distinct binding domains on the surface. If the surface is a well, the well can comprise a plurality of distinct binding domains and the capture reagent and the anchoring reagent are located on two distinct binding domains within the well. The surface can include a plurality of distinct binding domains and the capture reagent and the anchoring reagent are located on the same binding domain on the surface; and/or if the surface is a well, the well can include a plurality of distinct binding domains and the capture reagent and the anchoring reagent are located on the same binding domain within the well. The capture reagent and the anchoring reagent can be within 10-100 nm on the surface. In a specific example, the surface can include an electrode.

Embodiment (7): a method of detecting an analyte of interest in a sample comprising: (a) binding the analyte to: (i) a capture reagent for the analyte on a surface comprising the capture reagent and an anchoring reagent; (ii) a first detection reagent for the analyte comprising a first proximity probe, and (iii) a second detection reagent for the analyte comprising a second proximity probe; thereby forming a detection complex on the surface comprising the capture reagent, the analyte and the first and second detection reagents; (b) contacting the detection complex formed in (c) with a connector sequence comprising (i) an interior sequence complementary to the second proximity probe and (ii) two end sequences complementary to non-overlapping regions of the first proximity probe; (c) hybridizing the connector sequence to the first and second proximity probes; (d) ligating the two end sequences of the connector oligonucleotide to form a circular target sequence that is hybridized to both the first and second proximity probes; (e) extending the second proximity probe by rolling circle amplification of the target sequence to generate an amplicon comprising a binding domain that binds the anchoring reagent; (f) binding the amplicon to the anchoring reagent; and (g) measuring the amount of amplicon on the surface.

Embodiment (8): a method of detecting an analyte of interest in a sample comprising: (a) binding the analyte to: (i) a capture reagent for the analyte on a surface comprising the capture reagent and an anchoring reagent; (ii) a first detection reagent for the analyte comprising a first proximity probe, and (iii) a second detection reagent for the analyte comprising a second proximity probe; thereby forming a detection complex on the surface comprising the capture reagent, the analyte and the first and second detection reagents; (b) contacting the detection complex formed in (c) with a first connector oligonucleotide and a second connector oligonucleotide, wherein (i) a first end of the first connector and a first end of the second connector are complementary to two non-overlapping regions of the first proximity probe and (ii) a second end of the first connector and a second end of the second connector are complementary to two non-overlapping regions of the first proximity probe; (c) hybridizing the first and second connector oligonucleotides to the first and second proximity probes; (d) ligating the first and second connector oligonucleotides to form a circular target sequence that is hybridized to both the first and second proximity probes; (e) extending the second proximity probe by rolling circle amplification of the target sequence to generate an amplicon comprising a binding domain that binds the anchoring reagent; (f) binding the amplicon to the anchoring reagent; and (g) measuring the amount of amplicon on the surface.

The capture reagent of embodiments (7) and (8) can be an antibody, antigen, ligand, receptor, oligonucleotide, hapten, epitope, mimitope, or an aptamer, and in a specific example, the capture reagent is an antibody. Similarly, the first detection reagent can be an antibody, antigen, ligand, receptor, oligonucleotide, hapten, epitope, mimitope, or an aptamer, e.g., the first detection reagent is an antibody. In addition, the second detection reagent is an antibody, antigen, ligand, receptor, oligonucleotide, hapten, epitope, mimitope, or an aptamer, e.g., the second detection reagent is an antibody. In a specific example of embodiments (7) and (8), the capture reagent and the first and second detection reagents are antibodies to the analyte.

The anchoring reagent of embodiments (7) and (8) can include an oligonucleotide sequence, aptamer, aptamer ligand, antibody, antigen, ligand, receptor, hapten, epitope, or a mimetope. In one example, the binding domain can include an aptamer and the anchoring reagent can include an aptamer ligand. The binding domain can include a nucleic acid sequence and the anchoring reagent can include a DNA-binding protein; and/or the anchoring reagent can include an oligonucleotide sequence and the amplicon can include a complementary oligonucleotide sequence.

The amplicon of embodiments (7) and (8) can further comprise one or more detection sequences and the measuring step can further comprise contacting the extended sequence with a plurality of labeled probes complementary to the one or more detection sequences. Moreover, the amplicon may further comprise one or more modified bases and the measuring step further can include contacting the extended sequence with a plurality of detectable moieties capable of binding to the one or more modified bases. Still further, the amplicon may further include one or more labeled bases and the measuring step further can include detecting the presence of the one or more labeled bases. The one or more modified bases can comprise an aptamer, aptamer ligand, antibody, antigen, ligand, receptor, hapten, epitope, or a mimetope and the plurality of detectable moieties each comprise a binding partner of the one or more modified bases and a detectable label. The one or more modified bases can comprise streptavidin and the plurality of detectable moieties each comprise biotin and a detectable label; the one or more modified bases can comprise biotin and the plurality of detectable moieties each comprise streptavidin and a detectable label; the one or more modified bases can comprise avidin and the plurality of detectable moieties each comprise biotin and a detectable label; and/or the one or more modified bases can comprise biotin and the plurality of detectable moieties each comprise avidin and a detectable label.

Step (a) of embodiments (7) and (8) can comprise binding the analyte to the following species in the following order: (i) the capture reagent on a surface; and (ii) the first and second detection reagents for the analyte. Alternatively, step (a) can include binding the analyte to the following species in the following order: (i) the first and second detection reagents for the analyte; and (ii) the capture reagent on the surface. Still further, step (a) can include binding the analyte to the following species simultaneously or substantially simultaneously: (i) the capture reagent on a surface; and (ii) the first and second detection reagents for the analyte.

The amplicon of embodiments (7) and (8) can remain localized on the surface following probe extension. The complex can remain bound to the surface after the extending step. For example, the amplicon is bound to the anchoring reagent at a position within 10-100 um of the location of the complex on the surface. In one specific embodiment, the extended probe is bound to the anchoring reagent at a position less than 100 um, less than 50 um, or more particularly, less than 10 um from the location of the complex on the surface.

The surface of embodiments (7) and (8) can include a particle and/or a well of a multi-well plate. The surface can include a plurality of distinct binding domains and the capture reagent and the anchoring reagent are located on two distinct binding domains on the surface. If the surface is a well of a plate, the well can comprise a plurality of distinct binding domains and the capture reagent and the anchoring reagent are located on two distinct binding domains within the well. The surface can include a plurality of distinct binding domains and the capture reagent and the anchoring reagent are located on the same binding domain on the surface. If the surface is a well of a plate, the well can include a plurality of distinct binding domains and the capture reagent and the anchoring reagent are located on the same binding domain within the well. In a specific example, the capture reagent and the anchoring reagent are within 10-100 nm on the surface.

Still further, the surface can include an electrode and the measuring step can include applying a voltage waveform to the electrode to generate an electrochemiluminesce signal. In these embodiments ((7) and (8)), the method can further include collecting the particle on an electrode and applying a voltage waveform to the electrode to generate an electrochemiluminescence signal. The measuring step can include binding the amplicon to a detection probe having a detectable label, measuring the detectable label and correlating the measurement to the amount of analyte in the sample, wherein the detection probe comprising a nucleic acid sequence that is complementary to a region of the amplicon. The detectable label is measured by a measurement of light scattering, optical absorbance, fluorescence, chemiluminescence, electrochemiluminescence, bioluminescence, phosphorescence, radioactivity, magnetic field, or combinations thereof. For example, the detectable label is an ECL label and the measuring step can include measuring an ECL signal.

Embodiment (9): a kit for the detection of an analyte of interest in a sample comprising, in one or more vials, containers, or compartments: (a) a surface comprising (i) a capture reagent for the analyte, and (ii) an anchoring reagent; (b) a first detection reagent for the analyte comprising a first proximity probe; (c) a second detection reagent for the analyte comprising a second proximity probe; and (d) a connector sequence comprising (i) an interior sequence complementary to the second proximity probe and (ii) two end sequences complementary to non-overlapping regions of the first proximity probe.

Embodiment (10): a kit for the detection of an analyte of interest in a sample comprising, in one or more vials, containers, or compartments: (a) a surface comprising (i) a capture reagent for the analyte, and (ii) an anchoring reagent; and (b) a first detection reagent for the analyte comprising a first proximity probe; (c) a second detection reagent for the analyte comprising a second proximity probe; and (d) (i) a first connector oligonucleotide and (ii) a second connector oligonucleotide, wherein (x) a first end of the first connector and a first end of the second connector are complementary to two non-overlapping regions of the first proximity probe and (y) a second end of the first connector and a second end of the second connector are complementary to two non-overlapping regions of the first proximity probe.

The capture reagent of embodiments (9) and (10) can include an antibody, antigen, ligand, receptor, oligonucleotide, hapten, epitope, mimitope, or aptamer. In a specific example, the capture reagent can include an antibody. The first detection reagent can include an antibody, antigen, ligand, receptor, oligonucleotide, hapten, epitope, mimitope, or aptamer, and in a specific example, the first detection reagent can include an antibody. The second detection reagent can include an antibody, antigen, ligand, receptor, oligonucleotide, hapten, epitope, mimitope, or aptamer, and in a specific example, the second detection reagent can include an antibody.

The surface of embodiments (9) and (10) can include a particle and/or a well of a multi-well plate. The surface can include a plurality of distinct binding domains and the capture reagent and the anchoring reagent are located on two distinct binding domains on the surface. If the surface is a well of a plate, the well can include a plurality of distinct binding domains and the capture reagent and the anchoring reagent are located on two distinct binding domains within the well. The surface can include a plurality of distinct binding domains and the capture reagent and the anchoring reagent are located on the same binding domain on the surface. If the surface is a well, the well can include a plurality of distinct binding domains and the capture reagent and the anchoring reagent are located on the same binding domain within the well. In a specific example, the capture reagent and the anchoring reagent are within 10-100 nm on the surface.

The surface of embodiments (9) and (10) can include an electrode.

Embodiment (11): a method of detecting an analyte of interest in a sample comprising: (a) binding the analyte to: (i) a capture reagent for the analyte on a surface comprising the capture reagent and an anchoring reagent comprising an anchoring oligonucleotide sequence; (ii) a first detection reagent for the analyte comprising a first proximity probe, and (iii) a second detection reagent for the analyte comprising a second proximity probe; thereby forming a detection complex on the surface comprising the capture reagent, the analyte and the first and second detection reagents; (b) contacting the detection complex formed in (c) with a connector sequence comprising (i) an interior sequence complementary to the second proximity probe, (ii) two end sequences complementary to non-overlapping regions of the first proximity probe and (iii) a sequence matching the anchoring sequence; (c) hybridizing the connector sequence to the first and second proximity probes; (d) ligating the two end sequences of the connector oligonucleotide to form a circular target sequence that is hybridized to both the first and second proximity probes; (e) extending the second proximity probe by rolling circle amplification of the target sequence to generate an amplicon comprising a plurality of anchoring sequence complements that are complementary to the anchoring sequence; (f) hybridizing the anchoring sequence to one of the anchoring sequence complements; and (g) measuring the amount of amplicon on the surface.

Embodiment (12): a method of detecting an analyte of interest in a sample comprising: (a) binding the analyte to: (i) a capture reagent for the analyte on a surface comprising the capture reagent and an anchoring reagent comprising an anchoring oligonucleotide sequence; (ii) a first detection reagent for the analyte comprising a first proximity probe, and (iii) a second detection reagent for the analyte comprising a second proximity probe; thereby forming a detection complex on the surface comprising the capture reagent, the analyte and the first and second detection reagents; (b) contacting the detection complex formed in (a) with a first connector oligonucleotide and a second connector oligonucleotide, wherein (i) a first end of the first connector and a first end of the second connector are complementary to two non-overlapping regions of the first proximity probe, (ii) a second end of the first connector and a second end of the second connector are complementary to two non-overlapping regions of the first proximity probe and (iii) the first and/or second connector also comprise a sequence matching the anchoring sequence; (c) hybridizing the first and second connector oligonucleotides to the first and second proximity probes; (d) ligating the first and second connector oligonucleotides to form a circular target sequence that is hybridized to both the first and second proximity probes; (e) extending the second proximity probe by rolling circle amplification of the target sequence to generate an amplicon comprising a plurality of anchoring sequence complements that are complementary to the anchoring sequence; (f) hybridizing the anchoring sequence to one of the anchoring sequence complements; and (g) measuring the amount of amplicon on the surface.

The capture reagent of embodiments (11) and (12) is an antibody, antigen, ligand, receptor, oligonucleotide, hapten, epitope, mimitope, or an aptamer. In a specific example, the capture reagent is an antibody. The first detection reagent is an antibody, antigen, ligand, receptor, oligonucleotide, hapten, epitope, mimitope, or an aptamer, and in a specific example, the first detection reagent is an antibody. Likewise, the second detection reagent is an antibody, antigen, ligand, receptor, oligonucleotide, hapten, epitope, mimitope, or an aptamer, and in a specific example, the second detection reagent is an antibody. In one example, the first and second detection reagents are antibodies to the analyte.

The amplicon of embodiments (11) and (12) can further comprise one or more detection sequences and the measuring step can include contacting the extended sequence with a plurality of labeled probes complementary to the one or more detection sequences. Moreover, the amplicon can also comprise one or more modified bases and the measuring step can include contacting the extended sequence with a plurality of detectable moieties capable of binding to the one or more modified bases. The amplicon additionally include one or more labeled bases and the measuring step can include detecting the presence of the one or more labeled bases. The one or more modified bases comprise an aptamer, aptamer ligand, antibody, antigen, ligand, receptor, hapten, epitope, or a mimetope and the plurality of detectable moieties each comprise a binding partner of the one or more modified bases and a detectable label. The one or more modified bases can comprise streptavidin and the plurality of detectable moieties each comprise biotin and a detectable label; the one or more modified bases can comprise biotin and the plurality of detectable moieties each comprise streptavidin and a detectable label; the one or more modified bases can comprise avidin and the plurality of detectable moieties each comprise biotin and a detectable label; and/or the one or more modified bases can include biotin and the plurality of detectable moieties each comprise avidin and a detectable label.

Step (a) of embodiments (11) and (12) can comprise binding the analyte to the following species in the following order: (i) the capture reagent on a surface; and (ii) the first and second detection reagents for the analyte. Alternatively, step (a) can include binding the analyte to the following species in the following order: (i) the first and second detection reagents for the analyte; and (ii) the capture reagent on the surface. Still further, step (a) can include binding the analyte to the following species simultaneously or substantially simultaneously: (i) the capture reagent on a surface; and (ii) the first and second detection reagents for the analyte.

The amplicon in embodiments (11) and (12) can remain localized on the surface following probe extension, and optionally, the complex remains bound to the surface after the extending step. For example, the amplicon is bound to the anchoring reagent at a position within 10-100 um of the location of the complex on the surface. In one specific embodiment, the extended probe is bound to the anchoring reagent at a position less than 100 um, less than 50 um, or more particularly, less than 10 um from the location of the complex on the surface.

The surface of embodiments (11) and (12) can include a particle and/or a well of a multi-well plate. Optionally, the surface can include a plurality of distinct binding domains and the capture reagent and the anchoring reagent are located on two distinct binding domains on the surface. If the surface is a well, the well can include a plurality of distinct binding domains and the capture reagent and the anchoring reagent are located on two distinct binding domains within the well. The surface can include a plurality of distinct binding domains and the capture reagent and the anchoring reagent are located on the same binding domain on the surface. If the surface is a well, the well can comprise a plurality of distinct binding domains and the capture reagent and the anchoring reagent are located on the same binding domain within the well. The capture reagent and the anchoring reagent can be within 10-100 nm on the surface.

The surface of embodiments (11) and (12) can comprise an electrode and the measuring step can include applying a voltage waveform to the electrode to generate an electrochemiluminesce signal. Optionally, embodiments (11) and (12) further comprise collecting the particle on an electrode and applying a voltage waveform to the electrode to generate an electrochemiluminescence signal. The measuring step can also include binding the amplicon to a detection probe having a detectable label, measuring the detectable label and correlating the measurement to the amount of analyte in the sample, wherein the detection probe comprising a nucleic acid sequence that is complementary to a region of the amplicon. The detectable label can be measured by a measurement of light scattering, optical absorbance, fluorescence, chemiluminescence, electrochemiluminescence, bioluminescence, phosphorescence, radioactivity, magnetic field, or combinations thereof. In one example, the detectable label is an ECL label and the measuring step can include measuring an ECL signal.

The sample of embodiments (11) and (12) can comprise one or more analyte molecules, and the surface can include a plurality of capture reagents for the one or more analyte molecules distributed across a plurality of resolvable binding regions positioned on the surface, and the method can include: (x) binding the one or more analyte molecules to one or more capture reagents on the surface; (y) determining the presence or absence of an analyte molecule in each binding region; and (z) identifying the number of binding regions that contain an analyte molecule and/or the number of analyte domains that do not contain an analyte molecule. The measuring step can include imaging an optical signal from the surface to generate an image comprising a plurality of pixels and each resolvable binding region maps to one or more pixels in the image. The resolvable binding regions can be elements of an array and/or the resolvable binding regions are configured to isolate individual particles. Each resolvable binding region can be an individual nano-wells having a volume<100 nL, e.g., wherein at least 99% of the binding regions contain either zero or one analyte molecule, wherein at least about 95% of the binding regions contain either zero or one analyte molecule, wherein at least about 80% of the binding regions contain either zero or one analyte molecule, and/or wherein at least about 50% of the binding regions contain either zero or one analyte molecule. The concentration of analyte molecules in the sample in embodiments (11) and (12) can be determined at least in part using a calibration curve, a Poisson distribution analysis and/or a Gaussian distribution analysis of the number of binding regions that contain at least one or one analyte molecule.

In embodiments (11) and (12), the sample can comprise one or more analyte molecules, the surface can include a plurality of particles each comprising a plurality of binding reagents for an analyte molecule wherein the plurality of particles is distributed across a plurality of resolvable binding regions, and the method can include: (i) binding the one or more analyte molecules to one or more binding reagents on the surface, and (ii) distributing the plurality of particles across an array of resolvable binding regions; and (iii) determining the presence or absence of an analyte molecule in each resolvable binding regions, so as to identify the number of binding regions that contain an analyte molecule and/or the number of binding regions that do not contain an analyte molecule.

Embodiment (13): a kit for the detection of an analyte of interest in a sample comprising, in one or more vials, containers, or compartments: (a) a surface comprising (i) a capture reagent for the analyte, and (ii) an anchoring reagent comprising an anchoring oligonucleotide sequence; (b) a first detection reagent for the analyte comprising a first proximity probe; (c) a second detection reagent for the analyte comprising a second proximity probe; and (d) a connector sequence comprising (i) an interior sequence complementary to the second proximity probe and (ii) two end sequences complementary to non-overlapping regions of the first proximity probe.

Embodiment (14): a kit for the detection of an analyte of interest in a sample comprising, in one or more vials, containers, or compartments: (a) a surface comprising (i) a capture reagent for the analyte, and (ii) an anchoring reagent comprising an anchoring oligonucleotide sequence; and (b) a first detection reagent for the analyte comprising a first proximity probe; (c) a second detection reagent for the analyte comprising a second proximity probe; and (d) (i) a first connector oligonucleotide and (ii) a second connector oligonucleotide, wherein (x) a first end of the first connector and a first end of the second connector are complementary to two non-overlapping regions of the first proximity probe and (y) a second end of the first connector and a second end of the second connector are complementary to two non-overlapping regions of the first proximity probe.

The capture reagent of embodiments (13) and (14) can comprise an antibody, antigen, ligand, receptor, oligonucleotide, hapten, epitope, mimitope, or aptamer, e.g., the capture reagent can include an antibody. Likewise, the first detection reagent can include an antibody, antigen, ligand, receptor, oligonucleotide, hapten, epitope, mimitope, or aptamer, e.g., the first detection reagent can include an antibody. Similarly, the second detection reagent can include an antibody, antigen, ligand, receptor, oligonucleotide, hapten, epitope, mimitope, or aptamer, e.g., the second detection reagent can include an antibody.

The surface of embodiments (13) and (14) can include a particle and/or a well of a multi-well plate. The can include a plurality of distinct binding domains and the capture reagent and the anchoring reagent are located on two distinct binding domains on the surface. If the surface is a well, the well can comprise a plurality of distinct binding domains and the capture reagent and the anchoring reagent are located on two distinct binding domains within the well. The surface can include a plurality of distinct binding domains and the capture reagent and the anchoring reagent are located on the same binding domain on the surface. If the surface is a well, the well can include a plurality of distinct binding domains and the capture reagent and the anchoring reagent are located on the same binding domain within the well. The capture reagent and the anchoring reagent can be within 10-100 nm on the surface, and optionally, the surface can include an electrode.

Embodiment (15): a method of detecting analytes in a sample, wherein the method can include: (a) binding the analytes to first and second detection reagents to form detection complexes, each detection complex comprising an analyte, a first detection reagent and a second detection reagent, wherein the first detection reagent has a first detectable label and the second detection reagent has a second detectable label, (b) partitioning the analytes across a plurality of reaction vessels so that the majority of reaction vessels contain one or fewer analytes; and (c) detecting the number of analyte molecules by counting the number of reaction vessels that contain the first and second detectable labels. In this embodiment (15), the first detection reagent can be an antibody, antigen, ligand, receptor, oligonucleotide, hapten, epitope, mimitope, or an aptamer, e.g., the first detection reagent is an antibody. Likewise, the second detection reagent can be an antibody, antigen, ligand, receptor, oligonucleotide, hapten, epitope, mimitope, or an aptamer, e.g., the second detection reagent is an antibody. In a specific example, the first and second detection reagents are antibodies to the analyte.

Step (a) of embodiment (15) can further comprise forming a solution comprising said analytes and said detection reagents and step (b) can include partitioning the solution across the plurality of reaction vessels so that the likelihood of finding an unbound first detection reagent and an unbound second detection reagent in the same vessel is less than 1 in 10. Alternatively, step (a) of embodiment (15) can further comprise forming a solution comprising said analytes and said detection reagents and step (b) can include partitioning the solution across the plurality of reaction vessels so that the likelihood of finding an unbound first detection reagent and an unbound second detection reagent in the same vessel is less than 1 in 100. Still further, step (a) of embodiment (15) can further comprise forming a solution comprising said analytes and said detection reagents and step (b) can include partitioning the solution across the plurality of reaction vessels so that the likelihood of finding an unbound first detection reagent and an unbound second detection reagent in the same vessel is less than 1 in 1000. Moreover, step (a) of embodiment (15) can further comprise forming a solution comprising said analytes and said detection reagents and step (b) can include partitioning the solution across the plurality of reaction vessels so that the likelihood of finding an unbound first detection reagent and an unbound second detection reagent in the same vessel is less than 1 in 10000.

Embodiment (16): a method of detecting analytes in a sample, the method comprising: (a) binding the analytes to capture reagents and first and second detection reagents to form detection complexes, each detection complex comprising a capture reagent, an analyte, a first detection reagent and a second detection reagent, wherein (i) the first detection reagent has a first detectable label and the second detection reagent has a second detectable label, (ii) the capture reagent is on a surface; (b) partitioning the analytes across a plurality of reaction vessels so that the majority of reaction vessels contain one or fewer analytes; and (c) detecting the number of analyte molecules by counting the number of reaction vessels that contain the first and second detectable labels. In this embodiment, the capture reagent can be an antibody, antigen, ligand, receptor, oligonucleotide, hapten, epitope, mimitope, or an aptamer, e.g., the capture reagent is an antibody. Likewise, the first detection reagent can be an antibody, antigen, ligand, receptor, oligonucleotide, hapten, epitope, mimitope, or an aptamer, e.g., the first detection reagent is an antibody. Moreover, the second detection reagent can be an antibody, antigen, ligand, receptor, oligonucleotide, hapten, epitope, mimitope, or an aptamer, e.g., the second detection reagent is an antibody. For example, the capture reagent, first and second detection reagents are antibodies to the analyte.

Step (b) of embodiment (16) can further comprise partitioning the solution across the plurality of reaction vessels so that the likelihood of finding an unbound second detection reagent in the same vessel is less than 1 in 10. Moreover, step (b) of embodiment (16) can further comprise partitioning the solution across the plurality of reaction vessels so that the likelihood of finding an unbound first detection reagent and an unbound second detection reagent in the same vessel is less than 1 in 100. Step (b) of embodiment (16) can further comprise partitioning the solution across the plurality of reaction vessels so that the likelihood of finding an unbound first detection reagent and an unbound second detection reagent in the same vessel is less than 1 in 1000. Further, step (b) of embodiment (16) can further comprise partitioning the solution across the plurality of reaction vessels so that the likelihood of finding an unbound first detection reagent and an unbound second detection reagent in the same vessel is less than 1 in 10000.

The capture reagent in the detection complex of embodiment (16) can be on the surface prior to binding the capture reagent to the analyte; or the capture reagent in the detection complex binds to the analyte prior to immobilizing the capture reagent on the surface. In one example, the capture reagent can include a targeting moiety and the surface can include a targeting moiety complement. The targeting moiety and the targeting agent binding partner are selected from the following binding pairs: avidin-biotin, streptavidin-biotin, receptor-ligand, antibody-antigen, nucleic acid-nucleic acid complement.

The surface of embodiment (16) is a particle, and optionally, the capture reagents are immobilized on a plurality of particles and the partitioning of analytes is achieved by binding the analytes to the capture reagents and partitioning the particles into the plurality of reaction vessels. The capture reagents can be immobilized on a plurality of particles and the partitioning of analytes is achieved by partitioning the particles into a plurality of reaction vessels and then binding the analytes to the capture reagents.

Embodiment (16) can further comprise partitioning a plurality of particles into the plurality of reaction vessels, wherein the plurality of particles comprise targeting moieties, the capture reagents comprise a targeting moiety complement and the partitioning of analytes is achieved by binding the targeting moiety complements to the targeting moieties. Embodiment (16) can also include washing the particles prior to the partitioning step and/or after the partitioning step.

The surface of embodiment (16) can be a location within one of the reaction vessels. In this embodiment, the capture reagents can be immobilized on surfaces of the plurality of reaction vessels and the partitioning of analytes is achieved by binding the analytes to the capture reagents. Optionally, the reaction vessels have surfaces with targeting moieties immobilized thereon, the capture reagents comprise targeting moiety complements, and the partitioning of analytes is achieved by binding the targeting moiety complements to the targeting moieties. In this specific example, the method can further comprise washing the reaction vessel prior to the detection step.

The plurality of reaction vessels of embodiment (16) can comprise an array of nanowells. The plurality of reaction vessels can comprise at least 10,000 reaction vessels. In one embodiment, the reaction vessels have a volume of less than 100 nL. Optionally, less than 50% of the reaction vessels contain an analyte at the time of detection, less than 10% of the reaction vessels contain an analyte at the time of detection, less than 1% of the reaction vessels contain an analyte at the time of detection, and/or less than 0.1% of the reaction vessels contain an analyte at the time of detection.

In one aspect of embodiment (16), the first detectable label is a first enzyme of a coupled enzyme reaction system and the second detectable label is a second enzyme of the couple enzyme reaction system and the step (d) can include adding one or more substrates of the reaction system, producing a product of the enzyme reaction system and counting the reaction vessels that contain the product. In this embodiment, the product may only be produced when the first enzyme and second enzyme are in close proximity, e.g., the first and second enzymes are within 200 nM of each other, or the first and second enzymes are within 50 nM of each other. For example, the first enzyme is an oxidase, the second enzyme is a peroxidase, and the substrates comprise an oxidase substrate and a labeled Amplex Red or luminol derivative. In this embodiment, the oxidase can be glucose oxidase and the oxidase substrate is glucose. In one embodiment, the reactions catalyzed by the first and second enzymes in the detection complex lead to immobilization of the labeled Amplex Red or luminol on the surface, and optionally, the method can include measuring the labeled Amplex Red or luminol on the surface. The labeled Amplex Red or luminol is optionally biotin-Amplex Red or luminol, and the method can include adding labeled streptavidin and measuring the labels on the streptavidin.

Step (d) of embodiment (16) may include measuring a proximity-dependent signal that is generated when the first and second detectable labels are bound to the same analyte molecule and counting the number of reaction vessels that produce the proximity-dependent signal, e.g., the proximity-dependent signal is generated by PLA-RCA. For example, the first detectable label can be a FRET donor and the detectable label is a FRET acceptor and the proximity-dependent signal is measured by exciting the FRET donor and measuring emission from the FRET acceptor. In one example, the first and second detectable labels can be measured independently. Optionally, the first and second detectable labels are luminescent labels that differ from one another with respect to spectral properties. In one example, the first detectable label is a first enzyme that reacts with a first substrate to produce a first signal and the second detectable label is a second enzyme that reacts with a second substrate to produce a different second signal, and step (d) of embodiment (16) can include adding the first enzyme substrate and the second enzyme substrate and counting the number of reaction vessels in which the first and second signals are generated. The first and second signals can be changes in optical absorbance with different spectral properties. Optionally, first and second signals are luminescent signals with different spectral properties. The first and second enzymes can be hydrolytic enzymes, e.g., selected from a phosphatase, sulfatase, galactosidase, glucuronidase, or combinations thereof, and the first and second substrates are selected from phosphate, sulfate, galactoside and glucuronide modified stabilized dioxetanes, 4-methylumbelliferyl, fluorescein, or combinations thereof. In a specific example, the first and second enzymes are selected from horseradish peroxidase, beta-galactosidase, and alkaline phosphatase. The detection step of embodiment (16) can include detection via light scattering, optical absorbance, fluorescence, chemiluminescence, electrochemiluminescence, luminescence, radioactivity, magnetic field, or combinations thereof.

Embodiment (17): a kit for the detection of analytes in a sample, the kit comprising, in one or more vials, containers, or compartments: (a) a first detection reagent comprising a first detectable label; (b) a second detection reagent comprising a second detectable label; (c) a plurality of reaction vessels configured to contain one or fewer analyte molecules.

Embodiment (18): a kit for the detection of analytes in a sample, the kit comprising, in one or more vials, containers, or compartments: (a) a first detection reagent comprising a first detectable label; (b) a second detection reagent comprising a second detectable label; (c) a surface comprising a capture reagent; and (d) a plurality of reaction vessels configured to contain one or fewer analyte molecules.

The first and second detection reagents of embodiments (17) and (18) can comprise an antibody, antigen, ligand, receptor, oligonucleotide, hapten, epitope, mimitope, aptamer, or combinations thereof. In one example, the first and second detection reagents comprise an antibody. The capture antibody can comprise an antibody, antigen, ligand, receptor, oligonucleotide, hapten, epitope, mimitope, or aptamer, e.g., the capture antibody can include an antibody. In one example, the capture reagent can include a targeting moiety and the surface can include a targeting moiety complement, e.g., the targeting moiety and the targeting agent binding partner are selected from the following binding pairs: avidin-biotin, streptavidin-biotin, receptor-ligand, antibody-antigen, nucleic acid-nucleic acid complement.

The surface of embodiments (17) and (18) can be a particle, and for example, the capture reagents are immobilized on a plurality of particles. Alternatively, the surface is a location within one of the reaction vessels and e.g., the capture reagents are immobilized on surfaces of the plurality of reaction vessels. Optionally, the reaction vessels have surfaces with targeting moieties immobilized thereon and the capture reagents comprise targeting moiety complements. The plurality of reaction vessels can comprise an array of nanowells or water droplets dispersed in a water-in-oil emulsion. The plurality of reaction vessels can include at least 10,000 reaction vessels and optionally, a reaction vessel in the plurality has a volume of less than 100 nL.

In the kit of embodiments (17) and (18), the first detectable label can be a first enzyme of a coupled enzyme reaction system and the second detectable label is a second enzyme of the couple enzyme reaction system and the kit can include, in one or more additional vials, containers, or compartments, one or more substrates of the reaction system. For example, the first enzyme is an oxidase, the second enzyme is a peroxidase, and the substrates comprise an oxidase substrate and a labeled Amplex Red or luminol derivative. In a specific embodiment, the oxidase is glucose oxidase and the oxidase substrate is glucose. The first and second detectable labels can be components of a proximity-dependent system, e.g., the first detectable label is a FRET donor and the detectable label is a FRET acceptor. The first and second detectable labels can be measured independently. Optionally, the first and second detectable labels are luminescent labels that differ from one another with respect to spectral properties.

In the kit of embodiments (17) and (18), the first detectable label is a first enzyme that reacts with a first substrate to produce a first signal and the second detectable label is a second enzyme that reacts with a second substrate to produce a different second signal, and the kit can include, in one or more vials, containers, or compartments, the first enzyme substrate and the second enzyme substrate. Optionally, the first and second signals are changes in optical absorbance with different spectral properties. In one example, the first and second signals are luminescent signals with different spectral properties. The first and second enzymes can be hydrolytic enzymes. In one example, the first and second enzymes are selected from a phosphatase, sulfatase, galactosidase, glucuronidase, or combinations thereof. The first and second substrates can be selected from phosphate, sulfate, galactoside and glucuronide modified stabilized dioxetanes, 4-methylumbelliferyl, fluorescein, or combinations thereof. Optionally, the first and second enzymes are selected from horseradish peroxidase, beta-galactosidase, and alkaline phosphatase.

Embodiment (19): a method of detecting an analyte of interest in a sample comprising: (a) binding the analyte to a capture reagent, a first detection reagent having a first detectable label and a second detection reagent having a second detectable label and forming a complex, wherein the capture reagent in the complex is immobilized on a surface; (b) cross-linking the first and second detection reagent to form a cross-linked product; (c) releasing the cross-linked product from the surface into an eluent; (d) counting individual cross-linked products in the eluent that comprise both the first and second detectable labels. In this example (19), the capture reagent is an antibody, antigen, ligand, receptor, oligonucleotide, hapten, epitope, mimitope, or an aptamer, and in a specific example, the capture reagent is an antibody. Likewise, the first detection reagent can be an antibody, antigen, ligand, receptor, oligonucleotide, hapten, epitope, mimitope, or an aptamer, and in a specific example, the first detection reagent is an antibody. Moreover, the second detection reagent is an antibody, antigen, ligand, receptor, oligonucleotide, hapten, epitope, mimitope, or an aptamer, and specifically, the second detection reagent can be an antibody. In one particular example, the capture reagent and the first and second detection reagents are antibodies to the analyte.

Embodiment (19) can further comprise adding a cross-linking agent to cross-link the first and second detection reagents, e.g., the first and second detection reagents comprise reactive moieties and the cross-linking agent is a multifunctional cross-linking agent that links to the reactive moieties. For example, the reactive moieties comprise an amine, thiol, hydrazide, aldehyde, ester, iodoacetamide, maleimide, click chemistry reagents, and combinations thereof. The cross-linking agents can comprise an amine, thiol, hydrazide, aldehyde, ester, iodoacetamide, maleimide, click chemistry reagents, and combinations thereof. The first and second detection reagents can include binding moieties and the cross-linking agent is a multivalent binding partner of the binding moieties. In one example, the first and second detection reagents are antibodies of an animal species and the cross-linking agent is a multivalent anti-species antibody targeting antibodies of the animal species. The first and second detection reagents can comprise biotin and the cross-linking agent is streptavidin; the first and second detection reagents include streptavidin and the cross-linking agent is biotin; the first and second detection reagents are linked to streptavidin and the cross-linking agent is a polymer comprising a plurality of biotin molecules; and/or the first and second detection reagents comprise first and second nucleic acid probes, respectively, and the cross-linking agent is an oligonucleotide that can include a sequence complementary to the first nucleic acid probe and a separate sequence complementary to the second nucleic acid probe.

The surface of embodiment (19) can comprise a particle, a reaction vessel, e.g., a tube or ampoule, and/or the surface can include a well of a multi-well plate. The method of embodiment (19) can further include collecting the particles and washing the particles to remove impurities and optionally, the first and second detectable labels are measured by a measurement of light scattering, optical absorbance, fluorescence, chemiluminescence, electrochemiluminescence, bioluminescence, phosphorescence, radioactivity, magnetic field, or combinations thereof. In a specific example, the first and second detectable labels comprise an ECL label and the counting step can include measuring an ECL signal.

Embodiment (20): a kit for the detection of an analyte of interest in a sample comprising, in one or more vials, containers, or compartments: (a) a surface comprising an immobilized capture reagent; (b) a first detection reagent having a first detectable label; (c) a second detection reagent having a second detectable label; and (d) a cross-linking agent reactive with the first and second detection reagents.

The first and second detection reagents of embodiment (20) can comprise reactive moieties and the cross-linking agent is a multifunctional cross-linking agent that links to the reactive moieties. The reactive moieties can include an amine, thiol, hydrazide, aldehyde, ester, iodoacetamide, maleimide, click chemistry reagents, and combinations thereof and the cross-linking agents can include an amine, thiol, hydrazide, aldehyde, ester, iodoacetamide, maleimide, click chemistry reagents, and combinations thereof. The first and second detection reagents of embodiment (20) can comprise binding moieties and the cross-linking agent is a multivalent binding partner of the binding moieties, e.g., the first and second detection reagents are antibodies of an animal species and the cross-linking agent is a multivalent anti-species antibody targeting antibodies of the animal species; the first and second detection reagents comprise biotin and the cross-linking agent is streptavidin; the first and second detection reagents comprise streptavidin and the cross-linking agent is biotin; the first and second detection reagents are linked to streptavidin and the cross-linking agent is a polymer comprising a plurality of biotin molecules; and/or the first and second detection reagents comprise first and second nucleic acid probes, respectively, and the cross-linking agent is an oligonucleotide that can include a sequence complementary to the first nucleic acid probe and a separate sequence complementary to the second nucleic acid probe.

The surface of embodiment (20) can include a particle, a well of a multi-well plate, or a reaction vessel, e.g., a tube or ampoule. In addition, the surface can include a plurality of distinct binding domains and the capture reagent is located on a distinct binding domain on the surface. If the surface is a well, the well can include a plurality of distinct binding domains and the capture reagent is located on a distinct binding domain within the well. The surface can also include an electrode.

Embodiment (21): a method of detecting an analyte of interest in a sample comprising: (a) binding the analyte to a capture reagent, a first detection reagent and a second detection reagent to form a complex, wherein the first detection reagent can include a first detectable label and a first nucleic acid probe, the second detection reagent can include a second detectable label and a second nucleic acid probe, and the capture reagent in the complex is immobilized on a surface; (b) cross-linking the first and second detection reagent by (i) hybridizing the first probe to the second probe, (ii) hybridizing the first and second probes to a third nucleic acid having regions complementary to the first and second probes, or (iii) ligating the first and second probes; (c) releasing the cross-linked product from the surface into an eluent; (d) counting individual cross-linked products in the eluent that comprise both the first and second detectable labels.

The capture reagent of embodiment (21) can be an antibody, antigen, ligand, receptor, oligonucleotide, hapten, epitope, mimitope, or an aptamer, e.g., the capture reagent is an antibody. Likewise, the first detection reagent is an antibody, antigen, ligand, receptor, oligonucleotide, hapten, epitope, mimitope, or an aptamer, e.g., the first detection reagent is an antibody; the second detection reagent can be an antibody, antigen, ligand, receptor, oligonucleotide, hapten, epitope, mimitope, or an aptamer, e.g., the second detection reagent is an antibody. In a specific example, the capture reagent and the first and second detection reagents are antibodies to the analyte.

The surface of embodiment (21) can include a particle, a reaction vessel, e.g., a tube or ampoule, or a well of a multi-well plate. The method of embodiment (21) can further comprise collecting the particles and washing the particles to remove impurities. The first and second detectable labels can be measured by a measurement of light scattering, optical absorbance, fluorescence, chemiluminescence, electrochemiluminescence, bioluminescence, phosphorescence, radioactivity, magnetic field, or combinations thereof. In a specific example, the first and second detectable labels comprise an ECL label and the counting step can include measuring an ECL signal.

Embodiment (22): a kit for the detection of an analyte of interest in a sample comprising, in one or more vials, containers, or compartments: (a) a surface comprising an immobilized capture reagent; (b) a first detection reagent having a first detectable label and a first nucleic acid probe; (c) a second detection reagent having a second detectable label and a second nucleic acid probe; and (d) a third nucleic acid having regions complementary to the first and second nucleic acid probes.

The surface of embodiment (22) can include a particle, a well of a multi-well plate, or a reaction vessel, e.g., a tube or ampoule. The surface can include a plurality of distinct binding domains and the capture reagent is located on a distinct binding domain on the surface, and if the surface is a well, the well can comprise a plurality of distinct binding domains and the capture reagent is located on a distinct binding domain within the well. The surface optionally can include an electrode.

Embodiment (23): a method of detecting an analyte of interest in a sample comprising: (a) binding the analyte to a capture reagent, a first detection reagent and a second detection reagent to form a complex, wherein the first detection reagent can include a first nucleic acid probe, the second detection reagent can include a second nucleic acid probe, and the capture reagent in the complex is immobilized on a surface; (b) extending the second nucleic acid probe to form an extended sequence comprising a detectable label, the extension being dependent on the co-localization of the first and second nucleic acid probes in the complex; (c) releasing the extended sequence from the surface into an eluent; and (d) counting individual extended sequences in the eluent. In this embodiment, the capture reagent is an antibody, antigen, ligand, receptor, oligonucleotide, hapten, epitope, mimitope, or an aptamer. In a specific example, the capture reagent is an antibody. Likewise, the first detection reagent is an antibody, antigen, ligand, receptor, oligonucleotide, hapten, epitope, mimitope, or an aptamer, and in a specific example, the first detection reagent is an antibody. The second detection reagent is an antibody, antigen, ligand, receptor, oligonucleotide, hapten, epitope, mimitope, or an aptamer, and specifically, the second detection reagent is an antibody. In a specific example, the capture reagent and the first and second detection reagents are antibodies to the analyte.

The surface of embodiment (23) can include a particle, a reaction vessel, e.g., a tube or ampoule; or a well of a multi-well plate. The method of embodiment (23) can further comprise collecting the particles and washing the particles to remove impurities.

The label of embodiment (23) can be measured by a measurement of light scattering, optical absorbance, fluorescence, chemiluminescence, electrochemiluminescence, bioluminescence, phosphorescence, radioactivity, magnetic field, or combinations thereof. In a specific example, the label can include an ECL label and the counting step can include measuring an ECL signal.

The extending step of embodiment (23) can include binding the probe to a template nucleic acid sequence and extending the probe by polymerase chain reaction. The extending step can also comprise binding the first probe to a template nucleic acid sequence, forming a circular nucleic acid template, and extending the circular template by rolling circle amplification. The extending step may comprise binding the first probe to a template nucleic acid sequence, binding the second probe to the template sequence, and ligating the first and second probes. Optionally, the label is a fluorescent label and the counting of individual extended sequences can include single molecule fluorescence detection, e.g., can include fluorescence correlation spectroscopy and/or fluorescence cross-correlation spectroscopy. Single molecule fluorescence detection can comprise flowing the eluent through a capillary, focusing a light source on a volume within the capillary to create an interrogation zone and observing the interrogation zone with a light detector to detect the passage of fluorescent molecules through the interrogation zone. Single molecule fluorescence detection can also comprise flowing the eluent through a capillary, focusing a light source on a volume within the capillary to create an interrogation zone and observing the interrogation zone with a light detector to detect the passage of fluorescent molecules through the interrogation zone.

Embodiment (24): method of detecting an analyte of interest in a sample comprising: (a) binding the analyte to a capture reagent, a first detection reagent having a first detectable label and a second detection reagent having a second detectable label and forming a complex, wherein the capture reagent in the complex is immobilized on a surface; (b) releasing the formed complex from the surface, by dissociating the immobilized capture reagent from surface into an eluent; and (c) counting individual products in the eluent that comprise both the first and second detectable labels. In this embodiment, the capture reagent is an antibody, antigen, ligand, receptor, oligonucleotide, hapten, epitope, mimitope, or an aptamer, e.g., the capture reagent is an antibody; the first detection reagent is an antibody, antigen, ligand, receptor, oligonucleotide, hapten, epitope, mimitope, or an aptamer, e.g., the first detection reagent is an antibody; the second detection reagent is an antibody, antigen, ligand, receptor, oligonucleotide, hapten, epitope, mimitope, or an aptamer, e.g., the second detection reagent is an antibody; and in a specific example, the capture reagent and the first and second detection reagents are antibodies to the analyte.

The surface of embodiment (24) can comprise a particle, a reaction vessel, e.g., a tube or ampoule, and/or a well of a multi-well plate. The method of embodiment (24) can include collecting the particles and washing the particles to remove impurities. The first and second detectable labels can be measured by a measurement of light scattering, optical absorbance, fluorescence, chemiluminescence, electrochemiluminescence, bioluminescence, phosphorescence, radioactivity, magnetic field, or combinations thereof, and in a specific embodiment, the first and second detectable labels comprise an ECL label and the counting step can include measuring an ECL signal.

Embodiment (25): a method of detecting an analyte of interest in a sample comprising: (a) binding the analyte to: (i) a capture reagent on a surface comprising the capture reagent for the analyte; (ii) a first detection reagent for the analyte that is linked to a first nucleic acid probe; and (iii) a second detection reagent for the analyte that is linked to a second nucleic acid probe; thereby forming a complex on the surface comprising the binding reagent, the analyte and the first and second detection reagents; (b) using an extension process that requires the first and second probes to be in proximity, extending the second probe to form an extended sequence; and (c) measuring the amount of extended sequence bound to the surface. In this embodiment, the capture reagent is an antibody, antigen, ligand, receptor, oligonucleotide, hapten, epitope, mimitope, or an aptamer, e.g., the capture reagent is an antibody; the first detection reagent is an antibody, antigen, ligand, receptor, oligonucleotide, hapten, epitope, mimitope, or an aptamer, e.g., the first detection reagent is an antibody; the second detection reagent is an antibody, antigen, ligand, receptor, oligonucleotide, hapten, epitope, mimitope, or an aptamer; e.g., the second detection reagent is an antibody; and in a specific example, the capture reagent and the first and second detection reagents are antibodies to the analyte.

The extended sequence of embodiment (25) can include one or more detection sequences and the measuring step can include contacting the extended sequence with a plurality of labeled probes complementary to the one or more detection sequences; the extended sequence can include one or more modified bases and the measuring step can include contacting the extended sequence with a plurality of detectable moieties capable of binding to the one or more modified bases; and/or the extended sequence can include one or more labeled bases and the measuring step can include detecting the presence of the one or more labeled bases. The one or more modified bases comprise an aptamer, aptamer ligand, antibody, antigen, ligand, receptor, hapten, epitope, or a mimetope and the plurality of detectable moieties each comprise a binding partner of the one or more modified bases and a detectable label. The one or more modified bases can include streptavidin and the plurality of detectable moieties each comprise biotin and a detectable label; the one or more modified bases comprise biotin and the plurality of detectable moieties each comprise streptavidin and a detectable label; the one or more modified bases comprise avidin and the plurality of detectable moieties each comprise biotin and a detectable label; and/or the one or more modified bases comprise biotin and the plurality of detectable moieties each comprise avidin and a detectable label.

Step (a) of embodiment (25) can include binding the analyte to the following species in the following order: (i) the capture reagent on a surface; and (ii) the detection reagent for the analyte; binding the analyte to the following species in the following order: (i) the detection reagent for the analyte; and (ii) the capture reagent on the surface; or binding the analyte to the following species simultaneously or substantially simultaneously: (i) the capture reagent on a surface; and (ii) the detection reagent for the analyte. The extending step can include binding the probe to a template nucleic acid sequence and extending the probe by polymerase chain reaction; or binding the probe to a template nucleic acid sequence, forming a circular nucleic acid template, and extending the circular template by rolling circle amplification. In this embodiment, the extended probe can remain localized on the surface following probe extension, e.g., the complex remains bound to the surface after the extending step. The extending step can include PCR (Polymerase Chain Reaction), LCR (Ligase Chain Reaction), SDA (Strand Displacement Amplification), 3SR (Self-Sustained Synthetic Reaction), or isothermal amplification methods. In a specific example, the extending step can include isothermal amplification methods, e.g., helicase-dependent amplification or rolling circle amplification (RCA).

The extension process of embodiment (25) can comprise contacting the complex formed in step (a) with a connector sequence comprising (i) an interior sequence complementary to the second probe and (ii) two end sequences complementary to non-overlapping regions of the first probe. The process can further comprise ligating the two end sequences of the connector oligonucleotide to form a circular target sequence that is hybridized to both the first and second probes. The extension process of embodiment (25) can also include contacting the complex formed in step (a) with a first connector oligonucleotide sequence including a first connector probe sequence complementary to a first region of the first probe and a first region on the second probe, and a second connector oligonucleotide comprising a second probe sequence complementary to a second non-overlapping region of the first probe and a second non-overlapping region of the second probe. The process can also include ligating the first and second connector oligonucleotides to form a circular target sequence that is hybridized to both the first and second probes.

The surface of embodiment (25) can comprise a particle or a well of a multi-well plate. The surface can include a plurality of distinct binding domains and the capture reagent(s) are located on two distinct binding domains on the surface. If the surface is a well, the well can include a plurality of distinct binding domains and the capture reagent(s) are located on two distinct binding domains within the well. The surface can include a plurality of distinct binding domains and the capture reagent(s) are located on the same binding domain on the surface, and if the surface is a well, the well can comprise a plurality of distinct binding domains and the capture reagent(s) are located on the same binding domain within the well. The surface can include an electrode and the measuring step can include applying a voltage waveform to the electrode to generate an electrochemiluminesce signal. The method optionally includes collecting the particle on an electrode and applying a voltage waveform to the electrode to generate an electrochemiluminescence signal. The measuring step may further comprise binding the extended sequence to a detection probe having a detectable label, measuring the detectable label and correlating the measurement to the amount of analyte in the sample, wherein the detection probe comprising a nucleic acid sequence that is complementary to a region of the extended sequence. The detectable label can be measured by a measurement of light scattering, optical absorbance, fluorescence, chemiluminescence, electrochemiluminescence, bioluminescence, phosphorescence, radioactivity, magnetic field, or combinations thereof. In a specific example, the detectable label is an ECL label and the measuring step can include measuring an ECL signal.

Embodiment (26): a kit for the detection of an analyte of interest in a sample comprising, in one or more vials, containers, or compartments: (a) a surface comprising a capture reagent for the analyte; (b) a first detection reagent for the analyte that is linked to a first nucleic acid probe; and (c) a second detection reagent for the analyte that is linked to a second nucleic acid probe.

The capture reagent of embodiment (26) can include an antibody, antigen, ligand, receptor, oligonucleotide, hapten, epitope, mimitope, or aptamer, e.g., the capture reagent can include an antibody; the first detection reagent can include an antibody, antigen, ligand, receptor, oligonucleotide, hapten, epitope, mimitope, or aptamer, e.g., the first detection reagent can include an antibody; the second detection reagent can include an antibody, antigen, ligand, receptor, oligonucleotide, hapten, epitope, mimitope, or aptamer, e.g., the second detection reagent can include an antibody; and the surface can include a particle and/or a well of a multi-well plate. The surface can include a plurality of distinct binding domains and the capture reagent(s) are located on two distinct binding domains on the surface; and if the surface is a well, the well can comprise a plurality of distinct binding domains and the capture reagent(s) are located on two distinct binding domains within the well. Optionally, the surface can include a plurality of distinct binding domains and the capture reagent(s) are located on the same binding domain on the surface, and if the surface is a well, the well can include a plurality of distinct binding domains and the capture reagent(s) are located on the same binding domain within the well. The surface can comprise an electrode.

The surface of embodiments 1-26 can include an interior surface of an assay container, e.g., a test tube, cuvette, flow cell, FACS cell sorter, cartridge, or a well of a multi-well plate. The surface can also comprise a slide, assay chips, or assay array; a pin, probe, bead, or filtration media; lateral flow media, e.g., a filtration membrane.

Embodiment (27): a method of detecting an analyte of interest in a sample comprising one or more analyte molecules, the method comprising: (a) contacting the sample with a surface comprising a plurality of resolvable binding regions positioned on the surface, each resolvable binding region comprising a plurality of capture reagents for one or more analyte molecules in the sample; (b) binding one or more analyte molecules to (i) one or more capture reagents on the surface; (ii) a first detection reagent for the analyte comprising a first detectable label, and (iii) a second detection reagent for the analyte comprising a second detectable label; thereby forming a detection complex on a resolvable binding domain on the surface comprising the capture reagent, the analyte and the first and second detection reagents, wherein the first and second detectable labels are different label compounds; (c) determining the presence or absence of the analyte molecule in each binding region; and (d) identifying the number of binding regions that contain the analyte molecule and/or the number of binding regions that do not contain the analyte molecule. The identifying step can include imaging an optical signal from the surface to generate an image comprising a plurality of pixels and each resolvable binding region maps to one or more pixels in the image. The resolvable binding regions can be elements of an array and/or configured to isolate individual particles. Each resolvable binding region can be an individual nano-wells having a volume<100 nL and/or at least 99% of the binding regions contain either zero or one analyte molecule; at least about 95% of the binding regions contain either zero or one analyte molecule; at least about 80% of the binding regions contain either zero or one analyte molecule; or at least about 50% of the binding regions contain either zero or one analyte molecule. The concentration of analyte molecules in the sample can be determined at least in part using a calibration curve, a Poisson distribution analysis and/or a Gaussian distribution analysis of the number of binding regions that contain at least one or one analyte molecule.

The surface of embodiment (27) can include a plurality of particles each comprising a plurality of capture reagents for an analyte molecule wherein the plurality of particles is distributed across a plurality of resolvable binding regions, and the method can include: (i) binding the one or more analyte molecules to one or more capture reagents on the surface, and first and second detection reagents for each of the one or more analyte molecules, wherein the first and second detection reagents include first and second detectable labels, respectively; (ii) distributing the plurality of particles across an array of resolvable binding regions; and (iii) determining the presence or absence of an analyte molecule in each resolvable binding regions, so as to identify the number of binding regions that contain an analyte molecule and/or the number of binding regions that do not contain an analyte molecule, wherein optionally, each resolvable binding region is an individual nano-wells having a volume<100 nL, and/or at least 99% of the binding regions contain either zero or one analyte molecule; at least about 95% of the binding regions contain either zero or one analyte molecule; at least about 80% of the binding regions contain either zero or one analyte molecule; and/or at least about 50% of the binding regions contain either zero or one analyte molecule.

The capture reagent in embodiment (27) is an antibody, antigen, ligand, receptor, oligonucleotide, hapten, epitope, mimitope, or an aptamer, e.g., the capture reagent is an antibody; the first detection reagent is an antibody, antigen, ligand, receptor, oligonucleotide, hapten, epitope, mimitope, or an aptamer, e.g., the first detection reagent is an antibody; the second detection reagent is an antibody, antigen, ligand, receptor, oligonucleotide, hapten, epitope, mimitope, or an aptamer, e.g., the second detection reagent is an antibody. In a specific example, the capture reagent and the first and second detection reagents are antibodies to the analyte.

Step (a) of embodiment (27) can include binding the analyte to the following species in the following order: (i) the capture reagent on a surface; and (ii) the first and second detection reagents for the analyte; binding the analyte to the following species in the following order: (i) the first and second detection reagents for the analyte; and (ii) the capture reagent on the surface; or binding the analyte to the following species simultaneously or substantially simultaneously: (i) the capture reagent on a surface; and (ii) the first and second detection reagents for the analyte.

The surface of embodiment (27) can include a particle or a well of a multi-well plate. In a specific example, the surface can include an electrode and the identifying step can include applying a voltage waveform to the electrode to generate an electrochemiluminesce signal. The method of embodiment (27) can further include collecting the particle on an electrode and applying a voltage waveform to the electrode to generate an electrochemilumin-escence signal. The first detectable label is measured by a measurement of light scattering, optical absorbance, fluorescence, chemiluminescence, electrochemiluminescence, bioluminescence, phosphorescence, radioactivity, magnetic field, or combinations thereof and/or the second detectable label is measured by a measurement of light scattering, optical absorbance, fluorescence, chemiluminescence, electrochemiluminescence, bioluminescence, phosphorescence, radioactivity, magnetic field, or combinations thereof. The first and second detectable labels can be measured independently, and in one example, the first and second detectable labels are luminescent labels that differ from one another with respect to spectral properties.

The surface of embodiment (27) can include an interior surface of an assay container, e.g., a test tube, cuvette, flow cell, FACS cell sorter, cartridge, or a well of a multi-well plate. The surface can also comprise a slide, assay chips, or assay array; a pin, probe, bead, or filtration media; lateral flow media, e.g., a filtration membrane.

Embodiment (28): a kit for the detection of an analyte of interest in a sample comprising one or more analyte molecules, the kit comprising: (a) a surface comprising a plurality of resolvable binding regions positioned on the surface, each resolvable binding region comprising a plurality of capture reagents for one or more analyte molecules in the sample; (b) a first detection reagent for the analyte comprising a first detectable label, and (c) a second detection reagent for the analyte comprising a second detectable label; wherein the first and second detectable labels are different label compounds.

The resolvable binding regions of embodiment (28) can be elements of an array and/or configured to isolate individual particles. Each resolvable binding region is optionally, an individual nano-wells having a volume<100 nL. The surface can include a plurality of particles each comprising a plurality of capture reagents for an analyte molecule wherein the plurality of particles is distributed across a plurality of resolvable binding regions, and the kit can include: first and second detection reagents for each of the one or more analyte molecules, wherein the first and second detection reagents include first and second detectable labels, respectively.

The capture reagent in embodiment (28) is an antibody, antigen, ligand, receptor, oligonucleotide, hapten, epitope, mimitope, or an aptamer, e.g., the capture reagent is an antibody; the first detection reagent is an antibody, antigen, ligand, receptor, oligonucleotide, hapten, epitope, mimitope, or an aptamer, e.g., the first detection reagent is an antibody; the second detection reagent is an antibody, antigen, ligand, receptor, oligonucleotide, hapten, epitope, mimitope, or an aptamer, e.g., the second detection reagent is an antibody. In a specific example, the capture reagent and the first and second detection reagents are antibodies to the analyte.

The surface of embodiment (28) can include a particle or a well of a multi-well plate. In a specific example, the surface can include an electrode and the identifying step can include applying a voltage waveform to the electrode to generate an electrochemiluminesce signal. The first detectable label is measured by a measurement of light scattering, optical absorbance, fluorescence, chemiluminescence, electrochemiluminescence, bioluminescence, phosphorescence, radioactivity, magnetic field, or combinations thereof and/or the second detectable label is measured by a measurement of light scattering, optical absorbance, fluorescence, chemiluminescence, electrochemiluminescence, bioluminescence, phosphorescence, radioactivity, magnetic field, or combinations thereof. The first and second detectable labels can be measured independently, and in one example, the first and second detectable labels are luminescent labels that differ from one another with respect to spectral properties.

The surface of embodiment (28) can include an interior surface of an assay container, e.g., a test tube, cuvette, flow cell, FACS cell sorter, cartridge, or a well of a multi-well plate. The surface can also comprise a slide, assay chips, or assay array; a pin, probe, bead, or filtration media; lateral flow media, e.g., a filtration membrane.

Embodiment (29): a method of detecting HIV p24 in a sample comprising: (a) binding HIV p24 to: (i) a capture reagent on a surface comprising the capture reagent for HIV p24, and an anchoring reagent comprising an anchoring oligonucleotide sequence; (ii) a first detection reagent for HIV p24 that is linked to a first nucleic acid probe; and (iii) a second detection reagent for HIV p24 that is linked to a second nucleic acid probe; thereby forming a complex on the surface comprising the binding reagent, HIV p24 and the first and second detection reagents; (b) using an extension process that requires the first and second probes to be in proximity, extending the second probe to form an extended sequence comprising an anchoring sequence complement that is complementary to the anchoring sequence; (c) hybridizing the anchoring sequence to the anchoring sequence complement; and (d) measuring the amount of extended sequence bound to the surface.

The capture reagent of embodiment (29) can be an antibody, antigen, ligand, receptor, oligonucleotide, hapten, epitope, mimitope, or an aptamer. In a specific example, the capture reagent is an antibody. Likewise, the first detection reagent is an antibody, antigen, ligand, receptor, oligonucleotide, hapten, epitope, mimitope, or an aptamer, and in a particular example, the first detection reagent is an antibody. The second detection reagent can be an antibody, antigen, ligand, receptor, oligonucleotide, hapten, epitope, mimitope, or an aptamer, and in a particular example, the second detection reagent is an antibody. More particularly, the capture reagent and the first and second detection reagents are antibodies to HIV p24.

In embodiment (29), the anchoring oligonucleotide sequence can include a single stranded oligonucleotide sequence or a double stranded oligonucleotide sequence. In this embodiment, the extended sequence can include one or more detection sequences and the measuring step can include contacting the extended sequence with a plurality of labeled probes complementary to the one or more detection sequences. The extended sequence can also include one or more modified bases and the measuring step can include contacting the extended sequence with a plurality of detectable moieties capable of binding to the one or more modified bases. The extended sequence can further comprise one or more labeled bases and the measuring step can include detecting the presence of the one or more labeled bases. The one or more modified bases can comprise an aptamer, aptamer ligand, antibody, antigen, ligand, receptor, hapten, epitope, or a mimetope and the plurality of detectable moieties each comprise a binding partner of the one or more modified bases and a detectable label. For example, the one or more modified bases comprise streptavidin and the plurality of detectable moieties each comprise biotin and a detectable label; the one or more modified bases comprise biotin and the plurality of detectable moieties each comprise streptavidin and a detectable label; the one or more modified bases comprise avidin and the plurality of detectable moieties each comprise biotin and a detectable label; and/or the one or more modified bases comprise biotin and the plurality of detectable moieties each comprise avidin and a detectable label.

Step (a) of embodiment (29) can include binding HIV p24 to the following species in the following order: (i) the capture reagent on a surface; and (ii) the detection reagent for HIV p24. Alternatively, step (a) can include binding HIV p24 to the following species in the following order: (i) the detection reagent for HIV p24; and (ii) the capture reagent on the surface; or step (a) can include binding HIV p24 to the following species simultaneously or substantially simultaneously: (i) the capture reagent on a surface; and (ii) the detection reagent for HIV p24.

The extending step of embodiment (29) can include binding the probe to a template nucleic acid sequence and extending the probe by polymerase chain reaction. The extending step can further include binding the probe to a template nucleic acid sequence, forming a circular nucleic acid template, and extending the circular template by rolling circle amplification. The extended probe can remain localized on the surface following probe extension, e.g., the complex remains bound to the surface after the extending step. The extended probe can be bound to the anchoring reagent at a position within 10-100 um of the location of the complex on the surface. In one specific embodiment, the extended probe is bound to the anchoring reagent at a position less than 100 um, less than 50 um, or more particularly, less than 10 um from the location of the complex on the surface. The extending step can include PCR (Polymerase Chain Reaction), LCR (Ligase Chain Reaction), SDA (Strand Displacement Amplification), 3SR (Self-Sustained Synthetic Reaction), or isothermal amplification methods. In a particular example, the extending step can include isothermal amplification methods, e.g., is helicase-dependent amplification or rolling circle amplification (RCA).

The extension process of embodiment (29) can include contacting the complex formed in step (a) with a connector sequence comprising (i) an interior sequence complementary to the second probe and (ii) two end sequences complementary to non-overlapping regions of the first probe. The method can further include ligating the two end sequences of the connector oligonucleotide to form a circular target sequence that is hybridized to both the first and second probes. Alternatively, the extension process can include contacting the complex formed in step (a) of embodiment (29) with a first connector oligonucleotide sequence including a first connector probe sequence complementary to a first region of the first probe and a first region on the second probe, and a second connector oligonucleotide comprising a second probe sequence complementary to a second non-overlapping region of the first probe and a second non-overlapping region of the second probe; and optionally, ligating the first and second connector oligonucleotides to form a circular target sequence that is hybridized to both the first and second probes.

The surface of embodiment (29) can include a particle and/or a well of a multi-well plate. The surface can include a plurality of distinct binding domains and the capture reagent and the anchoring reagent are located on two distinct binding domains on the surface. If the surface is a well of a plate, the well can include a plurality of distinct binding domains and the capture reagent and the anchoring reagent are located on two distinct binding domains within the well. The surface can also include a plurality of distinct binding domains and the capture reagent and the anchoring reagent are located on the same binding domain on the surface. If the surface is a well of a plate, the well can include a plurality of distinct binding domains and the capture reagent and the anchoring reagent are located on the same binding domain within the well. The capture reagent and the anchoring reagent can be within 10-100 nm on the surface. In a specific example, the surface can include an electrode and the measuring step can include applying a voltage waveform to the electrode to generate an electrochemiluminesce signal, and optionally, the method of embodiment (29) further includes collecting the particle on an electrode and applying a voltage waveform to the electrode to generate an electrochemiluminescence signal.

The measuring step of embodiment (29) can include binding the extended sequence to a detection probe having a detectable label, measuring the detectable label and correlating the measurement to the amount of p24 in the sample, wherein the detection probe comprising a nucleic acid sequence that is complementary to a region of the extended sequence. The detectable label can be measured by a measurement of light scattering, optical absorbance, fluorescence, chemiluminescence, electrochemiluminescence, bioluminescence, phosphorescence, radioactivity, magnetic field, or combinations thereof. In a particular example, the detectable label is an ECL label and the measuring step can include measuring an ECL signal.

Embodiment (30): a kit for the detection of HIV p24 in a sample comprising, in one or more vials, containers, or compartments: (a) a surface comprising (i) a capture reagent for HIV p24, and (ii) an anchoring reagent comprising an anchoring oligonucleotide sequence; (b) a first detection reagent for HIV p24 that is linked to a first nucleic acid probe; and (c) a second detection reagent for HIV p24 that is linked to a second nucleic acid probe.

The capture reagent of embodiment (30) can include an antibody, antigen, ligand, receptor, oligonucleotide, hapten, epitope, mimitope, or aptamer, and in a specific example the capture reagent can include an antibody. Likewise, the first detection reagent can include an antibody, antigen, ligand, receptor, oligonucleotide, hapten, epitope, mimitope, or aptamer, and in a specific example, the first detection reagent can include an antibody. Similarly, the second detection reagent can include an antibody, antigen, ligand, receptor, oligonucleotide, hapten, epitope, mimitope, or aptamer, and in a specific example, the second detection reagent can include an antibody.

The surface of embodiment (30) can include a particle and/or a well of a multi-well plate. The surface can include a plurality of distinct binding domains and the capture reagent and the anchoring reagent are located on two distinct binding domains on the surface. If the surface is a well, the well can comprise a plurality of distinct binding domains and the capture reagent and the anchoring reagent are located on two distinct binding domains within the well. The surface can include a plurality of distinct binding domains and the capture reagent and the anchoring reagent are located on the same binding domain on the surface; and/or if the surface is a well, the well can include a plurality of distinct binding domains and the capture reagent and the anchoring reagent are located on the same binding domain within the well. The capture reagent and the anchoring reagent can be within 10-100 nm on the surface. In a specific example, the surface can include an electrode.

Embodiment (31): a method of detecting HIV p24 in a sample comprising: (a) binding HIV p24 to: (i) a capture reagent for HIV p24 on a surface comprising the capture reagent and an anchoring reagent; (ii) a first detection reagent for HIV p24 comprising a first proximity probe, and (iii) a second detection reagent for HIV p24 comprising a second proximity probe; thereby forming a detection complex on the surface comprising the capture reagent, HIV p24 and the first and second detection reagents; (b) contacting the detection complex formed in (c) with a connector sequence comprising (i) an interior sequence complementary to the second proximity probe and (ii) two end sequences complementary to non-overlapping regions of the first proximity probe; (c) hybridizing the connector sequence to the first and second proximity probes; (d) ligating the two end sequences of the connector oligonucleotide to form a circular target sequence that is hybridized to both the first and second proximity probes; (e) extending the second proximity probe by rolling circle amplification of the target sequence to generate an amplicon comprising a binding domain that binds the anchoring reagent; (f) binding the amplicon to the anchoring reagent; and (g) measuring the amount of amplicon on the surface.

Embodiment (32): a method of detecting HIV p24 in a sample comprising: (a) binding HIV p24 to: (i) a capture reagent for HIV p24 on a surface comprising the capture reagent and an anchoring reagent; (ii) a first detection reagent for HIV p24 comprising a first proximity probe, and (iii) a second detection reagent for HIV p24 comprising a second proximity probe; thereby forming a detection complex on the surface comprising the capture reagent, HIV p24 and the first and second detection reagents; (b) contacting the detection complex formed in (c) with a first connector oligonucleotide and a second connector oligonucleotide, wherein (i) a first end of the first connector and a first end of the second connector are complementary to two non-overlapping regions of the first proximity probe and (ii) a second end of the first connector and a second end of the second connector are complementary to two non-overlapping regions of the first proximity probe; (c) hybridizing the first and second connector oligonucleotides to the first and second proximity probes; (d) ligating the first and second connector oligonucleotides to form a circular target sequence that is hybridized to both the first and second proximity probes; (e) extending the second proximity probe by rolling circle amplification of the target sequence to generate an amplicon comprising a binding domain that binds the anchoring reagent; (f) binding the amplicon to the anchoring reagent; and (g) measuring the amount of amplicon on the surface.

The capture reagent of embodiments (31) and (32) is an antibody, antigen, ligand, receptor, oligonucleotide, hapten, epitope, mimitope, or an aptamer, and in a specific example, the capture reagent is an antibody. Similarly, the first detection reagent is an antibody, antigen, ligand, receptor, oligonucleotide, hapten, epitope, mimitope, or an aptamer, e.g., the first detection reagent is an antibody. In addition, the second detection reagent is an antibody, antigen, ligand, receptor, oligonucleotide, hapten, epitope, mimitope, or an aptamer, e.g., the second detection reagent is an antibody. In a specific example of embodiments (31) and (32), the capture reagent and the first and second detection reagents are antibodies to HIV p24.

The anchoring reagent of embodiments (31) and (32) can include an oligonucleotide sequence, aptamer, aptamer ligand, antibody, antigen, ligand, receptor, hapten, epitope, or a mimetope. In one example, the binding domain can include an aptamer and the anchoring reagent can include an aptamer ligand. The binding domain can include a nucleic acid sequence and the anchoring reagent can include a DNA-binding protein; and/or the anchoring reagent can include an oligonucleotide sequence and the amplicon can include a complementary oligonucleotide sequence.

The amplicon of embodiments (31) and (32) can include one or more detection sequences and the measuring step can include contacting the extended sequence with a plurality of labeled probes complementary to the one or more detection sequences. Moreover, the amplicon may further comprise one or more modified bases and the measuring step can include contacting the extended sequence with a plurality of detectable moieties capable of binding to the one or more modified bases. Still further, the amplicon may further include one or more labeled bases and the measuring step can include detecting the presence of the one or more labeled bases. The one or more modified bases can comprise an aptamer, aptamer ligand, antibody, antigen, ligand, receptor, hapten, epitope, or a mimetope and the plurality of detectable moieties each comprise a binding partner of the one or more modified bases and a detectable label. The one or more modified bases can comprise streptavidin and the plurality of detectable moieties each comprise biotin and a detectable label; the one or more modified bases can comprise biotin and the plurality of detectable moieties each comprise streptavidin and a detectable label; the one or more modified bases can comprise avidin and the plurality of detectable moieties each comprise biotin and a detectable label; and/or the one or more modified bases can comprise biotin and the plurality of detectable moieties each comprise avidin and a detectable label.

Step (a) of embodiments (31) and (32) can include binding HIV p24 to the following species in the following order: (i) the capture reagent on a surface; and (ii) the first and second detection reagents for HIV p24. Alternatively, step (a) can include binding HIV p24 to the following species in the following order: (i) the first and second detection reagents for HIV p24; and (ii) the capture reagent on the surface. Still further, step (a) can include binding HIV p24 to the following species simultaneously or substantially simultaneously: (i) the capture reagent on a surface; and (ii) the first and second detection reagents for HIV p24.

The amplicon of embodiments (31) and (32) remains localized on the surface following probe extension. The complex can remain bound to the surface after the extending step. For example, the amplicon is bound to the anchoring reagent at a position within 10-100 um of the location of the complex on the surface. In one specific embodiment, the extended probe is bound to the anchoring reagent at a position less than 100 um, less than 50 um, or more particularly, less than 10 um from the location of the complex on the surface.

The surface of embodiments (31) and (32) can include a particle and/or a well of a multi-well plate. The surface can include a plurality of distinct binding domains and the capture reagent and the anchoring reagent are located on two distinct binding domains on the surface. If the surface is a well of a plate, the well can comprise a plurality of distinct binding domains and the capture reagent and the anchoring reagent are located on two distinct binding domains within the well. The surface can include a plurality of distinct binding domains and the capture reagent and the anchoring reagent are located on the same binding domain on the surface. If the surface is a well of a plate, the well can include a plurality of distinct binding domains and the capture reagent and the anchoring reagent are located on the same binding domain within the well. In a specific example, the capture reagent and the anchoring reagent are within 10-100 nm on the surface.

Still further, the surface can include an electrode and the measuring step can include applying a voltage waveform to the electrode to generate an electrochemiluminesce signal. In these embodiments ((31) and (32)), the method can further include collecting the particle on an electrode and applying a voltage waveform to the electrode to generate an electrochemiluminescence signal. The measuring step can include binding the amplicon to a detection probe having a detectable label, measuring the detectable label and correlating the measurement to the amount of analyte in the sample, wherein the detection probe comprising a nucleic acid sequence that is complementary to a region of the amplicon. The detectable label is measured by a measurement of light scattering, optical absorbance, fluorescence, chemiluminescence, electrochemiluminescence, bioluminescence, phosphorescence, radioactivity, magnetic field, or combinations thereof. For example, the detectable label is an ECL label and the measuring step can include measuring an ECL signal.

Embodiment (33): A method of detecting an analyte of interest in a sample comprising: (a) concentrating the sample under conditions sufficient to form an analyte complex comprising the analyte bound to a first detection reagent, wherein the first detection reagent is linked to a first nucleic acid probe; (b) binding the analyte complex formed in step (a) to: (i) a capture reagent on a surface comprising the capture reagent for the analyte, and an anchoring reagent comprising an anchoring oligonucleotide sequence; and (ii) a second detection reagent for the analyte that is linked to a second nucleic acid probe; thereby forming a complex on the surface comprising the capture reagent, the analyte and the first and second detection reagents; (c) using an extension process that requires the first and second probes to be in proximity, extending the second probe to form an extended sequence comprising an anchoring sequence complement that is complementary to the anchoring sequence; (d) hybridizing the anchoring sequence to the anchoring sequence complement; and (e) measuring the amount of extended sequence bound to the surface. The concentrating step (a) can further comprise (i) contacting the sample including the analyte with a solid phase linked to a targeting agent complementary to at least a portion of the first nucleic acid probe, thereby forming a concentration complex comprising the analyte bound to the solid phase via a binding reaction between the first nucleic acid probe and the targeting agent; (ii) collecting the concentration complex; (iii) separating unbound components of the sample from the concentration complex; and (iv) releasing the concentration complex to separate the solid phase from the analyte to form the analyte complex.

Embodiment (34): A kit for the detection of an analyte of interest in a sample comprising, in one or more vials, containers, or compartments: (a) a surface comprising (i) a capture reagent for the analyte, and (ii) an anchoring reagent comprising an anchoring oligonucleotide sequence; (b) a first detection reagent for the analyte that is linked to a first nucleic acid probe; (c) a second detection reagent for the analyte that is linked to a second nucleic acid probe; and (d) a solid phase including a targeting agent complementary to at least a portion of the first nucleic acid probe.

Embodiment (35): A method of detecting an exosome in a sample comprising: (a) binding the exosome to: (i) a capture reagent on a surface comprising the capture reagent for the exosome, and an anchoring reagent comprising an anchoring oligonucleotide sequence; (ii) a first detection reagent for the exosome that is linked to a first nucleic acid probe; and (iii) a second detection reagent for the exosome that is linked to a second nucleic acid probe; thereby forming a complex on the surface comprising the binding reagent, the exosome and the first and second detection reagents; (b) using an extension process that requires the first and second probes to be in proximity, extending the second probe to form an extended sequence comprising an anchoring sequence complement that is complementary to the anchoring sequence; (c) hybridizing the anchoring sequence to the anchoring sequence complement; and (d) measuring the amount of extended sequence bound to the surface.

Embodiment (36): A kit for the detection of an exosome of interest in a sample comprising, in one or more vials, containers, or compartments: (a) a surface comprising (i) a capture reagent for the exosome, and (ii) an anchoring reagent comprising an anchoring oligonucleotide sequence; (b) a first detection reagent for the exosome that is linked to a first nucleic acid probe; and (c) a second detection reagent for the exosome that is linked to a second nucleic acid probe.

BRIEF DESCRIPTION OF THE FIGURES

The patent or application file contains at least one drawing executed in color. Copies of this paper or patent application publication with color drawing(s) will be provided by the Office upon request and payment of the necessary fee.

FIG. 1(a)-(c) illustrate the use of an anchoring reagent in an immunoassay. FIG. 1(a) shows the use of an anchoring reagent to bind to and stabilize a detection complex comprising a capture reagent, an analyte of interest, and a detection reagent including a nucleic acid probe. The nucleic acid probe is extended to bind to the anchoring reagent. In FIG. 1(b), the anchoring reagent includes an oligonucleotide sequence that includes a region complementary to a portion of the extended sequence that forms on the detection reagent. FIG. 1(c) shows a specific embodiment in which two detection reagents are used to bind the analyte, each including a nucleic acid probe. The probes on the detection reagents are subjected to an amplification process that enables the hybridization of one extended probe to the anchor oligonucleotide sequence.

FIG. 2(a) shows a specific embodiment in which the immune complex formed on a surface bearing an anchoring reagent is subjected to a PLA-RCA process to incorporate a plurality of detectable species in the extended sequence attached to the immune complex.

FIG. 4(a) also includes an amplification reagent that includes an anchoring oligonucleotide sequence that is complementary to a sequence of the amplicon that forms as the assay method progresses.

FIGS. 5 and 6(a)-(b) illustrate alternative methods of generating an amplicon that can be amplified by rolling circle amplification.

FIG. 7 illustrates an alternative embodiment in which a portion of each of the proximity probes in the sandwich complex is temporarily protected by short strands of RNA hybridized to each segment. Those strands are enzymatically removed to allow the proximity probes to hybridize to one another and the chain to be extended.

FIG. 8 shows a further embodiment in which proximity probes are attached to the capture reagent and a detection reagent, and a portion of each proximity probe is temporarily protected by short strands of RNA hybridized thereto, as described above in reference to FIG. 8.

FIG. 10(a)-(b) show fluorescence microscopy images with (a) and without (b) the use of an anchoring reagent.

FIGS. 14(a)-(c) show the results of an assay for HIVp24 including an analyte concentration step.

DETAILED DESCRIPTION OF THE INVENTION

Figure 1C:
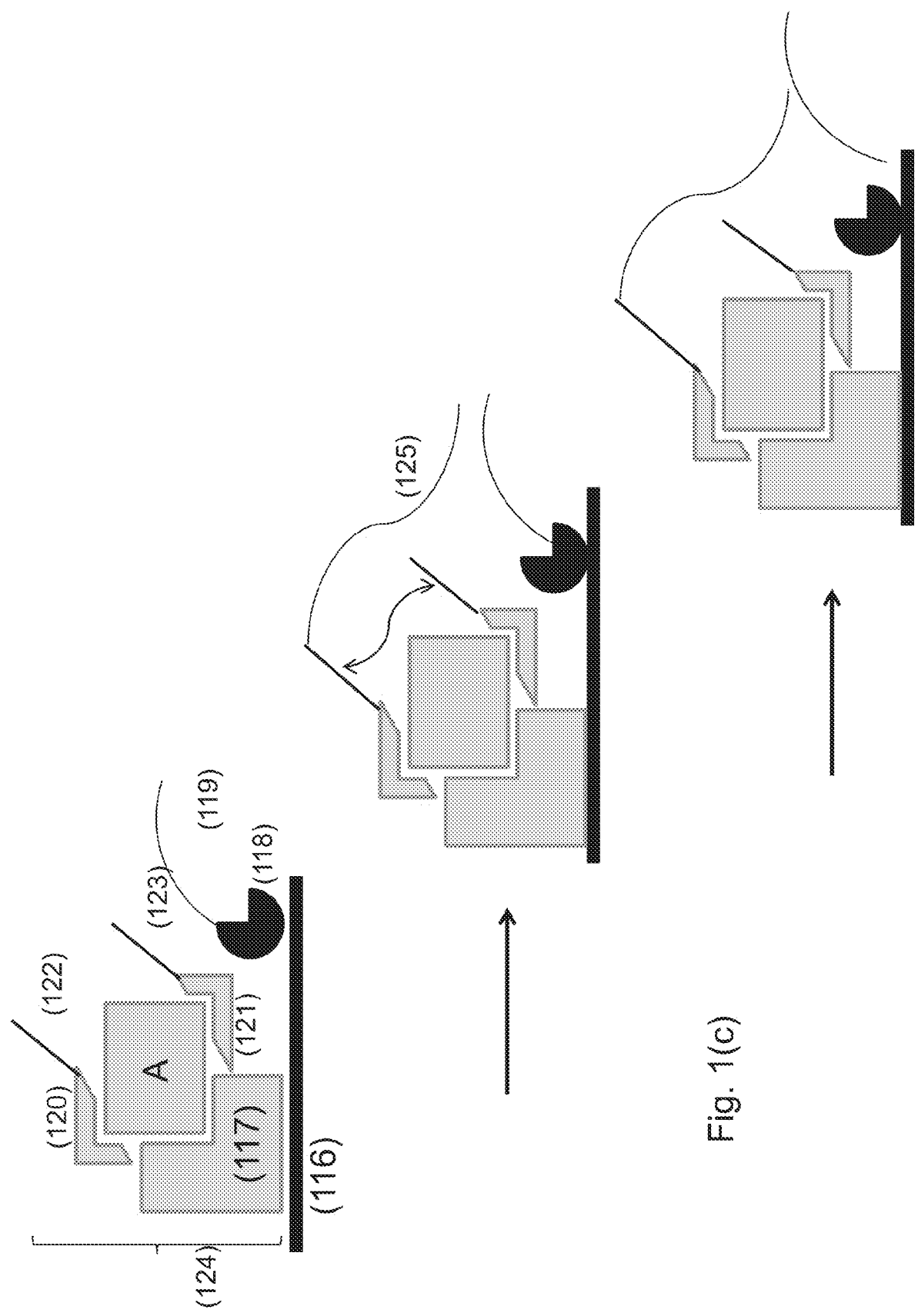

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The present invention includes improved immunoassay methods that comprise (i) anchoring the detection complex formed between the target analyte and one or more analyte binding reagents used in the assay; and/or (ii) amplifying the signal from labeled detection complexes. Anchoring may be used to stabilize complexes involving low binding affinity interactions and/or high molecular weight label(s) or labeling site(s). Signal amplification can be achieved by attaching an extended probe to the binding complex that contains multiple labels or detection labeling sites, thereby amplifying the detectable signal for each individual detection complex. In a preferred embodiment, the method includes attaching an extended probe that includes multiple labels or detection labeling sites to the detection complex, and anchoring the complex to the surface to ensure that the complex is retained on the surface. This modified assay method can be used to detect extremely low numbers of binding events, even individual analyte-binding reagent complexes. The basic approach is not limited to immunoassays and can be used to carry out binding assays using other classes of binding reagents.

One method that can be used to improve binding assays is the use of a surface-bound anchoring reagent to adhere a detection complex including the analyte of interest to the surface and to stabilize the detection complex. This approach may be used to overcome low binding affinities between reagents that form the detection complex and/or prevent the complex from dissociating from the surface prior to subsequent processing. The use of an anchoring reagent in a binding assay is illustrated in FIG. 1(a). The surface (101) includes a capture reagent (102) that binds analyte A, and an anchoring reagent (103). In one or more steps, the analyte is bound to the capture reagent and a detection reagent (104) that also binds the analyte, wherein the detection reagent is linked to a nucleic acid probe (105). The analyte can be bound to the capture and detection reagents simultaneously or substantially simultaneously, or the analyte can be bound to each of the capture and detection reagents sequentially (in either order). Therefore, a complex (106) is formed on the surface that includes the capture reagent, the analyte, and the detection reagent. The probe is extended to form an extended sequence (107) that includes an anchoring region that binds the anchoring reagent. The extended sequence is bound to the anchoring reagent and the amount of extended sequence bound to the surface is measured.

The skilled artisan in the field of binding assays will readily appreciate the scope of capture reagents and companion binding partners that may be used in the present methods. A non-limiting list of such pairs include (in either order) receptor/ligand pairs, antibodies/antigens, natural or synthetic receptor/ligand pairs, hapten/antibody pairs, antigen/antibody pairs, epitope/antibody pairs, mimitope/antibody pairs, aptamer/target molecule pairs, hybridization partners, and intercalater/target molecule pairs. In one embodiment, the binding assays employ antibodies or other receptor proteins as capture and/or detection reagents for an analyte of interest. The term "antibody" includes intact antibody molecules (including hybrid antibodies assembled by in vitro re-association of antibody subunits), antibody fragments and recombinant protein constructs comprising an antigen binding domain of an antibody (as described, e.g., in Porter, R. R. and Weir, R. C. *J. Cell Physiol.,* 67 (Suppl); 51-64 (1966) and Hochman, I. Inbar, D. and Givol, D. *Biochemistry* 12: 1130 (1973)), as well as antibody constructs that have been chemically modified, e.g., by the introduction of a detectable label.

Likewise, the anchoring reagent and the corresponding anchoring member or region can include any suitable binding pair, e.g., receptor/ligand pairs, antibodies/antigens, natural or synthetic receptor/ligand pairs, hapten/antibody pairs, antigen/antibody pairs, epitope/antibody pairs, mimitope/antibody pairs, aptamer/target molecule pairs, hybridization partners, intercalater/target molecule pairs, and the use of a surface and anchoring reagent bound by electrostatic charge. For example, the anchoring reagent can be an oligonucleotide sequence, aptamer, aptamer ligand, antibody, antigen, ligand, receptor, hapten, epitope, or a mimetope, and the corresponding anchoring region includes a complementary oligonucleotide sequence, aptamer ligand, aptamer, antigen, antibody, receptor, ligand, or antibody, respectively. In one specific embodiment, the anchoring region is an oligonucleotide sequence and the anchoring reagent comprises a DNA-binding protein. Alternatively, if the anchoring region is a double stranded oligonucleotide sequence, the anchoring reagent can include an intercalator. In an additional embodiment, the anchoring region can include one or more modified oligonucleotide bases and the corresponding anchoring reagent includes one or more moieties that bind to the modified bases on the anchoring region. For example, the modified bases may include a hapten or ligand and the corresponding anchoring reagent includes one or more antibodies or ligands specific for the hapten or ligand, respectively. Moreover, the anchoring region can include a plurality of labeled nucleotide bases that can be used to detect the detection complex.

In a specific embodiment depicted in FIG. 1(b), the surface-bound anchoring reagent includes an oligonucleotide that is used to anchor the detection complex to the surface. The anchoring oligonucleotide sequence binds to a complementary oligonucleotide sequence that is attached to the detection complex. In this embodiment, the surface (108) includes a capture reagent (109) that binds analyte, A, and an anchoring reagent (110) comprising an anchoring oligonucleotide sequence (111). In one or more steps, the analyte is bound to the capture reagent and a detection reagent (112) that also binds analyte, wherein the detection reagent is linked to a nucleic acid probe (113). As described above in reference to FIG. 1(a), the analyte can be bound to the capture and detection reagents simultaneously or substantially simultaneously, or the analyte can be bound to each of the capture and detection reagents sequentially (in either order). Therefore, a complex (114) is formed on the surface that includes the binding reagent, the analyte and the detection reagent. The probe is extended to form an extended sequence (115) that includes an anchoring sequence complement that is complementary to the anchoring sequence. The anchoring sequence is hybridized to the anchoring sequence complement and the amount of extended sequence bound to the surface is measured.

The detection complex can include one or more detection reagents, e.g., to enhance the specificity of an assay for an analyte. The use of multiple detection reagents can enhance the specificity of an assay if, for example, the assay is designed to emit a detectable signal if each of the detection reagents are in proximity to the analyte or if the signal from a single detection reagent bound to the analyte is distinguishable from the signal emitted from multiple detection reagents bound to the analyte. One embodiment of such an assay is shown in FIG. 1(c). The surface (116) includes a capture reagent (117) that binds analyte A and an anchoring reagent (118) including an anchoring oligonucleotide sequence (119). In one or more steps, the analyte is bound to the capture reagent and each of the two (or more) detection reagents (120 and 121, respectively) that bind the analyte, wherein each of the first and second detection reagents are linked to a nucleic acid probe (122 and 123, the first and second nucleic acid probes, respectively). The analyte can be bound to the capture and detection reagents simultaneously or substantially simultaneously, or in a sequential, step-wise manner. Therefore, a complex (124) is formed on the surface that includes the capture reagent, the analyte, and the first and second detection reagents. Using an extension process that requires the first and second probes to be in proximity to one another, the first probe is extended to form an extended sequence (125) comprising an anchoring sequence complement that is complementary to the anchoring sequence. In the penultimate step, the anchoring sequence is hybridized to the anchoring sequence complement and the amount of extended sequence bound to the surface is measured.

A specific embodiment of the method depicted in FIG. 1(c) is shown in FIG. 2(a), wherein an anchoring reagent is used to adhere the detection complex to the surface and a probe attached to the detection complex is extended to generate an extended region that binds to the anchoring reagent. In this embodiment, the complex is detected using two detection reagents bound to proximity probes. The method further comprises joining the detection reagents with a connector sequence that is then ligated to form a circular target sequence, and subjected to rolling circle amplification to generate an amplicon that binds to the anchoring reagent. The surface (201) includes a capture reagent (202) and an anchoring reagent (203). In one or more steps, the analyte is bound to the capture reagent, a first detection reagent (204) comprising a first proximity probe (205), and a second detection reagent (206) comprising a second proximity probe (207), thereby forming a detection complex (208) on the surface. The detection complex is contacted with two connector sequences (209a and 209b) that each include an end sequence complementary to non-overlapping regions of the first proximity probe and an end sequence complementary to non-overlapping regions of the second proximity probe. The connector sequences are hybridized to the first and second proximity probes, and the end sequences of the connector oligonucleotides are ligated to from a circular target sequence (210) that is hybridized to both the first and second proximity probes. The second proximity probe is extended by rolling circle hybridization to generate an amplicon comprising a binding reagent that binds the anchoring reagent and the amount of amplicon bound to the surface is measured. The first proximity probe may be capped, or otherwise modified, to prevent extension of the first probe. (In an alternative embodiment, the first proximity probe is extended and the second proximity probe can be capped or otherwise modified to prevent extension.) In the embodiment depicted in FIG. 2(a), the amplicon also includes two or more detection sequences which are complementary to labeled detection probes that are hybridized to the amplicon and used to measure the amount of amplicon bound to the surface. In an alternate embodiment (not depicted in FIG. 2(a)), the extension process incorporates labeled nucleotide bases into the amplicon which are used to detect the amplicon on the surface directly, without the addition of one or more labeled probes complementary to the amplicon. FIG. 2(b) is a schematic representation of the components of the connector sequences showing first and second connector oligonucleotides (209a and 209b, respectively), wherein a first end of the first connector ($C_{1(E1)}$) and a first end of the second connector ($C_{2(E1)}$) are complementary to two non-overlapping regions of the first proximity probe, and a second end of the first connector ($C_{1(E2)}$) and a second end of the second connector ($C_{2(E2)}$) are complementary to two non-overlapping regions of the second proximity probe. The first and second connectors are hybridized to the first and second proximity probes and the first and second connectors are ligated to form a circular target sequence that is hybridized to both the first and second proximity probes.

Figure 2C:
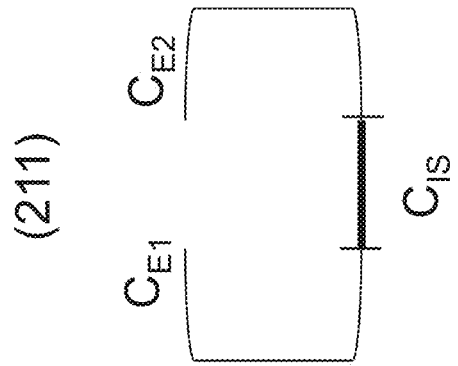
FIGS. 2(b) and 2(c) are two alternative configurations of connection oligonucleotides that can be employed in the method of the invention.
Figure 2B:
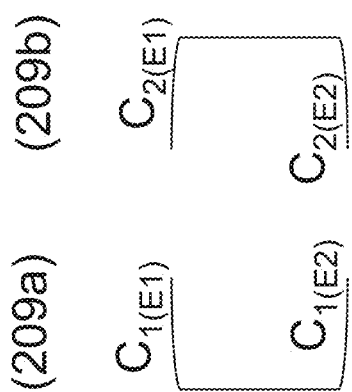

FIG. 2(c) shows an alternate embodiment of the connector. The connector sequence 211 includes an interior sequence ($C_{IS}$) complementary to the second proximity probe and two end sequences ($C_{E1}$ and $C_{E2}$, respectively)

complementary to non-overlapping regions of the first proximity probe. In this embodiment, only one ligation event is needed to form a circular target sequence for rolling circle amplification (i.e., ligation of ends $C_{E1}$ and $C_{E2}$ hybridized to the first proximity probe), however, since priming/extension is from the second proximity probe, the requirement for proximity of the two proximity probes is maintained. Preferably, the first proximity probe is capped, or otherwise modified, to prevent extension of the first probe.

Thereafter, the second proximity probe is extended by rolling circle amplification of the circular target sequence to generate an amplicon comprising a binding region that binds to the anchoring reagent and the amount of amplicon bound to the surface is measured.

The sequences of the first and second proximity probes can be designed by methods known to those skilled in the art. For example, each of the probes are approximately 20-50 bases in length, preferably between 25-40 bases in length, and most preferably between about 30-35 bases in length. The first and second proximity probes also include sequences complementary to one or more connector sequences or portions thereof used in the process as described herein. In one embodiment, the detection complex is contacted with two connector sequences (209a and 209b) that each include an end sequence complementary to non-overlapping regions of the first proximity probe and an end sequence complementary to non-overlapping regions of the second proximity probe. Therefore, in this embodiment, the first and second proximity probe each include non-overlapping regions complementary to end sequences of the connectors. Alternatively, only one connector may be used and the connector sequence (211) includes an interior sequence ($C_{IS}$) complementary to the second proximity probe and two end sequences ($C_{E1}$ and $C_{E2}$, respectively) complementary to non-overlapping regions of the first proximity probe. Therefore, in this embodiment, the first proximity probe includes non-overlapping regions complementary to two end sequences of the connector, $C_{E1}$ and $C_{E2}$, respectively, and the second proximity probe includes a sequence complementary to an interior sequence of the connector ($C_{IS}$). The first proximity probe may be capped, or otherwise modified, to prevent extension of the first probe. (In an alternative embodiment, the first proximity probe is extended and the second proximity probe can be capped or otherwise modified to prevent extension.)

Therefore, the embodiments illustrated in FIGS. 1-2 demonstrate that a binding assay can be modified to incorporate an anchoring reagent and/or the signal from a detection complex can be amplified. In a preferred embodiment, an anchoring reagent and signal amplification methods are employed in a binding assay. In embodiments that include the use of an anchoring reagent, the concentration of anchoring reagent present on the surface is 0.2-200 ug/mL, specifically, 1.0-50 ug/mL, and more specifically, 3.0-10 ug/mL. Alternatively, only one or the other method may be used to achieve an enhanced binding assay. The invention, therefore, includes assays with signal amplification methods as described in FIGS. 1-2, with the anchoring reagent omitted.

Figure 3:
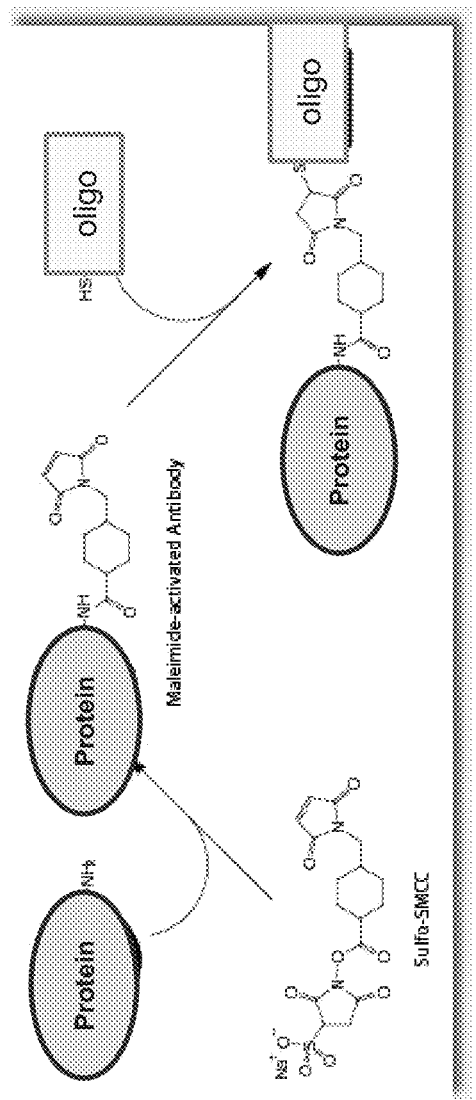
FIG. 3 shows one method of attaching an oligonucleotide to a protein.

In those embodiments in which the anchoring reagent includes an anchoring sequence that is directly or indirectly bound (e.g., through binding reactions) to the surface, methods established in the art for immobilizing oligonucleotides can be employed to generate the anchoring reagent including covalent and non-covalent attachment methods. In one embodiment, the anchoring reagent comprises a protein linked or otherwise bound to the anchoring sequence. In this embodiment, any protein can be used that can be immobilized on a surface (covalently or non-covalently) and modified by an anchoring oligonucleotide. Non-limiting examples include streptavidin, avidin, or bovine serum albumin (BSA). In a preferred embodiment, the anchoring reagent comprises BSA. The protein can be modified by an anchoring oligonucleotide and attached to a surface using known methods, e.g., as illustrated in FIG. 3, using sulfosuccinimidyl-4-(N-maleimidomethyl)cyclohexane-1-carboxylate (Sulfo-SMCC), a well-established heterobifunctional cross-linking agent. Reaction of the N-hydroxysuccinimide (NHS) group of SMCC with bovine serum albumin (BSA) labels the BSA with thiol-reactive maleimide groups. The maleimide groups are, in turn, reacted with thiol-modified oligonucleotides to form BSA-oligonucleotide conjugates that are linked through stable thioether bonds. In one specific example, arrays are formed by printing a series of the BSA-oligonucleotide conjugates on graphitic carbon surfaces, preferably screen printed carbon ink electrodes. Alternatively, if the protein is avidin or streptavidin, the anchoring sequence can be linked to biotin and joined to immobilized avidin or streptavidin through biotin-avidin or biotin-streptavidin interactions.

The anchoring oligonucleotide attached to the anchoring reagent can be any sequence that will hybridize to the extended sequence (or amplicon) that develops during the extension process. The anchoring oligonucleotide may also comprise a non-complementary region (for example a poly (A) sequence) that is used as a linker sequence between the surface and the complementary (hybridizing) region to extend the complementary region away from the surface. In one embodiment, a hybridization sequence is selected to regions of the amplicon that are not associated with binding to the proximity or detection probes (the "inert" regions). In a more specific embodiment, the hybridization sequence is complementary to the full length of the inert region of the amplicon is included (preferably, about 25 nucleotides in length), alone or in combination with a poly(A) arm of e.g., up to 30 nucleotides in length. Preferably, the anchoring oligonucleotide is selected from: (i) (full length complement to the inert region of the amplicon, 25 nucleotides in length)-(20 nucleotide poly (A) arm); or (ii) (complement to a portion of the inert region of the amplicon, 15 nucleotides in length)-(30 nucleotide poly (A) arm).

In one embodiment, a proximity ligation amplification (PLA) is carried out to extend the second proximity probe. As described above in reference to FIGS. 2(*a*)-(*c*), the complex comprising the two proximity probes is contacted with one or more connector oligonucleotides (209a-209b or 211) and ligation of hybridized connector sequences forms a circular oligonucleotide that is then used to extend the second proximity probe by rolling circle amplification (RCA) of the circle. Suitable probe designs and amplification conditions for proximity ligation amplification are well established in the art. A unique aspect of the present invention is the inclusion in one of the connector of the same sequence as is used in the anchoring reagent. During extension of the second proximity probe, the extended region thereby includes the complement of the anchoring sequence, which hybridizes to the anchoring reagent, thereby stabilizing the sandwich complex and preventing dissociation of the second proximity probe. The extended second proximity probe may contain detectable labels (e.g., by inclusion of labeled nucleotides during the RCA extension reaction) that can be measured to determine the amount of analyte on the surface. Alternatively, a plurality of labeled probes comprising detectable labels are added and hybridized to the extended second proximity probe, and the amount of analyte bound to the surface is measured.

Any suitable amplification technique can be used to generate the extended sequence (or amplicon), including but not limited to, PCR (Polymerase Chain Reaction), LCR (Ligase Chain Reaction), SDA (Strand Displacement Amplification), 3SR (Self-Sustained Synthetic Reaction), and isothermal amplification methods, e.g., helicase-dependent amplification and rolling circle amplification (RCA). In a preferred embodiment, RCA is used because it has significant advantages in terms of sensitivity, multiplexing, dynamic range and scalability. Techniques for RCA are known in the art (see, e.g., Baner et al, Nucleic Acids Research, 26:5073 5078, 1998; Lizardi et al., Nature Genetics 19:226, 1998; Schweitzer et al. Proc. Natl. Acad. Sci. USA 97:10113 119, 2000; Faruqi et al., BMC Genomics 2:4, 2000; Nallur et al., Nucl. Acids Res. 29:e118, 2001; Dean et al. Genome Res. 11:1095 1099, 2001; Schweitzer et al., Nature Biotech. 20:359 365, 2002; U.S. Pat. Nos. 6,054,274, 6,291,187, 6,323,009, 6,344,329 and 6,368,801). Several different variants of RCA are known, including linear RCA (LRCA) and exponential RCA (ERCA). RCA generates many thousands of copies of a circular template, with the chain of copies attached to the original target DNA, allowing for spatial resolution of target and rapid amplification of the signal. RCA facilitates (i) detection of single target molecules; (ii) amplification of signals from proteins as well as DNA and RNA; (iii) identifying the location of molecules that have been amplified on a solid surface; (iv) measurement of many different targets simultaneously; and (v) analysis of one or more targets in solution or solid phase. The spatial localization of RCA products with the detection complex is especially advantageous when conducting multiplexed binding assays in an array or particle based format.

Figure 4B:
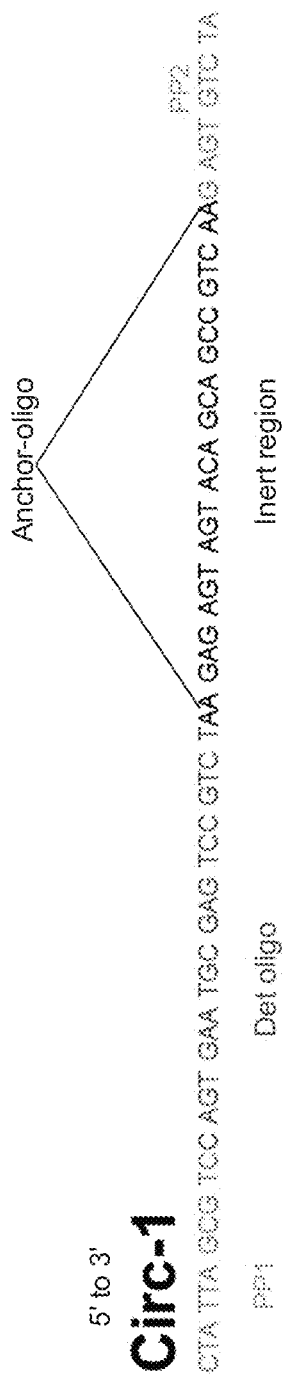
FIG. 4(b) shows an exemplary sequence (SEQ ID NO: 4) of the first circular DNA template Circ-1, a detection oligonucleotide sequence, the inert region of the amplicon, and a portion PP2, which is designed to hybridize to the second proximity probe. An alternative embodiment is depicted in FIG. 4(c), in which Circ-1 (SEQ ID NO: 4) and Circ-2 (SEQ ID NO: 5) hybridized to P1b+P1a (SEQ ID NO: 31) and P2a+P2b (SEQ ID NO: 32).
Figure 4C:
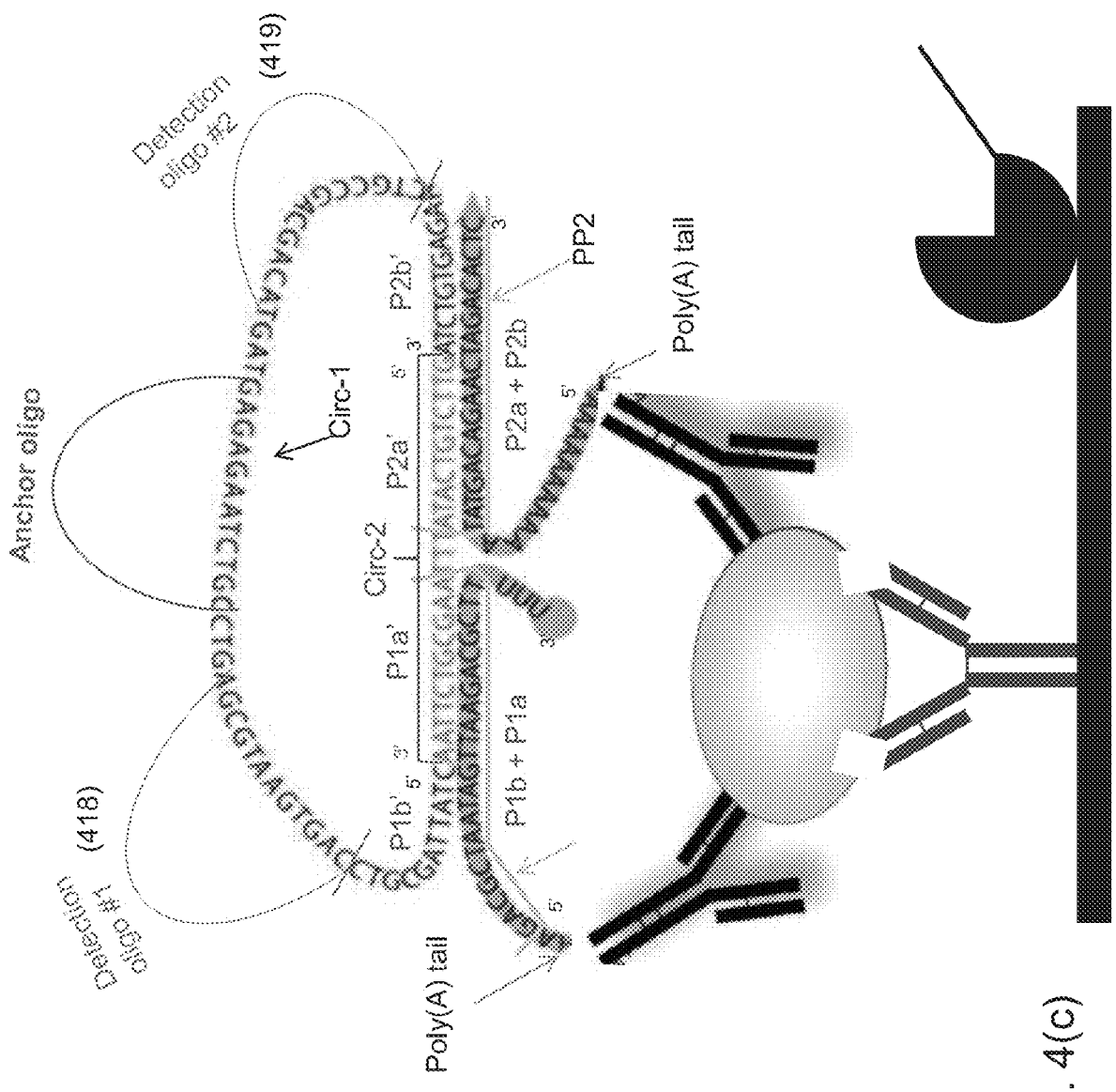
FIG. 4(a) illustrates a preferred embodiment of the invention in which a surface bound complex is formed between a capture reagent, the analyte, and two detection reagents, each attached to a first and second proximity probe, respectively, which are ligated to connector probes to form a circular DNA template that is amplified by rolling circle amplification. Circ-1, SEQ ID NO: 4; Circ-2, SEQ ID NO: 5; PP1, SEQ ID NO: 1 (poly-A tail truncated); PP2, SEQ ID NO: 2.

A specific embodiment of the invention is depicted in FIG. 4(a) in which both an anchoring reagent and a signal amplification process are used. A complex is formed on a surface (401) between a capture reagent (402), the analyte (403) and two detection reagents (304 and 305), each including a first and second proximity probe (406 and 407), respectively. First and second connector oligonucleotides (Circ-1 (408) and Circ-2 (409), respectively in FIG. 4(a)) are added, which when both proximity probes are present in the complex, each hybridize to and bridge the two proximity probes. The bound connector probes are ligated at ligations sites 1 and 2 (410 and 411), respectively to form a circular DNA template (412). The circular DNA template is amplified by rolling circle amplification to extend the second proximity probe and, thereby, generate an amplicon comprising one or more detection sequences (413) and an anchoring oligonucleotide sequence complement (414) (including a partial anchoring sequence complement (415)). The anchoring oligonucleotide sequence (416) (attached to a capture moiety (417)) and its complement hybridize, a plurality of detection probes are hybridized to the plurality of detection probe sequences, and the amount of analyte bound to the surface is measured (not shown but illustrated in FIG. 1(a)). FIG. 4(b) shows an exemplary sequence of the first circular DNA template Circ-1 (408) (which is designed to hybridize to the first proximity probe (PP1)), a detection oligonucleotide sequence, the inert region of the amplicon (which can be used in whole or in part to bind to the anchoring oligonucleotide sequence), and a portion PP2 (which is designed to hybridize to the second proximity probe). An additional embodiment is depicted in FIG. 4(c), in which the circular DNA template is amplified by rolling circle amplification to generate an amplicon comprising a plurality of detection sequences (418 and 419, respectively). In a further embodiment, the anchoring oligonucleotide sequence (416), attached to capture moiety 417, can act as a primer, with a free 3' end. In this embodiment, the second proximity probe includes a sequence that is complementary to the detection sequence (413).

In one embodiment, the assay format described herein makes use of detection reagents coupled to detection sequences at the 5' end with the 3' ends exposed to facilitate ligation to the connector probes to form a circular DNA template which is then amplified by rolling circle amplification to extend the second proximity probe (PP2). In this embodiment, PP1 is potentially independently available for extension by the polymerase but this issue can be addressed by adding modified bases to prevent priming by the polymerase. Alternatively, the ligation template, PP1, can be directly coupled via its 3' end to the detection reagent preventing this oligonucleotide from participating as a primer for DNA polymerase, even if it is degraded.

Figure 5:
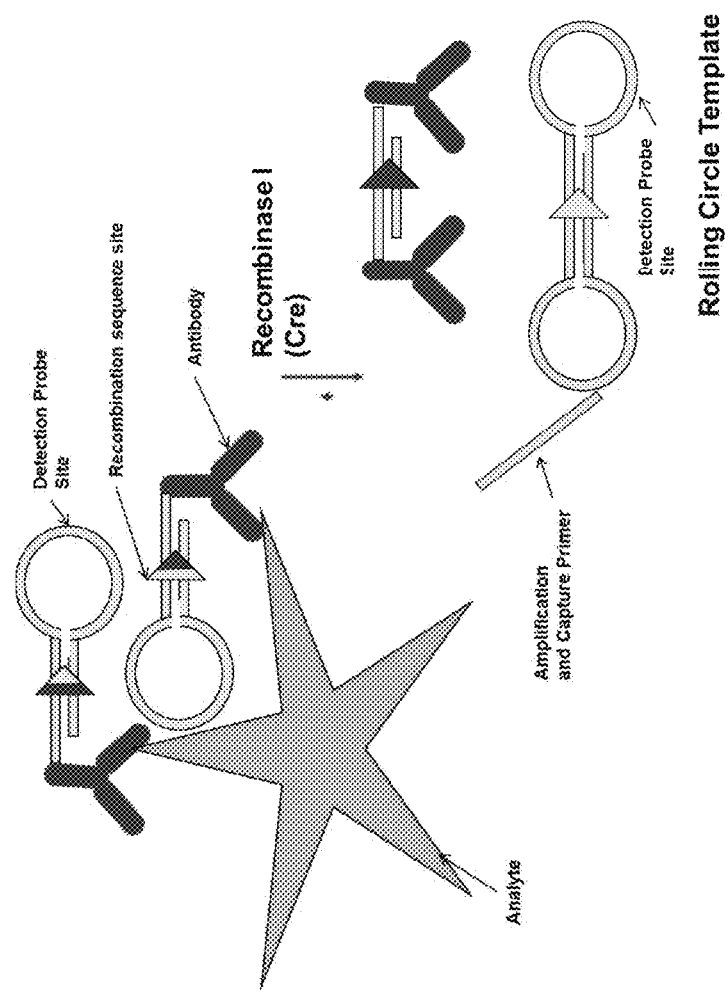

Another approach to generating a target sequence that is amplified by RCA or any suitable amplification method is illustrated in FIG. 5. In this embodiment, each of the proximity probes can fold into a looped hairpin structure. The formation of these hairpin structures generates a single stranded loop and double stranded portion containing a recombination signal. Recombinase is added drive the recombination of the two hairpin structures to form a circular DNA template, which is subsequently subjected to RCA as described above. The amplicon is labeled and optionally anchored to an anchoring reagent and analyte is detected. The key element of this embodiment is the ability of recombinases to catalyze the site specific recombination of DNA containing sequence specific recombination sites. For example, Cre Recombinase from the bacteriophage P1 catalyzes recombination at sites containing loxP sites and other non-limiting examples include but are not limited to Flippase (flp, from Yeast), Hin (Salmonella), and Tre, an engineered (evolved) version of Cre. This alternative approach does not require the addition of additional components such as oligonucleotide templates, ATP and dNTPs. In this embodiment, the loxP (recombination) sites are preferably modified to be non-symmetrical, resulting in a shift in the normal equilibrium towards the formation of the desired recombined product. This is illustrated in FIG. 5, with the light/dark shading of the recombination sites.

Moreover, FIG. 6(a) illustrates yet another method to generate a target sequence that is amplified by RCA or any suitable amplification method. Each of the proximity probes attached to the detection reagents include a loxP site that enables site specific recombination between the two oligonucleotides by Cre recombinase, resulting in the formation of a new oligonucleotide sequence that is composed of the 5' portion of one proximity probe and the 3' portion of the other proximity probe, that flank the lox P sites. The newly created target sequence can be subsequently amplified by any suitable method, labeled, optionally anchored, and detected as described above. FIG. 6(a) illustrates this embodiment using the T7 RNA polymerase promoter as the operable element for amplification. It will also be understood that other RNA polymerase sites such as T3 and SP6 linked at either the 3 or 5' portions of the proximity probes, are equally suitable for use in this method. In this embodiment, the loxP (recombination) sites are preferably modified to be non-symmetrical, resulting in a shift in the normal equilibrium towards the formation of the desired recombined product. As shown in FIG. 6(b), the method can also be used to generate a circular DNA template that can be used in RCA.

The invention includes a method for detecting an analyte comprising binding the analyte to a capture reagent on a surface and two detection reagents to form a detection complex. The method comprises measuring the detection complex, wherein the measuring method preferentially measures complexes comprising both detection reagents, relative to complexes comprising only one of the two detection reagents. In one embodiment, the method comprises forming the complex then cross-linking the detection reagents and detecting the cross-linked reagents. Any suitable cross-linking chemistry can be used to join components of the detection complex. For example, the first and second detection reagents can include reactive moieties that are reacted with and joined by the addition of a multifunctional cross-linking agent that links to the reactive moieties. In this embodiment, the reactive moieties and cross-linking agent can include an amine, thiol, hydrazide, aldehyde, ester, iodoacetamide, maleimide, click chemistry reagents, and combinations thereof. In another embodiment, the first and second detection reagents may include binding moieties and the cross-linking agent is a multivalent binding partner of the binding moieties. Several non-limiting examples of this embodiment include: (a) the first and second detection reagents are antibodies of an animal species and the cross-linking agent is a multivalent anti-species antibody targeting antibodies of the animal species; (b) the first and second detection reagents comprise biotin and the cross-linking agent is streptavidin (or vice versa); (c) the first and second detection reagents are linked to streptavidin and the cross-linking agent is a polymer comprising a plurality of biotin molecules (or vice versa); or (d) the first and second detection reagents comprise first and second nucleic acid probes, respectively, and the cross-linking agent is an oligonucleotide that comprises a sequence complementary to the first nucleic acid probe and a separate sequence complementary to the second nucleic acid probe.

In a specific embodiment, an analyte of interest in a sample can be detected by binding the analyte to an immobilized capture reagent, a first detection reagent and a second detection reagent to form a complex, wherein the first detection reagent comprises a first detectable label and a first nucleic acid probe, and the second detection reagent comprises a second detectable label and a second nucleic acid probe. In this embodiment, the first and second detection reagents are cross-linked by (i) hybridizing the first probe to the second probe, (ii) hybridizing the first and second probes to a third nucleic acid having regions complementary to the first and second probes, or (iii) ligating the first and second probes.

The cross-linked products can be detected once they are bound to the surface, or optionally, the cross-linked products can be released from the surface into an eluent and detected. In this regard, only those individual cross-linked products in the eluent that include both the first and second detectable labels are counted. Any suitable detection method can be employed to detect the presence of labels in the eluent. In a preferred embodiment, the label is a fluorescent molecule and labeled cross-linked products present in the eluent are counted by single molecule fluorescence detection, e.g., fluorescence correlation spectroscopy, and/or fluorescence cross-correlation spectroscopy. In this embodiment, single molecule fluorescence detection comprises flowing the eluent through a capillary, focusing a light source on a volume within the capillary to create an interrogation zone and observing the interrogation zone with a light detector to detect the passage of fluorescent molecules through the interrogation zone. The detection method may further comprise detecting a first fluorescence signal associated with the first label and a second fluorescence signal associated with the second label, and counting detection events when both signals detected from the interrogation zone. Alternatively, one label is a fluorescence resonance energy transfer (FRET) donor and the other label is a FRET acceptor and the detection method may further comprise exciting FRET donors in the interrogation zone and detecting fluorescence signals from the FRET acceptor.

In a specific embodiment, an analyte in a sample can be detected by binding the analyte to an immobilized capture reagent, a first detection reagent and a second detection reagent to form a complex, wherein the first detection reagent comprises a first nucleic acid probe, the second detection reagent comprises a second nucleic acid probe; extending the second nucleic acid probe to form an extended sequence comprising a detectable label, the extension being dependent on the co-localization of the first and second nucleic acid probes in the complex; releasing the extended sequence from the surface into an eluent; and counting individual extended sequences in the eluent. The extending step can include binding the probe to a template nucleic acid sequence and extending the probe by polymerase chain reaction. Alternatively, the extending step comprises binding the first probe to a template nucleic acid sequence, forming a circular nucleic acid template, and extending the circular template by rolling circle amplification. The extending step can also comprise binding the first probe to a template nucleic acid sequence, binding the second probe to the template sequence, and ligating the first and second probes.

In the methods of the invention employing capture reagents, the capture reagents can be directly immobilized on solid phases or they can be indirectly immobilized through secondary binding reagents, such as targeting reagents as described below. For example, a capture reagent may be linked to or comprise a targeting reagent that binds to an immobilized targeting reagent complement on the solid phase. The binding of a targeting reagent to its complement may be direct (for example, the targeting reagent may be streptavidin and the complement may be biotin) or indirect through a bridging agent (e.g., the targeting reagent and complement may be biotin, and the bridging reagent may be a multivalent biotin binding receptor such as streptavidin). In one embodiment, a targeting agent and its complement comprise a first oligonucleotide and a complementary oligonucleotide, a receptor-ligand pair, an antigen-antibody pair, a hapten-antibody pair, an epitope-antibody pair, a mimetope-antibody pair, an aptamer-target molecule pair, hybridization partners, or an intercalator-target molecule pair. The targeting agents and complements used in an assay are selected such that the targeting agents and complements associated with a capture or detection reagent for an analyte measured by the assay are substantially non-cross-reactive with the targeting agents and complements associated with the capture or detection reagents for the other analytes measured by the assay. For example, the binding of a binding reagent to its associated binding domain (through its associated targeting agent and targeting agent complement) should be substantially greater than its binding to binding domains associated with other analytes (and presenting different targeting agent complements). Preferably the cross-reactivity for the binding of capture or detection reagents for an analyte to binding domains associated with other analytes relative to the binding to the correct binding domain is <1%, more preferably <0.1% and more preferably <0.01%. In a preferred embodiment, the targeting agent/targeting agent complement comprise a pair of oligonucleotides including complementary sequences and the targeting agent and its complement are contacted under conditions sufficient to hybridize the targeting agent to its complement.

When targeting agents are used, there is some flexibility as to when the capture reagent used in an assay method is immobilized on a solid phase. In one embodiment, the capture reagent is provided to the user pre-immobilized on a solid phase through a targeting agent—targeting agent complement interaction. In another embodiment, a capture reagent linked to a targeting agent and a solid phase supporting an immobilized targeting agent complement are provided as separate components. The assay method, therefore further comprises the step of immobilizing the capture reagent on the solid phase by binding the targeting agent to its complement (directly or through the use of a bridging agent). This step may be carried out prior to, concurrently with, or subsequent to the steps associated with formation of a detection complex.

In a specific embodiment, multi-functional targeting agents can be used in the assay methods and components described herein. A multi-functional targeting agent can include (a) a first segment designed to bind to a capture reagent via a first segment complement (i.e., the capture reagent includes a targeting agent complement that is complementary to the first segment of the multi-functional targeting agent), and (b) a second segment designed to bind to the amplicon (i.e., the second segment of the multi-functional targeting agent serves as the anchoring reagent on the surface). Therefore, in this embodiment, a surface includes the multi-functional targeting agent which is contacted with a capture reagent that binds to the targeting agent via a linkage between the first segment and the first segment complement. The 3-AB RCA/PLA assay proceeds as described herein, and the amplicon binds to the anchor segment of the multi-functional targeting agent prior to the measuring step. This method can be used to insure a 1:1 ratio of capture agent to anchoring reagent is employed in the assay method.

A wide variety of surfaces are suitable for use in the methods of the present invention including conventional surfaces from the art of binding assays. Surfaces may be made from a variety of different materials including polymers (e.g., polystyrene and polypropylene), ceramics, glass, composite materials (e.g., carbon-polymer composites such as carbon-based inks). Suitable surfaces include the surfaces of macroscopic objects such as an interior surface of an assay container (e.g., test tubes, cuvettes, flow cells, FACS cell sorter, cartridges, wells in a multi-well plate, etc.), slides, assay chips (such as those used in gene or protein chip measurements), pins or probes, beads, filtration media, lateral flow media (for example, filtration membranes used in lateral flow test strips), etc.

Suitable surfaces also include particles (including but not limited to colloids or beads) commonly used in other types of particle-based assays e.g., magnetic, polypropylene, and latex particles, materials typically used in solid-phase synthesis e.g., polystyrene and polyacrylamide particles, and materials typically used in chromatographic applications e.g., silica, alumina, polyacrylamide, polystyrene. The materials may also be a fiber such as a carbon fibril. Microparticles may be inanimate or alternatively, may include animate biological entities such as cells, viruses, bacterium and the like. A particle used in the present method may be comprised of any material suitable for attachment to one or more capture or detection reagents, and that may be collected via, e.g., centrifugation, gravity, filtration or magnetic collection. A wide variety of different types of particles that may be attached to capture or detection reagents are sold commercially for use in binding assays. These include non-magnetic particles as well as particles comprising magnetizable materials which allow the particles to be collected with a magnetic field. In one embodiment, the particles are comprised of a conductive and/or semiconductive material, e.g., colloidal gold particles. The microparticles may have a wide variety of sizes and shapes. By way of example and not limitation, microparticles may be between 5 nanometers and 100 micrometers. Preferably microparticles have sizes between 20 nm and 10 micrometers. The particles may be spherical, oblong, rod-like, etc., or they may be irregular in shape.

The particles used in the present method may be coded to allow for the identification of specific particles or subpopulations of particles in a mixture of particles. The use of such coded particles has been used to enable multiplexing of assays employing particles as solid phase supports for binding assays. In one approach, particles are manufactured to include one or more fluorescent dyes and specific populations of particles are identified based on the intensity and/or relative intensity of fluorescence emissions at one or more wave lengths. This approach has been used in the Luminex xMAP systems (see, e.g., U.S. Pat. No. 6,939,720) and the Becton Dickinson Cytometric Bead Array systems. Alternatively, particles may be coded through differences in other physical properties such as size, shape, imbedded optical patterns and the like. One or more particles provided in a mixture or set of particles may be coded to be distinguishable from other particles in the mixture by virtue of particle optical properties, size, shape, imbedded optical patterns and the like.

In a specific embodiment, the methods of the invention can be used in a multiplexed format by binding a plurality of different analytes to a plurality of capture reagents for those analytes, the capture analytes being immobilized on coded bead, such that the coding identifies the capture reagent (and analyte target) for a specific bead. The method may further comprise counting the number of beads that have a bound analyte (using the detection approaches described herein).

Alternatively or additionally, the detection complex and/or capture reagents can be bound, directly or indirectly, to different discrete binding domains on one or more solid phases, e.g., as in a binding array wherein the binding domains are individual array elements, or in a set of beads wherein the binding domains are the individual beads, such that discrete assay signals are generated on and measured from each binding domain. If capture reagents for different analytes are immobilized in different binding domains, the different analytes bound to those domains can be measured independently. In one example of such an embodiment, the binding domains are prepared by immobilizing, on one or more surfaces, discrete domains of capture reagents that bind analytes of interest. Optionally, the surface(s) may define, in part, one or more boundaries of a container (e.g., a flow cell, well, cuvette, etc.) which holds the sample or through which the sample is passed. In a preferred embodiment, individual binding domains are formed on electrodes for use in electrochemical or electrochemiluminescence assays. Multiplexed measurement of analytes on a surface comprising a plurality of binding domains using electrochemiluminescence has been used in the Meso Scale Diagnostics, LLC, MULTI-ARRAY® and SECTOR® Imager line of products (see, e.g., U.S. Pat. Nos. 7,842,246 and 6,977,722, the disclosures of which are incorporated herein by reference in their entireties).

Still further, the detection complex and/or capture reagents can be bound, directly or indirectly, to an electrode surface, which optionally includes different discrete binding domains, as described above. The electrode surface can be a component of a multi-well plate and/or a flow cell. Electrodes can comprise a conductive material, e.g., a metal such as gold, silver, platinum, nickel, steel, iridium, copper, aluminum, a conductive allow, or the like. They may also include oxide coated metals, e.g., aluminum oxide coated aluminum. The electrode can include a working and counter electrodes which can be made of the same or different materials, e.g., a metal counter electrode and carbon working electrode. In one specific embodiment, electrodes comprise carbon-based materials such as carbon, carbon black, graphitic carbon, carbon nanotubes, carbon fibrils, graphite, graphene, carbon fibers and mixtures thereof. In one embodiment, the electrodes comprise elemental carbon, e.g., graphitic, carbon black, carbon nanotubes, etc. Advantageously, they may include conducting carbon-polymer composites, conducting particles dispersed in a matrix (e.g. carbon inks, carbon pastes, metal inks, graphene inks), and/or conducting polymers. One specific embodiment of the invention is an assay module, preferably a multi-well plate, having electrodes (e.g., working and/or counter electrodes) that comprise carbon, e.g., carbon layers, and/or screen-printed layers of carbon inks.

The invention includes methods for detecting and counting individual detection complexes. In a specific embodiment, the surface can comprise a plurality of capture reagents for one or more analyte molecules that are present in a sample and the plurality of capture reagents are distributed across a plurality of resolvable binding regions positioned on the surface. Under the conditions used to carry out and analyze a measurement, a "resolvable binding region" is the minimal surface area associated with an individual binding event that can be resolved and differentiated from another area in which an additional individual binding event is occurring. Therefore, the method consists of binding the one or more analyte molecules to one or more capture reagents on the surface, determining the presence or absence of an analyte molecule in a plurality of resolvable binding regions on the surface, and identifying the number of resolvable binding regions that contain an analyte molecule and/or the number of analyte domains that do not contain an analyte molecule.

The resolvable binding regions can be optically interrogated, in whole or in part, i.e., each individual resolvable binding region can be individually optically interrogated and/or the entire surface comprising a plurality of resolvable binding regions can be imaged and one or more pixels or groupings of pixels within that image can be mapped to an individual resolvable binding region. A resolvable binding region may also be a microparticle within a plurality of microparticles. The resolvable binding regions exhibiting changes in their optical signature can be identified by a conventional optical detection system. Depending on the detected species (e.g., type of fluorescence entity, etc.) and the operative wavelengths, optical filters designed for a particular wavelength can be employed for optical interrogation of the resolvable binding regions. In embodiments where optical interrogation is used, the system can comprise more than one light source and/or a plurality of filters to adjust the wavelength and/or intensity of the light source. In some embodiments, the optical signal from a plurality of resolvable binding regions is captured using a CCD camera. Other non-limiting examples of camera imaging systems that can be used to capture images include charge injection devices (CIDs), complementary metal oxide semiconductors (CMOSs) devices, scientific CMOS (sCMOS) devices, and time delay integration (TDI) devices, as will be known to those of ordinary skill in the art. In some embodiments, a scanning mirror system coupled with a photodiode or photomultiplier tube (PMT) can be used for imaging.

The measuring step of the method can comprise imaging an optical signal from the surface (or a portion thereof) to generate an image that consists of a plurality of pixels, wherein each resolvable binding region maps to one or more pixels or groups of pixels in the image. Image analysis to identify pixels or sets of pixels having a signal indicative of a binding event (detection complex) can be accomplished using art recognized methods, for example, the wealth of image analysis algorithms and software available to identify and count labeled biological structures in fluorescence microscopy images. In one embodiment, after filtering the image to remove large-scale signal gradients, the image is converted to a binary image using a segmentation threshold. Resolvable binding regions are found by identifying contiguous regions of above-threshold intensity. Binding domains are categorized as binding events if they meet size and intensity requirements.

In one embodiment, the resolvable binding regions are elements of an array. In a preferred embodiment, the array is an array of micro-wells or nanowells, e.g., individual depressions or wells of a unitary substrate. Preferably, the volume of the wells is less than 100 nL, preferably less than 50 nL. In one embodiment, the volume of the wells ranges from approximately 10 aL-100 pL. Optionally, the wells may be configured to hold a microparticle.

In one embodiment, at least 50% of the resolvable binding regions positioned on a substrate and addressed during an assay contain either zero or one analyte molecule. Preferably, at least 80%, more preferably at least 95%, and most preferably at least 99% of the resolvable binding regions contain either zero or more analyte molecule. The concentration of analyte molecules in the sample is determined at least in part using a calibration curve, a Poisson distribution analysis and/or a Gaussian distribution analysis of the number of binding regions that contain at least one or one analyte molecule. In a specific embodiment, the surface comprises a plurality of particles each including a plurality of capture reagents for an analyte molecule and the plurality of particles is distributed across a plurality of resolvable binding regions (e.g., an array of micro- or nano-wells). Therefore, the method includes: (i) binding one or more analyte molecules to one or more capture reagents on the surface, (ii) distributing the plurality of particles across an array of resolvable binding regions; and (iii) determining the presence or absence of an analyte molecule in each resolvable binding regions, so as to identify the number of binding domains that contain an analyte molecule and/or the number of binding domains that do not contain an analyte molecule.

It may also be advantageous to detect an analyte in a confined volume using one or more of the methods of the present invention. In these embodiments, an analyte molecule in a sample is bound to a pair of detection reagents, each bearing distinguishable labels, and analytes are partitioned across a plurality of locations, e.g., wells or reaction vessels (referred to herein as "reaction vessels"), on a substrate, e.g., a plate, dish, chip, optical fiber, grid, etc., so that the majority of reaction vessels contain one or fewer analytes. This method enables the user to detect the analyte molecule by counting the number of reaction vessels that contain each of the distinguishable labels attached to the analyte. In some cases, the plurality of reaction vessels addressed is a portion or essentially all of the total quantity of reaction vessels which may contain at least one analyte molecule (e.g., either associated with at least one analyte molecule or not associated with any analyte molecules). Reference is made to the following published U.S. Patent Applications: U.S. Patent Application No. 20070259448; U.S. Patent Application No. 20070259385; U.S. Patent Application No. 20070259381; and International Patent Application No. PCT/US07/019184; and International Patent Application No. PCT/US09/005428. The disclosures of each of these publications are incorporated herein by reference. At least a portion of the reaction vessels may be addressed and a measure indicative of the number/percentage of the reaction vessels containing at least one analyte molecule or particle may be made. In some cases, based upon the number/percentage, a measure of the concentration of analyte molecules in the fluid sample may be determined.

In a specific embodiment that enables the detection of an analyte molecule in a confined volume, analytes in a sample can be detected by binding the analytes to first and second detection reagents to form detection complexes. Each detection complex includes an analyte, a first detection reagent, and a second detection reagent, and the first detection reagent and the second detection reagent have first and second detectable labels, respectively. The detection complexes can be formed simultaneously, substantially simultaneously, or sequentially. The detection complexes are partitioned across a plurality of reaction vessels so that the majority of reaction vessels contain one or fewer detection complexes, and the number of analyte molecules is detected by counting the number of reaction vessels that contain each of the first and second detectable labels. Preferably, the detection complexes are partitioned across the plurality of reaction vessels so that the likelihood of detecting an unbound first detection reagent and an unbound second detection reagent in the same vessel is less than about 1 in 10, preferably less than about 1 in 100, more preferably less than about 1 in 1000, and most preferably less than about 1 in 10,000. The detection complexes are partitioned across a plurality of reaction vessels, i.e., divided or separated into parts or portions, e.g., manually by aliquoting a portion of detection complexes across a plurality of reaction vessels, and/or by flowing a solution comprising detection complexes across a plurality of reaction vessels so that detection complexes are separated into individual reaction vessels on a support.

In a further embodiment, analytes in a sample can be detected by (a) binding the analytes to surface-bound capture reagents and first and second detection reagents to form detection complexes, wherein (i) each detection complex includes a capture reagent, an analyte, a first detection reagent, and a second detection reagent, and (ii) the first detection reagent has a first detectable label and the second detection reagent has a second detectable label. The detection complexes can be formed by any order of addition of components, e.g., by simultaneously or substantially simultaneously bringing the components together, or sequentially adding each component to build the detection complex in a step-wise fashion. The detection complexes are partitioned across a plurality of reaction vessels so that the majority of reaction vessels contain one or fewer analytes, and the number of analyte molecules is detected by counting the number of reaction vessels that contain the first and second detectable labels. The method can be conducted with or without washing after each step and prior to the detection step.

The surface can be a particle and optionally, a plurality of capture reagents are immobilized on a particle or a plurality of particles. In this embodiment, the partitioning step can be conducted in a number of ways: (i) the capture reagents are immobilized on a plurality of particles and the partitioning of analytes is achieved by binding the analytes to the capture reagents and partitioning the particles into the plurality of reaction vessels; or (ii) the capture reagents are immobilized on a plurality of particles and the partitioning of analytes is achieved by partitioning the particles into a plurality of reaction vessels then binding the analytes to the capture reagents.

The plurality of reaction vessels can also comprise water droplets dispersed in a water-in-oil emulsion. Emulsions can be made with droplets of diameters up to 100 um and volumes of nearly 1 nL. The high capacity, i.e., greater than $10^{10}$ droplets in 1 mL of emulsion, the ease of preparing emulsions and their high stability over a broad range of conditions render them an ideal means of compartmentalizing biochemical assays. Each water droplet functions as an independent reaction vessel and detection complexes, optionally attached to a particle, can be partitioned across a plurality of water droplets.

Alternatively, the surface is a location within one of the reaction vessels, e.g., if the reaction vessels are wells of a plate, then the surface can be a domain or region within one of the wells of the plate. In this embodiment, the capture reagents can be immobilized on the domains or regions of the plurality of reaction vessels and the partitioning step is achieved by binding the analyte molecules to the capture reagents. In another embodiment, the plurality of reaction vessels includes regions with targeting moieties immobilized thereto, the capture reagents comprise targeting moiety complements, and the partitioning step is achieved by binding the targeting moiety complements to the target moieties positioned in the plurality of reaction vessels.

In an additional or alternative embodiment, the binding assays described herein can also include a pre-concentration step to improve assay performance, for example, by increasing the concentration of analyte in the sample and/or by reducing the concentration of extraneous materials that may be present in the sample which may hinder the performance of the assay. This can be done by (a) contacting a sample including the analyte of interest with a solid phase, e.g., particle, linked to a first binding reagent that binds the analyte, thereby forming a complex comprising the analyte bound to said first binding reagent; (b) collecting the complex; (c) separating unbound components of the sample from the complex; (d) and releasing the complex. This method of concentrating the analyte can be performed before the binding assays described herein are performed in order to remove impurities that might hinder assay performance. In this regard, reference is made to U.S. Application Publication No. US 2010/0261292, the disclosure of which is incorporated herein by reference.

In particular, the concentration step involves subjecting the sample comprising the analyte under conditions sufficient to form an analyte complex that includes the analyte bound to a first detection reagent, wherein the first detection reagent is linked to a first nucleic acid probe. Thereafter, the analyte complex formed at the conclusion of the concentration step is bound to (i) a capture reagent on a surface comprising the capture reagent for the analyte, and an anchoring reagent comprising an anchoring oligonucleotide sequence; and (ii) a second detection reagent for the analyte that is linked to a second nucleic acid probe; thereby forming a complex on the surface comprising the capture reagent, the analyte and the first and second detection reagents. The surface bound complex is subject to an extension process that requires the first and second probes to be in proximity, extending the second probe to form an extended sequence comprising an anchoring sequence complement that is complementary to the anchoring sequence. The anchoring sequence is then hybridized to the anchoring sequence complement; and the amount of extended sequence bound to the surface is measured. In a specific embodiment, the concentrating step further comprises: (i) contacting the sample including the analyte with a solid phase linked to a targeting agent complementary to at least a portion of the first nucleic acid probe, thereby forming a concentration complex comprising the analyte bound to the solid phase via a binding reaction between the first nucleic acid probe and the targeting agent; (ii) collecting the concentration complex; (iii) separating unbound components of the sample from the concentration complex; and (iv) releasing the concentration complex to separate the solid phase from the analyte to form the analyte complex.

Collection, as used herein, refers to the physical localization of a material in a mixture. Collection includes the localization of a material through binding reactions or adsorption. For example, a material in a mixture may be collected on a solid phase by adsorption of the material on the solid phase or by binding of the material to binding reagents on the solid phase. Collection is not, however, limited to localization at a solid phase and may also include techniques in the art for localizing materials at a location/ volume within a larger fluid volume, for example, localization of materials through the use of optical tweezers (which use light to manipulate microscopic objects as small as a single atom, wherein the radiation pressure from a focused laser beam is able to trap small particles), electric or magnetic fields, focused flow, density gradient centrifugation, etc.

Certain embodiments of the invention include the collection of microparticles or materials that are bound to microparticles. Suitable collection methods include the many methods known in the art of microparticle-based assays that achieve localization of microparticles from a suspension. These include sedimentation under gravity or by centrifugation, filtration onto a filter or porous membrane, localization (of magnetizable particles) by application of a magnetic field, binding or adsorption of the particles to a macroscopic solid phase, use of optical tweezers, etc.

Release, as used herein, refers to delocalization of a previously collected material. Materials that are held at a localized position through chemical bonds or through specific or non-specific binding interactions may be allowed to delocalize by breaking the bond or interaction so that the materials may diffuse or mix into the surrounding media. There are many well-established cleavable chemical linkers that may be used that provide a covalent bond that may be cleaved without requiring harsh conditions. For example, disulfide containing linkers may be cleaved using thiols or other reducing agents, cis-diol containing linkers may be cleaved using periodate, metal-ligand interactions (such as nickel-histidine) may be cleaved by changing pH or introducing competing ligands. Similarly, there are many well-established reversible binding pairs that may be employed (including those that have been identified in the art of affinity chromatography). By way of example, the binding of many antibody-ligand pairs can be reversed through changes in pH, addition of protein denaturants or chaotropic agents, addition of competing ligands, etc. Other suitable reversible binding pairs include complementary nucleic acid sequences, the hybridization of which may be reversed under a variety of conditions including changing pH, decreasing salt concentration, increasing temperature above the melting temperature for the pair and/or adding nucleic acid denaturants (such as formamide). Such reversible binding pairs may be used as targeting agents (as described above), e.g., a first targeting agent may be linked to a first binding reagent that binds an analyte, a second targeting agent may be linked to a solid phase, and a binding interaction of the first and second targeting agents may be used to reversibly immobilize the first binding reagent on the solid phase.

Release also includes physical delocalization of materials by, for example, mixing, shaking, vortexing, convective fluid flow, mixing by application of magnetic, electrical or optical forces and the like. Where microparticles or materials bound to microparticles have been collected, such physical methods may be used to resuspend the particles in a surrounding matrix. Release may simply be the reverse of a previous collection step (e.g., by any of the mechanisms described above) or collection and release could proceed by two different mechanisms. In one such example, collection of materials (such as an analyte or a complex comprising an analyte) bound to a particle can be achieved by physical collection of the particle. The materials are then released by cleaving a bond or reversing a binding reaction holding the material on the particle. In a second such example, materials (such as an analyte of a complex comprising an analyte are collected on a surface through a binding interaction with a binding reagent that is linked to the surface. The material is then released by breaking a bond or a second binding interaction linking the binding reagent to the surface.

Collection followed by release may be used to concentrate and/or purify analytes in a sample. By collecting in a first volume and releasing into a second smaller volume, an analyte in a sample can be concentrated. Through concentration, it is often possible to significantly improve the sensitivity of a subsequent measurement step. By collecting from a sample and removing some or all of the uncollected sample, potential assay interferents in the sample may be reduced or eliminated. Optionally, removal of the unbound sample may include washing a collected material with and releasing the collected material into defined liquid reagents (e.g., assay or wash buffers) so as to provide a uniform matrix for subsequent assay steps.

Figure 16:
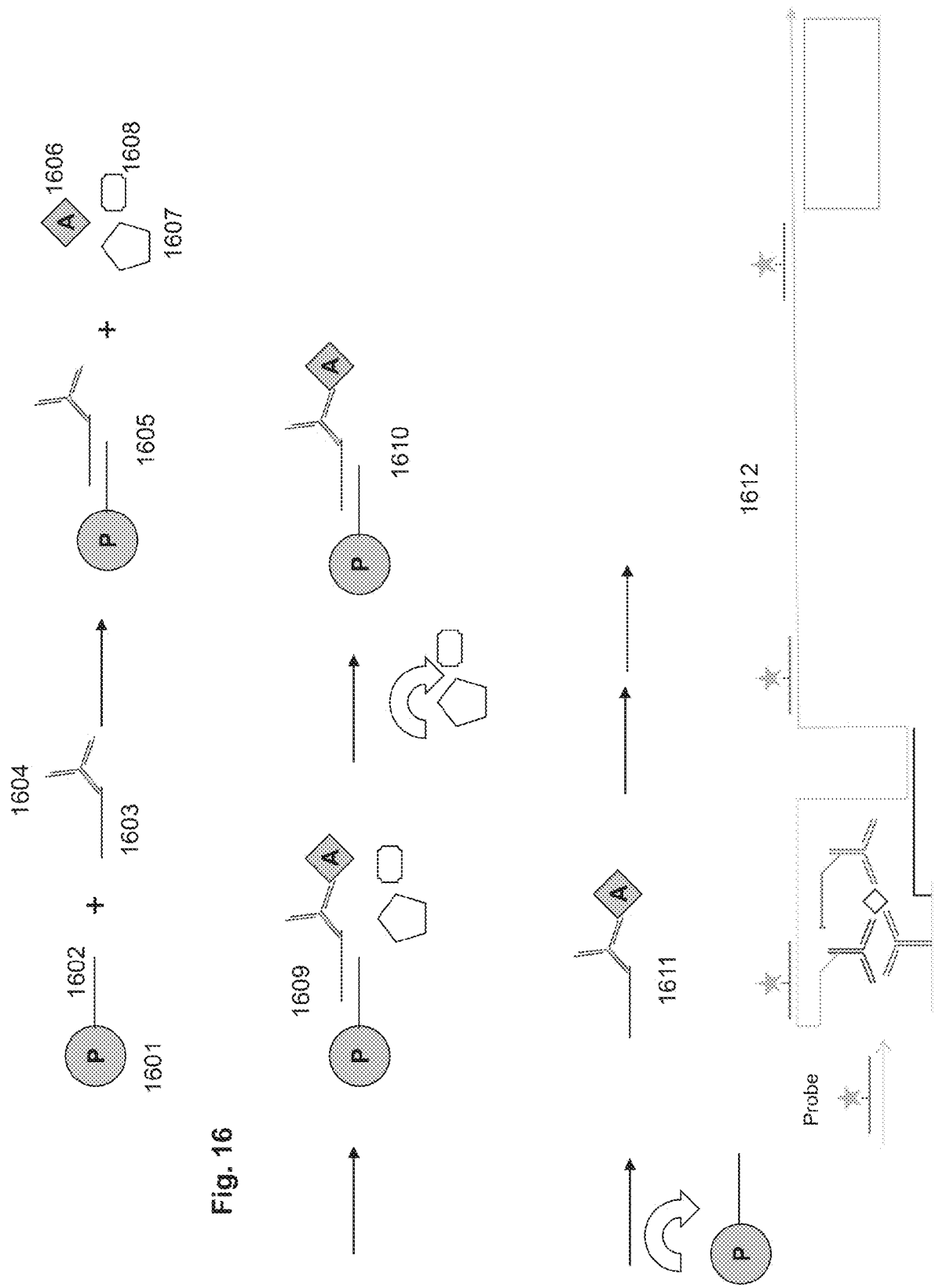
FIG. 16 is a schematic representation of an assay method as described herein including an analyte concentration step.

As illustrated in FIG. 3(a) of US 2010/0261292, which is incorporated herein by reference, the method includes contacting a sample comprising a target analyte with a particle linked to a first binding reagent that binds the target analyte, wherein the first binding reagent is linked to a first targeting agent and the particle is linked to a second targeting agent, and the first binding reagent and the particle are linked via a binding reaction between the first and second targeting agents to form a complex comprising said target analyte bound to said first binding reagent. The complex is then collected and unbound components in the sample are separated from the complex. The complex is released and the released complex is contacted with a second binding reagent bound to a solid phase, wherein the second binding reagent binds to the complex. This specific embodiment is illustrated in FIG. 16. A particle (1601) is modified to include a capture oligonucleotide sequence, 1602, which is complementary, at least in part, to the sequence of a proximity probe, 1603, which is bound to a detection antibody, 1604. The particle is mixed with the proximity probe to hybridize the capture sequence to the probe sequence to form a complex, 1605. The complex is then mixed with a sample comprising analyte, 1606, and optionally, one or more contaminants, 1607-1608. The analyte is bound to the detection antibody (1609) and the contaminants are removed (1610). The particle is removed under suitable conditions from the complex including bound analyte to form a concentrated solution of analyte bound to proximity probe (1611), which may be used as described herein in an immunoassay in which an additional proximity probe is bound to the analyte and a 3-antibody complex is subjected to RCA-PLA to detect the presence of analyte in the sample (1612), e.g., as described in FIG. 2(*a*) and the accompanying description.

Figure 17:
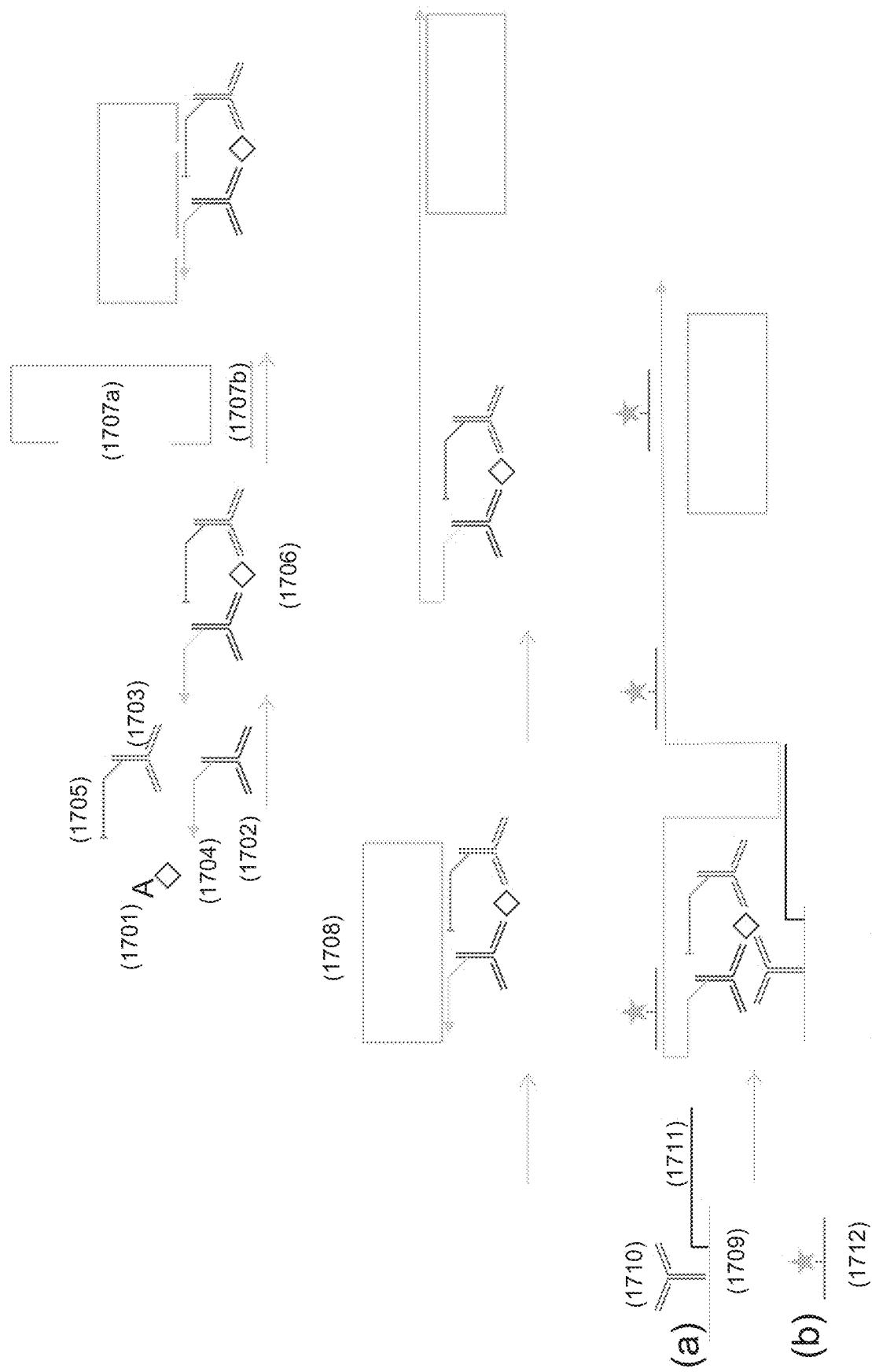
FIG. 17 is a schematic representation of an assay method as described herein wherein the amplicon is formed in solution prior to being bound to a surface via a capture reagent and/or anchoring reagent.

In another embodiment, an immunoassay complex between detection antibodies and analyte is formed in solution, followed by amplification, and then the amplified product is adhered to a particle via capture reagent and/or anchor. Optionally, the amplified product can be filtered and then captured on a particle via a capture reagent and/or anchor. This method is illustrated in FIG. 17. The analyte, A (1701) is bound to the detection antibodies (1702 and 1703, respectively) each bound to proximity probes (1704 and 1705, respectively) and a detection complex is formed comprising analyte bound to each of the detection antibodies (1706). The detection complex is contacted with two connector sequences (1707*a* and 1707*b*) that each include an end sequence complementary to non-overlapping regions of the first proximity probe and an end sequence complementary to non-overlapping regions of the second proximity probe. The connector sequences are hybridized to the first and second proximity probes, and the end sequences of the connector oligonucleotides are ligated to from a circular target sequence (1708) that is hybridized to both the first and second proximity probes. The second proximity probe is extended by rolling circle hybridization to generate an amplicon comprising a binding reagent that is complementary to an anchoring reagent. The amplicon is contacted with the surface (1709) including the capture reagent (1710) and anchoring reagent (1711) and the amount of amplicon bound to the surface is measured via labeling using a plurality of labeled probes (1712).

Additionally, the method described herein can be used for the detection and quantitation of oligomeric analytes. If the target antigen is a homo-oligomer, i.e., an antigen having two or more identical subunits, the detection antibody needs to be labeled independently with both the ligation templating oligonucleotide and the primer oligonucleotide. This can lead to inefficiencies, as two antibodies with only templating oligonucleotides or two antibodies with only priming oligonucleotides can bind and such nonproductive complexes can reduce the sensitivity of this approach. This issue can be aggravated when this approach is applied to the detection of specific oligomeric structures, where additional specific templating oligonucleotides are used to allow for the specific detection of the oligomer. Therefore, the methods described herein can include preformation of a set of detection antibodies configured to efficiently bind a desired oligomer analyte, together with the template for formation of the rolling circle template. This can be achieved using an additional oligonucleotide sequence, e.g., a scaffolding oligonucleotide, which can specifically hybridize to the antibody coupled oligonucleotides so that the antibodies are configured in the detection antibody mixture in oligomeric form, matched to the target antigen oligomer. This preorganization step allows for the optimal binding of the detection antibodies to the target oligomer. Following the binding of the detection antibody to the oligomer antigen, the scaffolding oligonucleotide can be removed via exonuclease degradation or another suitable chemical method or endonuclease treatment. Once the scaffolding oligonucleotide is removed, the proximity ligation rolling circle amplification assay can proceed as described herein.

In an additional embodiment, the assay format described herein further includes one or more control assays. A negative control can be included on a binding domain which includes a capture antibody that does not have a corresponding detection antibody, thereby providing a consistent background signal for all samples. Measurement of signal above a preset threshold value can indicate improper assay processing or the presence of a sample-dependent matrix effect causing non-specific binding of labeled detection probe. Moreover, a specimen control can also be included in the assay for a human target antigen (such as a secreted or intracellular protein) that performs multiple control functions. A positive signal will indicate the presence of human material, and therefore test for sample addition and quality. The human antigen can also serve as a process control for bacterial antigen extraction. For example, an intracellular human analyte can be selected as a specimen control that also requires lysis and extraction to be detected, e.g. Akt. Measurement of a signal below a predefined threshold would indicate that no sample was added, that a failure in the reagents or process occurred, or that substances that interfere with amplification or detection are present. In addition to internal controls, external positive and negative controls can also be used with the method and/or kit. The positive control can comprise a mixture of non-infectious bacterial extracts representing all specific target antigens detected by the multiplexed panel, providing a positive signal for all assays when tested. The negative control comprises a representative matrix without any target proteins.

Examples of samples that may be analyzed by the methods of the present invention include, but are not limited to food samples (including food extracts, food homogenates, beverages, etc.), environmental samples (e.g., soil samples, environmental sludges, collected environmental aerosols, environmental wipes, water filtrates, etc.), industrial samples (e.g., starting materials, products or intermediates from an industrial production process), human clinical samples, veterinary samples and other samples of biological origin. Biological samples that may be analyzed include, but are not limited to, feces, mucosal swabs, physiological samples and/or samples containing suspensions of cells. Specific examples of biological samples include blood, serum, plasma, feces, mucosal swabs, tissue aspirates, tissue homogenates, cell cultures and cell culture supernatants (including cultures of eukaryotic and prokaryotic cells), urine, saliva, sputum, and cerebrospinal sample.

Analytes that may be measured using the methods of the invention include, but are not limited to proteins, toxins, nucleic acids, microorganisms, viruses, cells, fungi, spores, carbohydrates, lipids, glycoproteins, lipoproteins, polysaccharides, drugs, hormones, steroids, nutrients, metabolites and any modified derivative of the above molecules, or any complex comprising one or more of the above molecules or combinations thereof. The level of an analyte of interest in a sample may be indicative of a disease or disease condition or it may simply indicate whether the patient was exposed to that analyte.

In a specific embodiment, the analyte of interest is an exosome, i.e., a small membrane vesicle released by most cell types. The release and subsequent uptake of exosomes is a method of cell-to-cell communication and has a role in the regulation of many physiological and pathological processes. Exosomes have been shown to contain a wide variety of signaling molecules including but not limited to surface-bound and cytosolic proteins, lipids, mRNA, and miRNA, and it has been suggested that the identity and concentration of these species in each exosome can be used to deduce its cellular origin and function. Thus, genomic or proteomic profiling of a patient's total exosome population could provide valuable prognostic information for various pathological conditions, including cancers, infectious disease, kidney and liver disease, and traumatic brain injury, among others.

Exosomes are typically measured in the aggregate by isolating large numbers of them from biological fluids, disrupting their membranes, and assaying the contents by conventional methods such as western blot, PCR, or sequencing. However, the methods and kits of the present invention can be used to characterize exosomes via capture of the exosome(s) on a surface and subsequent detection of target molecules expressed by the exosome. Several proteins have been identified as common among most exosomes, e.g., CD9, CD63, CD81, Hsp70, PDCD6IP, Tsg101, and in one embodiment, these targets can be used individually or in combination to capture the exosome on a surface via binding interactions between one or more capture reagents and one or more common exosome target proteins. In an alternative or additional embodiment, a disease associated marker present on or in the exosome is used to capture the exosome on a surface via a binding interaction between one or more capture reagents and a disease-associated exosome marker. The captured exosome(s) then can be probed using one or more detection reagents, directed either towards one or more of the common exosome proteins, or one or more additional molecular targets present within or on the surface of some fraction of exosomes. When distinct targets are selected for the capture and detection reagents, only those exosomes comprising both targets will be detected allowing additional specificity in identifying or quantifying subpopulations of exosomes. In a specific embodiment, the sample used is a purified exosome preparation.

In a particular embodiment, detection of a particular phenotypically distinct exosome subpopulation can be effected using a pair of detection reagents that only produce a signal when brought into proximity by binding interactions with proximal targets as described herein. In the present embodiment, the proximal targets may be distinct epitopes on the same molecule, they may be different copies of the same molecular species held in proximity within the interior of a single exosome or bound in the membrane of the same exosome, or they may be different interacting species in or on a single exosome, such as two interacting proteins (e.g., tetraspanin-integrin complexes), a protein receptor and ligand (e.g. EFG and EGFR), or an mRNA molecule and an RNA binding protein (e.g. Argonaute 1-4, or GW182). In addition, the use of methods described herein permits the analysis of up to three distinct target molecules that may not be functionally linked, but linked by the presence within a single exosome. Proximity probes used in the PLA/RCA methods described herein can be lengthened to permit ligation and subsequent amplification of target molecules that are positioned further apart on or in the exosome. In one embodiment, a PLA/RCA assay is conducted using specific fluorescent probes for the amplicon. Thereafter, the capture exosomes are labeled with a generic fluorescent reagent, e.g., acridine orange for RNA in the exosome, and the capture exosomes are imaged to determine the correlation between the two fluorescent signatures. The use of a generic fluorescent reagent allows for selection of signals from the desired exosome or a subset thereof, based on size and staining intensity.

In order to probe internal target molecules, (cargo proteins, lipids or RNA molecules) the exosomes can be fixed and permeabilized either prior to or after capture but before adding detection reagents. If permeabilized exosomes are interrogated using the methods described herein, one or both of the detection reagents can comprise an oligonucleotide probe capable of binding to a specific RNA sequence, enabling detection of mRNA, miRNA, and/or interactions between proteins and RNA.

Exosomes can be measured using the methods described herein with or without the use of an anchoring reagent. As described above, the use of an anchoring reagent in a binding assay is illustrated in FIG. 1($a$) and if the analyte is an exosome, the surface (101) includes a capture reagent, e.g., directed to a common exosome target protein. In a specific embodiment, the surface also includes an anchoring reagent (103). In one or more steps, the exosome is bound to the capture reagent and a detection reagent (104) that also binds the exosome via the same or a different exosome target protein, wherein the detection reagent is linked to a nucleic acid probe (105). Therefore, a complex is formed on the surface that includes the capture reagent, the exosome, and the detection reagent. The probe is extended to form an extended sequence (107) that includes an anchoring region that binds the anchoring reagent. The extended sequence is bound to the anchoring reagent and the amount of extended sequence bound to the surface is measured.

Likewise, the method illustrated in FIG. 1($b$) can also be applied to the detection of exosomes. In a specific embodiment, the detection complex can include one or more detection reagents to enhance the specificity of an assay for the exosome, e.g., as illustrated in FIG. 1($c$). In one or more steps, the exosome is bound to the capture reagent and each of the two (or more) detection reagents (120 and 121, respectively) that bind a target protein expressed by the exosome, wherein each of the first and second detection reagents are linked to a nucleic acid probe (122 and 123, the first and second nucleic acid probes, respectively). The exosome can be bound to the capture and detection reagents simultaneously or substantially simultaneously, or in a sequential, step-wise manner. Therefore, a complex (124) is formed on the surface that includes the capture reagent, the exosome, and the first and second detection reagents. Using an extension process that requires the first and second probes to be in proximity to one another, the first probe is extended to form an extended sequence (125) comprising an anchoring sequence complement that is complementary to the anchoring sequence. In the penultimate step, the anchoring sequence is hybridized to the anchoring sequence complement and the amount of extended sequence bound to the surface is measured. Similarly, the methods depicted in each of FIGS. 2($a$)-($c$) can be used to detect exosomes.

The assays of the present invention may be used to determine the concentration of one or more, e.g., two or more analytes in a sample. Thus, two or more analytes may be measured in the same sample. Panels of analytes that can be measured in the same sample include, for example, panels of assays for analytes or activities associated with a disease state or physiological conditions. Certain such panels include panels of cytokines and/or their receptors (e.g., one or more of TNF-alpha, TNF-beta, IL1-alpha, IL1-beta, IL2, IL4, IL6, IL-10, IL-12, IFN-γ, etc.), growth factors and/or their receptors (e.g., one or more of EGF, VGF, TGF, VEGF, etc.), drugs of abuse, therapeutic drugs, vitamins, pathogen specific antibodies, auto-antibodies (e.g., one or more antibodies directed against the Sm, RNP, SS-A, SS-alpha, J0-1, and Scl-70 antigens), allergen-specific antibodies, tumor markers (e.g., one or more of CEA, PSA, CA-125 II, CA 15-3, CA 19-9, CA 72-4, CYFRA 21-1, NSE, AFP, etc.), markers of cardiac disease including congestive heart disease and/or acute myocardial infarction (e.g., one or more of Troponin T, Troponin I, Troponin C, myoglobin, CKMB, myeloperoxidase, glutathione peroxidase, β-natriuretic protein (BNP), alpha-natriuretic protein (ANP), endothelin, aldosterone, C-reactive protein (CRP), etc.), markers associated with hemostasis (e.g., one or more of Fibrin monomer, D-dimer, thrombin-antithrombin complex, prothrombin fragments 1 and 2, anti-Factor Xa, etc.), markers of acute viral hepatitis infection (e.g., one or more of IgM antibody to hepatitis A virus, IgM antibody to hepatitis B core antigen, hepatitis B surface antigen, antibody to hepatitis C virus, etc.), markers of Alzheimers Disease (alpha-amyloid, beta-amyloid, Aβ 42, Aβ 40, Aβ 38, Aβ 39, Aβ 37, Aβ 34, tau-protein, etc.), markers of osteoporosis (e.g., one or more of cross-linked Nor C-telopeptides, total deoxypyridinoline, free deoxypyridinoline, osteocalcin, alkaline phosphatase, C-terminal propeptide of type I collagen, bone-specific alkaline phosphatase, etc.), markers of fertility state or fertility associated disorders (e.g., one or more of Estradiol, progesterone, follicle stimulating hormone (FSH), lutenizing hormone (LH), prolactin, hCG, testosterone, etc.), markers of thyroid disorders (e.g., one or more of thyroid stimulating hormone (TSH), Total T3, Free T3, Total T4, Free T4, and reverse T3), and markers of prostate cancer (e.g., one or more of total PSA, free PSA, complexed PSA, prostatic acid phosphatase, creatine kinase, etc.). Certain embodiments of invention include measuring, e.g., one or more, two or more, four or more or 10 or more analytes associated with a specific disease state or physiological condition (e.g., analytes grouped together in a panel, such as those listed above; e.g., a panel useful for the diagnosis of thyroid disorders may include e.g., one or more of thyroid stimulating hormone (TSH), Total T3, Free T3, Total T4, Free T4, and reverse T3).

In a preferred embodiment, the panel includes one or more low abundance analytes in traditional sample matrices, e.g., analytes at a concentration of less than about 100 fg/mL, and preferably, less than about 10 fg/mL. A non-limiting list of analytes that can be included in the panel includes, e.g., IL-17, IL-21, IL-31, Ab-38, Ab-40, Ab-42, Ab-39, Ab-43, Ab-15, Ab-16, Ab-17, Abeta oligomers, C-peptide, IL-13, IL-17A, IL-2, IL-4, IL-5, IL-6, IL-8, IL-12/23p40, IL-12p70, INF-g, PSA, PSAc, Tau, phospho-Tau, TNFa, troponin I, cardiac troponin T, troponin C, VEGF, VEGF-A, VEGF-B, VEGF-C, VEGF-D, EPO, LC3B, albumin, CHO-P, E. coli HCP, IgA, IgE, IgG, IgG1, IgG4, IgM, NSO-P, Per-C6, residual protein A, IgG2, IgG3, IgG4, AFP, CA125, Caspase-3 active, CXCL11/I-TAC, ErbB2/HER2, HGFR/o-MET, IFN-beta, MMP1, MMP2, MMP3, MMP9, beta-NGF, TFF3, TIMP1, Kim-1, alpha-2 macroglobulin, D-dimer, ICAM-1, myeloperoxidase, myoglobin, PAI-1, PCSK9, plasminogen, renin/prorenin, tPA, CXCL1/GRO-alpha, CCL2/MCP1, CCL3/MIP-1alpha, CCL4/MIP-1beta, CCL5/Rantes, CRP, CXCL9/MIG, CXCL10/IL-10, G-CSF, GM-CSF, IFN-alpha, IFN-gamma, IL1alpha, IL-1beta, IL2, IL3, IL4, IL5, IL6, IL7, IL8, IL12(p70), IL13, IL15, IL18, IL-22, IL-23, IL-33, c-MET, adiponectin, FGF21, TSLP, GLP-1, growth hormone, IGF1, IGF2, insulin, leptin, prolactin, HIV p24, HB-EGF, AKT, phospho-AKT, and combinations thereof.

In a specific embodiment, the panel includes one or more low abundance analytes in traditional sample matrices, e.g., analytes at a concentration of less than about 100 fg/mL, and preferably, less than about 10 fg/mL, and the panel includes one or more of the following human targets: G-CDF, GM-CSF, IFNgamma, IL-1beta, IL-2, IL-4, IL-5, IL-6, IL-10, IL-12/23p40, IL12p70, IL-17A, IL21, IL-22, IL-23, IL-31, IL-33, TNFalpha, TSLP, VEGF, complexed PSA, free PSA, Abeta42, Abeta40, Abeta38, tau, cardiac troponin I, cardiac troponin T, HIV p24, C-peptide, and/or FGF21.

In addition, the methods and kit described herein can be used in immunoassays to detect single organism sensitivity to antimicrobial resistance markers (PBP2a/mecA (S. aureus, gram-positive), TEM1 (E. coli, gram-negative)). These assays can be used to this class of analytes, in both gram-positive and gram-negative bacteria. One or more of the following target proteins involved with antimicrobial resistance to vancomycin, beta-lactam, carbapenem, aminoglycoside and macrolide antibiotics can be included in the assay; erm family, vanA, vanB, aac(6')-aph(2"), KPC, NDM, OXA-48, VIM, OXA-23 like, OXA-40 like, OXA-58 like, ESBL genes of CTX-M-1 and CTX-M-9 families, and combinations thereof. Moreover, one or more of the following proteins can be included in the assay: 50S ribosomal protein L20, 30S ribosomal protein S7, 30S ribosomal protein S2, 50S ribosomal protein L21, 50S ribosomal protein L17, 30S ribosomal protein S4, 50S ribosomal protein L15, 30S ribosomal protein S5, 50S ribosomal protein L16, 30S ribosomal protein S3, 50S ribosomal protein L22, 50S ribosomal protein L4, ribosomal protein L25, 50S ribosomal protein L5, 30S ribosomal protein S2, ribosomal proteins L30, L31 and L32, and combinations thereof. In addition, one or more of the following targets can be evaluated, alone or in combination with one or more of the markers identified herein, e.g., elongation factor EF-TU, ACP, the Acyl carrier protein, RplL, a ribosomal protein GroS (MopB, 65,000), a component of the chaperone system Gro-EL-Gro-ES and GapA, enzyme in glycolysis, and combinations thereof.

Still further, the methods and kits described herein can also be used in immunoassays to detect healthcare associated infections (HAI organisms), including but not limited to *Klebsiella pneumonia*, *Acinetobacter baumannii*, *Pseudomonas aeruginosa*, *Enterobacter* species, and extra-intestinal pathogenic *Escherichia coli*. Resistance markers for each of the HAI organisms are provided in the table below:

| Pathogen | Drug Resistance Marker (GenBank ID) |
| --- | --- |
| *Klebsiella pneumoniae* | KPC (KPC-2: AAK70220.1) |
| *Acinetobacter baumannii* | VIM (VIM-1: CCG05854.1) |
| *Pseudomonas aeruginosa* | IMP-1 (AAL17637.1) |
| *Enterobacter* species | OXA-48 (AGD80396.1) |
| extra-intestinal pathogenic *Escherichia coli* | NDM (NDM-1: AHF22464.1) |

Specific outer membrane proteins can be evaluated in the immunoassays described herein:

| Pathogen | Outer Membrane Protein | GenBank Accession # |
| --- | --- | --- |
| *Klebsiella pneumoniae* | lpp | YP_002238023.1 |
|  | ompA | WP_004144094.1 |

-continued

| Pathogen | Outer Membrane Protein | GenBank Accession # |
|---|---|---|
| *Enterobacter cloacae* | lpp | YP_003612855.1 |
| | ompA | WP_023481315.1 |
| *Enterobacter aerogenes* | lpp | YP_004593622.1 |
| | ompA | YP_007388430.1 |
| *Escherichia coli* | lpp | NP_416192.1 |
| | ompA | NP_286832.1 |
| *Pseudomonas aeruginosa* | oprF | NP_250468.1 |
| *Acinetobacter baumannii* | omp38 | YP_008889447.1 |

In addition, the methods and kits described herein can be used in an immunoassay to detect one or more of the following classes of biomarkers: cytokines, circulating tumor-specific proteins, proteins associated with one or more infectious diseases, intracellular markers, etc., and combinations thereof.

Still further, the following autoimmune diseases can be identified using the methods and kits described herein by evaluating the presence or absence of one or more of the associated antigens listed below:

| Organ-Specific Diseases | Associated Antigens |
|---|---|
| Type 1 Diabetes | Glutamic acid decarboxylase (GAD) |
| | Insulinoma-2 (IA2A) |
| | Zinc Transported 8 protein (ZnT8) |
| | Proinsulin |
| | Insulin |
| Celiac Disease | Transglutaminase (tTG) |
| | Gliadin (deamidated) |
| | Deamidated forms of gliadin peptides (DGP) |
| Addison's Disease | 21-hydroxylase (21-OH) |
| | 17-hydroxylase (17-OH) |
| | Cytochrome p450 side chain cleavage enzyme (SCC) |
| Hashimoto's Thyroiditis | Thyroid peroxidase (TPO) |
| | Thyroglobulin |
| Graves' Hyperthyroidism | Thyrotropin receptor |
| Hypoparathyroidism | Calcium-sensing receptor |
| Primary biliary cirrhosis | Pyruvate dehydrogenase complex (PDC-E2) |
| | Branched chain 2-oxo-acid dehydrogenase complex (BCOADC-E2) |
| | 2-oxoglutarate dehydrogenase complex (OGDC-E2) |
| | Gp120 |
| | Sp100 |
| | Nup62 |
| Automimmune hepatitis | Cytochrome P450 2D6 |
| Type II | Formiminotransferase Cyclodeaminase |
| Autoimmune gastritis | H+/K+ ATPase |
| Pernicious Anemia | H+/K+ ATPase |
| Alopecia | Tyrosiine hydroxylase |
| Vitiligo | Tyrosinase |
| | SOX-10 |
| | SOX-9 |

In a particular embodiment, the panel includes one or more low abundance analytes in traditional sample matrices, e.g., analytes at a concentration of less than about 100 fg/mL, and preferably, less than about 10 fg/mL. The panel preferably includes one or more of the following analytes: IL-17, IL-21, IL-31, IL-22, IL-23, IL-33, cardiac troponin T, and combinations thereof. In specific embodiments, the concentration of analyte detected in the sample is within a range of 0.01 fM to 100 fM, 0.03 fM-50 fM, or 0.03 fM-10 fM. In some embodiments, the concentration of analyte molecules in the sample that may be substantially accurately determined is less than about 100 fM, less than about 10 fM, less than about 3 fM, less than about 1 fM, less than about 0.3 fM, less than about 0.1 fM, less than about 0.03 fM, or less. The concentration of analyte molecules in a sample may be considered to be substantially accurately determined if the measured concentration of the analyte molecules in the sample is within about 20% of the actual concentration of the analyte molecules in the sample. In certain embodiments, the measured concentration of the analyte molecules in the sample may be within about 10%, within about 3%, or within about 1% of the actual concentration of the analyte molecules in the sample. The limit of detection for the assay is that concentration that gives a signal that is at least 2.5 standard deviations above the background signal, and preferably the assay can detect approximately 10-10,000 molecules in a sample, or 100-5,000 molecules in a sample, or 100-1000 molecules in a sample.

In a further embodiment, the methods described herein can be used to detect analytes that are in low abundance due to a recent exposure and/or infection. Early diagnosis of various diseases or conditions, e.g., cancer, bacterial infections, e.g., *Bacillus anthracis* (Anthrax), viral infections, e.g., HIV, hepatitis, HPV, etc., toxin exposure, e.g., ricin, botulinum toxin A, B, or E, etc., is limited by the fact that the limits of detections (LOD) of available technologies, such as ELISA, are higher than the circulating concentrations of low abundance proteins that could indicate the onset of disease. The panel can include one or more low abundance analytes in traditional sample matrices, e.g., analytes at a concentration of less than about 100 fg/mL, or less than about 10 fg/mL. A non-limiting list of analytes that can be included in the panel includes, e.g., HIVgp41, HIVgp120, HIVgp160, HIVp24, HIVp66, HIVp51, HIVp17, HIVp31, Tat, Nef, Viv, hepatitis A, B, C, D, or E antigens, HPV types 16, 18, 31, 33, 35, 39, 45, 51, 52, 56, 58, 59, 68, 73, and/or 82, HPV-E6 and E7 proteins, IL-17, IL-21, IL-31, IL-22, IL-23, IL-33, cardiac troponin T, and combinations thereof. Still further, the panel can also include one or more of the follow analytes that may be in low abundance due to recent disease onset, exposure and/or infection: Ab-38, Ab-40, Ab-42, Ab-39, Ab-43, Ab-15, Ab-16, Ab-17, Abeta oligomers, C-peptide, IL-13, IL-17A, IL-2, IL-4, IL-5, IL-6, IL-8, INF-g, PSA, Tau, phospho-Tau, TNFa, troponin I, cardiac troponin T, troponin C, VEGF, VEGF-A, VEGF-B, VEGF-C, VEGF-D, EPO, LC3B, albumin, CHO-P, *E. coli* HCP, IgA, IgE, IgG, IgG1, IgG4, IgM, NSO-P, Per-C6, residual protein A, IgG2, IgG3, IgG4, AFP, CA125, Caspase-3 active, CXCL11/I-TAC, ErbB2/HER2, HGFR/o-MET, IFN-beta, MMP1, MMP2, MMP3, MMP9, beta-NGF, TFF3, TIMP1, Kim-1, alpha-2 macroglobulin, D-dimer, ICAM-1, myeloperoxidase, myoglobin, PAI-1, PCSK9, plasminogen, renin/prorenin, tPA, CXCL1/GRO-alpha, CCL2/MCP1, CCL3/MIP-1alpha, CCL4/MIP-1beta, CCL5/Rantes, CRP, CXCL9/MIG, CXCL10/IL-10, G-CSF, GM-CSF, IFN-alpha, IFN-gamma, IL1alpha, IL-1beta, IL-3, IL-7, IL-12 (p70), IL-13, IL-15, IL-18, c-MET, adiponectin, FGF21, GLP-1, growth hormone, IGF1, IGF2, insulin, leptin, prolactin, HB-EGF, AKT, phospho-AKT, and combinations thereof.

The methods of the present invention are designed to allow detection of a wide variety of biological and biochemical agents, as described above. In one embodiment, the methods may be used to detect pathogenic and/or potentially pathogenic virus, bacteria and toxins including biological warfare agents ("BWAs") in a variety of relevant clinical and environmental matrices, including and without limitation, blood, sputum, stool, filters, swabs, etc. A non-limiting list of pathogens and toxins that may be analyzed (alone or in combination) using the methods of the present invention is *Bacillus anthracis* (anthrax), *Yersinia pestis* (plague), *Vibrio cholerae* (cholera), *Francisella tularensis* (tularemia), *Brucella* spp. (Brucellosis), *Coxiella burnetii* (Q fever), *listeria, salmonella, shigella, V. cholera, Chlamydia trachomatis, Burkholderia pseudomallei*, orthopox viruses including variola virus (smallpox), viral encephalitis, Venezuelan equine encephalitis virus (VEE), western equine encephalitis virus (WEE), eastern equine encephalitis virus (EEE), Alphavirus, viral hemorrhagic fevers, Arenaviridae, Bunyaviridae, Filoviridae, Flaviviridae, Ebola virus, staphylococcal enterotoxins, ricin, botulinum toxins (A, B, E), *Clostridium botulinum*, mycotoxin, *Fusarium, Myrotecium, Cephalosporium, Trichoderma, Verticimonosporium, Stachybotrys*, glanders, wheat fungus, *Bacillus globigii, Serratia marcescens*, yellow rain, trichothecene mycotoxins, *Salmonella typhimurium*, aflatoxin, *Xenopsylla cheopis, Diamanus montanus*, alastrim, monkeypox, Arenavirus, Hantavirus, Lassa fever, Argentine hemorrhagic fevers, Bolivian hemorrhagic fevers, Rift Valley fever virus, Crimean-Congo virus, Hanta virus, Marburg hemorrhagic fevers, yellow fever virus, dengue fever viruses, influenza (including human and animal strains including H5N1 avian influenza, influenza A, influenza A, H1 specific, influenza A, H3 specific, influenza A, H5 specific, influenza A, 2009-H1N1 specific, influenza B), RSV, human immunodeficiency viruses I and II (HIV I and II), hepatitis A, hepatitis B, hepatitis C, hepatitis (non-A, B or C), Enterovirus, Epstein-Barr virus, Cytomegalovirus, herpes simplex viruses, *Chlamydia trachomatis, Neisseria gonorrheae, Trichomonas vaginalis*, human papilloma virus, *Treponema pallidum, Streptococcus pneumonia, Borellia burgdorferi, Haemophilus influenzae, Mycoplasma pneumoniae, Chlamydophila pneumoniae, Legionella pneumophila, Staphylococcus aureus, Staphylococcus* Enterotoxin B (SEB), Abrin, Shiga Toxin 1, Shiga Toxin 2, *Moraxella catarrhalis, Streptococcus pyogenes, Clostridium difficile, Neisseria meningitidis, Klebsiella pneumoniae, Mycobacterium tuberculosis*, Group A *streptococcus, E. Coli* 0157, coronavirus, Coxsackie A virus, rhinovirus, parainfluenza virus, respiratory syncytial virus (RSV), metapneumovirus, vaccinia, and adenovirus.

The improvements to binding assays described herein can be used to expand the dynamic range of a binding assay, i.e., the range of the concentration of analyte molecules in a fluid sample that may be quantitated by a system or method without dilution or concentration of the sample or change in the assay conditions producing a similar result (e.g., concentration of reagents employed, etc.), and wherein the measured concentration of the analyte molecules may be substantially accurately determined. The concentration of analyte molecules in a fluid sample may be considered to be substantially accurately determined if the measured concentration of the analyte molecules in the fluid sample is within about 10% of the actual (e.g., true) concentration of the analyte molecules in the fluid sample. In certain embodiments, the measured concentration of the analyte molecules in the fluid sample is substantially accurately determined in embodiments where the measured concentration is within about 5%, within about 4%, within about 3%, within about 2%, within about 1%, within about 0.5%, within about 0.4%, within about 0.3%, within about 0.2%, or within about 0.1% of the actual concentration of the analyte molecules in the fluid sample. In some cases, the measure of the concentration determined differs from the true (e.g., actual) concentration by no greater than about 20%, no greater than about 15%, no greater than about 10%, no greater than about 5%, no greater than about 4%, no greater than about 3%, no greater than about 2%, no greater than about 1%, or no greater than about 0.5%. The accuracy of the assay method may be determined, in some embodiments, by determining the concentration of analyte molecules in a fluid sample of a known concentration using the selected assay method and comparing the measured concentration with the actual concentration.

In some embodiments, the systems or methods may be capable of measuring concentrations of analyte molecules in a fluid sample over a dynamic range of more than about 1000 (3 log), about 10,000 (4 log), about 100,000 (5 log), about 350,000 (5.5 log), 1,000,000 (6 log), about 3,500,000 (6.5 log), about 10,000,000 (7 log), about 35,000,000 (7.5 log), about 100,000,000 (8 log), or more.

In some embodiments, the concentration (e.g., unknown concentration) of analyte molecules in the fluid sample that may be substantially accurately determined is less than about 5000 fM (femtomolar), less than about 3000 fM, less than about 2000 fM, less than about 1000 fM, less than about 500 fM, less than about 300 fM, less than about 200 fM, less than about 100 fM, less than about 50 fM, less than about 25 fM, less than about 10 fM, less than about 5 fM, less than about 2 fM, less than about 1 fM, less than about 500 aM (attomolar), less than about 100 aM, less than about 10 aM, less than about 5 aM, less than about 1 aM, less than about 0.1 aM, less than about 500 zM (zeptomolar), less than about 100 zM, less than about 10 zM, less than about 5 zM, less than about 1 zM, less than about 0.1 zM, or less. In some cases, the limit of detection (e.g., the lowest concentration of an analyte molecule which may be determined in solution) is about 100 fM, about 50 fM, about 25 fM, about 10 fM, about 5 fM, about 2 fM, about 1 fM, about 500 aM (attomolar), about 100 aM, about 50 aM, about 10 aM, about 5 aM, about 1 aM, about 0.1 aM, about 500 zM (zeptomolar), about 100 zM, about 50 zM, about 10 zM, about 5 zM, about 1 zM, about 0.1 zM, or less. In some embodiments, the concentration of analyte molecules or particles in the fluid sample that may be substantially accurately determined is between about 5000 fM and about 0.1 fM, between about 3000 fM and about 0.1 fM, between about 1000 fM and about 0.1 fM, between about 1000 fM and about 0.1 zM, between about 100 fM and about 1 zM, between about 100 aM and about 0.1 zM, or less. The upper limit of detection (e.g., the upper concentration of an analyte molecule which may be determined in solution) is at least about 100 fM, at least about 1000 fM, at least about 10 pM (picomolar), at least about 100 pM, at least about 100 pM, at least about 10 nM (nanomolar), at least about 100 nM, at least about 1000 nM, at least about 10 uM, at least about 100 uM, at least about 1000 uM, at least about 10 mM, at least about 100 mM, at least about 1000 mM, or greater. In some embodiments, the concentration of analyte molecules or particles in the fluid sample determined is less than about $50\times10^{-15}$M, or less than about $40\times10^{-15}$M, or less than about $30\times10^{-15}$M, or less than about $20\times10^{-15}$M, or less than about $10\times10^{-15}$M, or less than about, or less than about $1\times10^{-15}$M.

In some embodiments, the concentration of analyte molecules in the sample that may be substantially accurately determined is less than about 100 fM, less than about 10 fM, less than about 3 fM, less than about 1 fM, less than about 0.3 fM, less than about 0.1 fM, less than about 0.03 fM, or less. In some embodiments, the concentration of analyte molecules in the sample that may be substantially accurately determined is between about 5000 fM and about 0.1 fM, between about 3000 fM and about 0.1 fM, between about 1000 fM and about 0.1 fM, between about 1000 fM and about 1 fM, between about 100 fM and about 1 fM, between about 100 fM and about 0.1 fM. The concentration of analyte molecules in a sample may be considered to be substantially accurately determined if the measured concentration of the analyte molecules in the sample is within about 20% of the actual concentration of the analyte molecules in the sample. In certain embodiments, the measured concentration of the analyte molecules in the sample may be within about 10%, within about 3%, or within about 1% of the actual concentration of the analyte molecules in the sample. The accuracy of the assay method may be determined, in some embodiments, by determining the concentration of analyte molecules in a sample of a known concentration using the selected assay method. Preferably the assay can detect approximately 10-10,000 molecules in a sample, preferably, 100-5,000 molecules in a sample, and more preferably, 100-1000 molecules in a sample.

Relative to a conventional sandwich immunoassay techniques, as measured, for example, using the same capture antibody and either one of the two detection antibodies and the same label and detection technology, the use of the assay formats described herein can improve detection signals and assay sensitivity by as much as 10-fold, preferably, as much as 50-fold, 100-fold, or as much as 1000-fold. Preferably, the use of the assay formats described herein improve detection signal and assay sensitivity by as much as 100-fold relative to a standard sandwich immunoassay.

One advantageous aspect of the methods of the invention, especially when coupled to a sensitive optical detection technique is that the signal amplification allows for the detection of individual binding event as bright points of light. Quantitation of signal, can then be carried out by counting the individual events (which can provide better sensitivity for low analyte concentrations by providing improved discrimination of binding events from background noise) or by integrating over the signal for all binding events (which can provide better dynamic range for measuring high analyte concentrations).

The methods of the present invention may be used in a variety of assay devices and/or formats. The assay devices may include, e.g., assay modules, such as assay plates, cartridges, multi-well assay plates, reaction vessels, test tubes, cuvettes, flow cells, assay chips, lateral flow devices, etc., having assay reagents (which may include targeting agents or other binding reagents) added as the assay progresses or pre-loaded in the wells, chambers, or assay regions of the assay module. These devices may employ a variety of assay formats for specific binding assays, e.g., immunoassay or immunochromatographic assays. Illustrative assay devices and formats are described herein below. In certain embodiments, the methods of the present invention may employ assay reagents that are stored in a dry state and the assay devices/kits may further comprise or be supplied with desiccant materials for maintaining the assay reagents in a dry state. The assay devices preloaded with the assay reagents can greatly improve the speed and reduce the complexity of assay measurements while maintaining excellent stability during storage. The dried assay reagents may be any assay reagent that can be dried and then reconstituted prior to use in an assay. These include, but are not limited to, binding reagents useful in binding assays, enzymes, enzyme substrates, indicator dyes and other reactive compounds that may be used to detect an analyte of interest. The assay reagents may also include substances that are not directly involved in the mechanism of detection but play an auxiliary role in an assay including, but not limited to, blocking agents, stabilizing agents, detergents, salts, pH buffers, preservatives, etc. Reagents may be present in free form or supported on solid phases including the surfaces of compartments (e.g., chambers, channels, flow cells, wells, etc.) in the assay modules or the surfaces of colloids, beads, or other particulate supports.

The methods of the invention can be used with a variety of methods for measuring the amount of an analyte and, in particular, measuring the amount of an analyte bound to a solid phase. Techniques that may be used include, but are not limited to, techniques known in the art such as cell culture-based assays, binding assays (including agglutination tests, immunoassays, nucleic acid hybridization assays, etc.), enzymatic assays, colorometric assays, etc. Other suitable techniques will be readily apparent to one of average skill in the art. Some measurement techniques allow for measurements to be made by visual inspection, others may require or benefit from the use of an instrument to conduct the measurement.

Methods for measuring the amount of an analyte include label-free techniques, which include but are not limited to i) techniques that measure changes in mass or refractive index at a surface after binding of an analyte to a surface (e.g., surface acoustic wave techniques, surface plasmon resonance sensors, ellipsometric techniques, etc.), ii) mass spectrometric techniques (including techniques like MALDI, SELDI, etc. that can measure analytes on a surface), iii) chromatographic or electrophoretic techniques, iv) fluorescence techniques (which may be based on the inherent fluorescence of an analyte), etc.

Methods for measuring the amount of an analyte also include techniques that measure analytes through the detection of labels which may be attached directly or indirectly (e.g., through the use of labeled binding partners of an analyte) to an analyte. Suitable labels include labels that can be directly visualized (e.g., particles that may be seen visually and labels that generate an measurable signal such as light scattering, optical absorbance, fluorescence, chemiluminescence, electrochemiluminescence, radioactivity, magnetic fields, etc). Labels that may be used also include enzymes or other chemically reactive species that have a chemical activity that leads to a measurable signal such as light scattering, absorbance, fluorescence, etc. The use of enzymes as labels has been well established in in Enzyme-Linked ImmunoSorbent Assays, also called ELISAs, Enzyme ImmunoAssays or EIAs. In the ELISA format, an unknown amount of antigen is affixed to a surface and then a specific antibody is washed over the surface so that it can bind to the antigen. This antibody is linked to an enzyme, and in the final step a substance is added that the enzyme converts to a product that provides a change in a detectable signal. The formation of product may be detectable, e.g., due a difference, relative to the substrate, in a measurable property such as absorbance, fluorescence, chemiluminescence, light scattering, etc. Certain (but not all) measurement methods that may be used with solid phase binding methods according to the invention may benefit from or require a wash step to remove unbound components (e.g., labels) from the solid phase Accordingly, the methods of the invention may comprise such a wash step.

In those embodiments that employ a pair of detectable labels, those labeled substances are selected based on their ability to be independently detectable and/or the ability of those substances to work in concert to generate a detectable signal when the pair of labels are in proximity to one another, i.e., each bound, directly or indirectly, to the analyte of interest in a detection complex. In one embodiment, the first detectable label is a first enzyme of a coupled enzyme reaction system and the second detectable label is a second enzyme of the couple enzyme reaction system and the method further includes the step of adding one or more substrates of the reaction system, thereby producing a detectable product of the enzyme reaction system. Those reaction vessels that include the detectable product can be distinguished from those reaction vessels that do not. In a preferred embodiment, the detectable product is only produced when the first enzyme and second enzyme are in close proximity, e.g., less than 200 nm, ideally less than 50 nm. In one embodiment, the first enzyme is an oxidase, e.g., a glucose oxidase, the second enzyme is a peroxidase, and the substrates comprise an oxidase substrate, e.g., glucose, and a labeled tyramide, Amplex Red (10-acetyl-3,7-dihydroxyphenoxazine), or luminol derivative (referred to collectively herein as a labeled reactive derivative and in a preferred embodiment, the labeled reactive derivative comprises Amplex Red or luminol). In this embodiment, the first enzyme reacts with a substrate to generate a product that reacts with the second enzyme to generate a second product that reacts with the labeled reactive derivative to generate a detectable species. Preferably, the reactions catalyzed by the first and second enzymes in the detection complex lead to immobilization of the labeled reactive derivative on the surface, which may be measured to determine the number of analyte molecules present on the surface. In one embodiment, the labeled reactive derivative is biotin-tyramide, and the method further comprises adding labeled streptavidin and measuring the labels on the streptavidin.

Yet another proximity-dependent labeling system that can be used in the method is a FRET pair, e.g., the first detectable label is a FRET donor and the detectable label is a FRET acceptor. Fluorescence resonance energy transfer (FRET) is a distance-dependent interaction between the electronic excited states of two dye molecules in which excitation is transferred from a donor molecule to an acceptor molecule without emission of a photon. The efficiency of FRET is dependent on the inverse sixth power of the intermolecular separation, making it useful over distances comparable to the dimensions of biological macromolecules. In this labeling system, the proximity-dependent signal is measured by exciting the FRET donor and measuring emission from the FRET acceptor. Donor and acceptor molecules are preferably in close proximity, e.g., about 10-100 Angstroms, the absorption spectrum of the acceptor preferably overlaps with the fluorescence emission spectrum of the donor, and the donor and acceptor transition dipole orientations should be approximately parallel. A non-limiting list of FRET pairs are provided in Table 1 below.

TABLE 1

FRET Pair Examples

| Donor | Acceptor |
| --- | --- |
| Fluorescein | Tetramethylrhodamine |
| IAEDANS | Fluorescein |
| EDANS | Dabcyl |
| Fluorescein | Fluorescein |
| BODIPY FL | BODIPY FL |
| Fluorescein | QSY 7 and QSY 9 dyes |

A variety of FRET detection methods exist for light microscopy, e.g., acceptor photobleaching, donor photobleaching, ratio imaging, sensitized emission, and fluorescence lifetime measurements.

Another suitable labeling system that can be used in an embodiment employing a pair of detection labels is a system in which the first and second detectable labels can be measured independently. For example, the first and second detectable labels can be luminescent labels that differ from one another with respect to spectral properties. Alternatively, the first detectable label is a first enzyme that reacts with a first substrate to produce a first signal and the second detectable label is a second enzyme that reacts with a second substrate to produce a different second signal, and the method further comprises adding the first enzyme substrate and the second enzyme substrate and counting the number of reaction vessels in which the first and second signals are generated. The first and second signal can be changes in optical absorbance and/or luminescent signals with different spectral properties.

If the first and second detectable labels include first and second enzymes, they can each be hydrolytic enzymes, e.g., a phosphatase, sulfatase, galactosidase, glucuronidase, or combinations thereof, and therefore, the first and second substrates are selected from phosphate, sulfate, galactoside and glucuronide modified stabilized dioxetanes, 4-methylumbelliferyl, fluorescein, or combinations thereof. Alternatively, the first and second enzymes are selected from horseradish peroxidase, beta-galactosidase, and alkaline phosphatase.

Alternatively, labels used to detect analyte molecules can be fluorescent species that can be used in single molecule fluorescence detection, e.g., fluorescence correlation spectroscopy, and/or fluorescence cross-correlation spectroscopy. Single molecule fluorescence detection comprises flowing an eluent that includes a detectable species through a capillary, focusing a light source on a volume within the capillary to create an interrogation zone and observing the interrogation zone with a light detector to detect the passage of fluorescent molecules through the interrogation zone.

In one embodiment, an analyte(s) of interest in the sample may be measured using electrochemiluminescence-based assay formats, e.g. electrochemiluminescence (ECL) based immunoassays. The high sensitivity, broad dynamic range and selectivity of ECL are important factors for medical diagnostics. Commercially available ECL instruments have demonstrated exceptional performance and they have become widely used for reasons including their excellent sensitivity, dynamic range, precision, and tolerance of complex sample matrices. Species that can be induced to emit ECL (ECL-active species) have been used as ECL labels, e.g., i) organometallic compounds where the metal is from, for example, the noble metals of group VIII, including Ru-containing and Os-containing organometallic compounds such as the tris-bipyridyl-ruthenium (RuBpy) moiety and ii) luminol and related compounds. Species that participate with the ECL label in the ECL process are referred to herein as ECL coreactants. Commonly used coreactants include tertiary amines (e.g., see U.S. Pat. No. 5,846,485), oxalate, and persulfate for ECL from RuBpy and hydrogen peroxide for ECL from luminol (see, e.g., U.S. Pat. No. 5,240,863). The light generated by ECL labels can be used as a reporter signal in diagnostic procedures (Bard et al., U.S. Pat. No. 5,238,808, herein incorporated by reference). For instance, an ECL label can be covalently coupled to a binding agent such as an antibody, nucleic acid probe, receptor or ligand; the participation of the binding reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants). For more background on ECL, ECL labels, ECL assays and instrumentation for conducting ECL assays see U.S. Pat. Nos. 5,093,268; 5,147,806; 5,324,457; 5,591,581; 5,597,910; 5,641,623; 5,643,713; 5,679,519; 5,705,402; 5,846,485; 5,866,434; 5,786,141; 5,731,147; 6,066,448; 6,136,268; 5,776,672; 5,308,754; 5,240,863; 6,207,369; 6,214,552 and 5,589,136 and Published PCT Nos. WO99/63347; WO00/03233; WO99/58962; WO99/32662; WO99/14599; WO98/12539; WO97/36931 and WO98/57154, all of which are incorporated herein by reference.

The methods of the invention may be applied to single-plex or multiplex formats where multiple assay measurements are performed on a single sample. Multiplex measurements that can be used with the invention include, but are not limited to, multiplex measurements i) that involve the use of multiple sensors; ii) that use discrete assay domains on a surface (e.g., an array) that are distinguishable based on location on the surface; iii) that involve the use of reagents coated on particles that are distinguishable based on a particle property such as size, shape, color, etc.; iv) that produce assay signals that are distinguishable based on optical properties (e.g., absorbance or emission spectrum) or v) that are based on temporal properties of assay signal (e.g., time, frequency or phase of a signal).

In some embodiments, a measure of the concentration of analyte molecules in the sample may be determined at least in part by comparison of a measured parameter to a calibration standard. For example, the fraction of binding surfaces that comprise an analyte molecule may be compared against a calibration curve to determine a measure of the concentration of the analyte molecule in the sample. The calibration curve may be produced by completing the assay with a plurality of standardized samples of known concentration under the conditions used to analyze the test samples. A reading may be taken for the signal related to the detection/quantification of the analyte molecules for each standardized sample, therefore allowing for the formation of a calibration curve relating the detection of the analyte molecules with a known concentration of the analyte molecule. The assay may then be completed on a sample comprising the analyte molecule in an unknown concentration, and the detection of the analyte molecules from this assay may be plotted on the calibration curve, therefore determining a measure of the concentration of the analyte molecule in the sample.

In the specific case of using an imaging technique to measure an optical signal (such as fluorescence, chemiluminescence or electrochemiluminescence) a binding event can be detected as a bright point source of light. When the surface density of point sources is low (e.g., when the probability of finding a point source in an R×R area—where R is the spatial resolution of the detection system—is less than 10%), it is likely that any observed point source is due to a single binding event. Under these conditions, counting events can provide the most sensitive measurement. As the surface density increases, it becomes increasingly difficult to resolve and count individual binding events. Under these conditions, integrating the optical signal over the binding surface provides a more accurate measurement.

It will be evident to the skilled artisan that the methods described herein can be applied to numerous immunoassay platforms known to those skilled in the art. Various features of the immunoassay platforms may be adjusted to suit the particular platform, but those adjustments are well within the skill of the ordinary artisan. For example, the methods described herein can be applied to a bead-based format that uses coded particles. In such a system, the bead used can be magnetic or non-magnetic and the surface of the beads is modified to include one or more copies of a capture reagent. The detection reagents employed in this system are a pair of detection reagents. In one embodiment, the two detection reagents include distinguishable fluorescent labels. Alternatively, the two detection reagents are modified with nucleic acid probes, as described herein, in which case, the immunoassay method includes an extension process, e.g., RCA-PLA to generate an amplified product indicative of the presence of each detection reagent that can be detected. If the detection reagents include two distinguishable fluorescent labels, the measurement step includes introducing the beads into a flow cell, and if the beads are magnetic, capturing the beads in the flow cell. If the detection reagents are modified with nucleic acid probes, the measurement step includes forming a sandwich complex on the beads, performing RCA-PLA and labeling the amplicon with fluorescently labeled detection probes. The labeled beads are then introduced into the flow cell and if the beads are magnetic, the beads are captured in the flow cell. In each embodiment, the assay can be multiplexed spectrally based on the identification of fluorescently labeled encoded beads. An excitation light source and emission light detector for multi-color detection can be used to detect binding events in each embodiment, quantitation is achieved by counting beads having both detectable labels or those beads that include a detectably labeled extension product, and quantitation is also achieved by integrated intensity, e.g., detection by integrating over the signal for all binding events. Therefore, a kit can be provided for use with the method described above that includes one or more of the following in one or more vials, containers, or compartments: (a) Magnetic or non-magnetic beads with capture reagent; (b) two detection reagents with distinguishable fluorescent labels; and (c) Optional buffers and/or diluents for assay protocol. Another kit that can be used with the method described above can include one or more of the following on one or more vials, containers, or compartments: (a) Magnetic or non-magnetic beads with capture reagent; (b) Two detection reagents modified with nucleic acid probes (optionally, detection reagents are provided separately and proximity probes (1 and 2) are additionally provided with instructions to modify detection reagents with probes); and (c) fluorescently labeled probes; optional reagents required for modification of detection reagents with proximity probes; assay diluent, calibrator, circularization oligonucleotides, ligation mix or components thereof, e.g., ligation buffer, ATP, BSA, Tween 20, T4 DNA ligase; RCA mixture or components thereof, e.g., BSA, buffer, dNTP, Tween 20, Phi29 DNA polymerase.

In another embodiment, the methods described herein can be applied to a flow-cell analyzed, bead-based format. In such a system, the bead used can be magnetic and the surface of the beads is modified to include one or more copies of a capture reagent. The detection reagents employed in this system are a pair of detection reagents modified with nucleic acid probes, as described herein, in which case, the immunoassay method includes an extension process, e.g., RCA-PLA to generate an amplified product indicative of the presence of each detection reagent that can be detected. The measurement step includes forming a sandwich complex on the beads, performing RCA-PLA and labeling the amplicon with ECL-labeled detection probes. The labeled beads are then introduced into the flow cell and the beads are captured in the flow cell. In particular, a magnetic field is applied to draw the magnetic particles, e.g., beads, to the electrode surface, which can comprise various metals, e.g., platinum. A voltage source is used to apply a voltage to an electrode and an emission light detector can be used to detect binding events; quantitation is achieved by counting beads having a detectably labeled extension product, and quantitation is also achieved by integrated intensity, e.g., detection by integrating over the signal for all binding events. A kit that can be used with the method described above can include one or more of the following on one or more vials, containers, or compartments: (a) Magnetic beads with capture reagent; (b) Two detection reagents modified with nucleic acid probes (optionally, detection reagents are provided separately and proximity probes (1 and 2) are additionally provided with instructions to modify detection reagents with probes); and (c) ECL labeled probes; optional reagents required for modification of detection reagents with proximity probes; assay diluent, calibrator, circularization oligonucleotides, ligation mix or components thereof, e.g., ligation buffer, ATP, BSA, Tween 20, T4 DNA ligase; RCA mixture or components thereof, e.g., BSA, buffer, dNTP, Tween 20, Phi29 DNA polymerase.

In a specific embodiment of a flow-cell analyzed, bead-based format, a sample is incubated with a biotinylated monoclonal analyte-specific capture antibody and a mixture of monoclonal analyte-specific antibodies, each conjugated to oligonucleotides, which react to form a sandwich complex. After the addition of streptavidin-coated microparticles, the complex becomes bound to the solid phase via interactions between biotin and streptavidin. A ligation mix is added to the mixture, and the mixture is incubated with the ligation mix, washed to remove excess circularization oligonucleotides, and incubated with RCA mixture. The mixture is washed and a mixture of biotin-labeled detection probes are added. To incorporate a suitable label, e.g., a luminescent, chemiluminescent, or electrochemiluminescence label, e.g., SULFO-TAG™, the detection probe is synthesized with a terminal biotin label and pre-bound to SULFO-TAG™ labeled streptavidin. The reaction mixture is aspirated into the measuring cell where the microparticles are magnetically captured onto the surface of the electrode, e.g., a metal electrode, such as a platinum electrode. Unbound substances are then removed with a suitable wash buffer, e.g., ProCell (TPA containing buffer). Application of a voltage to the electrode then induces chemiluminescent emission which is measured by a photomultiplier. The application of voltage and measurement of the resultant emission can be done in any suitable flow-cell, e.g., a Cobas and/or Elecsys instrument (available from Hoffmann-La Roche LTD.).

In yet another embodiment, the methods described herein can be applied to a bead-based format, with capillary flow to digitally count individual molecules. In such a system, the bead used can be magnetic and the surface of the bead is modified to include one or more copies of a capture reagent. The detection reagents employed in this system are a pair of detection reagents that include distinguishable fluorescent labels. The measurement step includes forming a sandwich complex including the capture reagent, analyte, and detection reagents, crosslinking detection reagents, eluting detection reagents and introducing the beads into a flow cell. An excitation light source and emission light detector for multi-color detection can be used to detect binding events, quantitation is achieved by correlating detection of two fluorophores in the flow cell, and quantitation is also achieved by integrated intensity, e.g., detection by integrating over the signal for all binding events. A kit that can be used with the method described above can include one or more of the following on one or more vials, containers, or compartments: (a) Magnetic beads with capture reagent; (b) Two cross-linkable detection reagents with distinguishable fluorescent labels; and (c) Optional buffers and/or diluents for assay protocol.

Moreover, the methods described herein can be applied to a bead-based format that includes the separation of beads into individual nanowells. In such a system, the bead used can be magnetic and the surface of the bead is modified to include one or more copies of a capture reagent. The detection reagents employed in this system are a pair of detection reagents that include distinguishable enzyme labels. The measurement step includes forming a sandwich complex including the capture reagent, analyte, and detection reagents, and adding substrates for the two enzyme labels. The beads are then captured in individual nanowells. The assay can be multiplexed spectrally based on the identification of enzyme products with different spectral properties. An excitation light source and emission light detector for multi-color detection can be used to detect binding events, quantitation is achieved by counting nanowells that contain both enzyme products, and quantitation is also achieved by integrated intensity, e.g., detection by integrating over the signal for all nanowells. A kit that can be used with the method described above can include one or more of the following on one or more vials, containers, or compartments: (a) Magnetic beads with capture reagent; (b) Two detection reagents each modified with distinguishable enzyme labels, e.g., biotinylated detection reagent and a hapten-conjugated detection reagent; (c) Streptavidin-beta galactosidase, anti-hapten conjugated enzyme, resorufin-beta-d-galactopyranoside; (d) array, e.g., Quanterix DVD format array; (e) fluorocarbon oil; and (f) optional buffers and/or diluents for assay protocol. In this specific embodiment, the detectable signal is enhanced by combining the use of a nanowell high-sensitivity system with a proximity-based detection system. While this specific embodiment is illustrated using a particular proximity-based detection system, the skilled artisan will appreciate the fact that the other proximity-based detection systems described herein can also be used to enhance the detectable signal in the assay, e.g., FRET donor/acceptor system; luminescent labels that differ from one another with respect to spectral properties; or the use of first and second enzymes that are hydrolytic enzymes, as described above, and the appropriate accompanying substrates.

Still further, the methods described herein can be applied to a bead-array based platform. In such a system, the bead used can be non-magnetic and the surface of the bead is modified to include one or more copies of a capture reagent. The detection reagents employed in this system are a pair of detection reagents that include first and second nucleic acid probes. The measurement step includes forming a sandwich complex including the capture reagent, analyte, and detection reagents, extending one of the probes to form an extended sequence, wherein extension is dependent on co-localization of the first and second probes in the sandwich complex, labeling the extended sequence with a fluorescent probe, and releasing the extended sequence from the surface into an eluent. An excitation light source and emission light detector for multi-color detection can be used to detect binding events, quantitation is achieved by counting individual detectably labeled extension products, and quantitation is also achieved by integrated intensity, e.g., detection by integrating over the signal for all binding events. A kit that can be used with the method described above can include one or more of the following on one or more vials, containers, or compartments: (a) Non-magnetic beads with capture reagent; (b) Two detection reagents modified with nucleic acid probes (optionally, detection reagents are provided separately and proximity probes (1 and 2) are additionally provided with instructions to modify detection reagents with probes); and (c) Fluorescently labeled probes; optional reagents required for modification of detection reagents with proximity probes; assay diluent, calibrator, circularization oligonucleotides, ligation mix or components thereof, e.g., ligation buffer, ATP, BSA, Tween 20, T4 DNA ligase; RCA mixture or components thereof, e.g., BSA, buffer, dNTP, Tween 20, Phi29 DNA polymerase.

The improved binding assays described herein can be performed using one or more kits including a set of components employed in the assay. For example, a kit used in the detection of an analyte in a sample includes, in one or more vials, containers, or compartments, a surface including a capture reagent for the analyte and an anchoring reagent; and a detection reagent for the analyte that is linked to a nucleic acid probe. Such a kit may include an anchoring reagent comprising an anchoring oligonucleotide sequence.

Another kit that can be used to carry out the methods described herein includes, in one or more vials, containers, or compartments, a surface comprising a capture reagent for the analyte and an anchoring reagent comprising an anchoring oligonucleotide sequence; a first detection reagent linked to a first nucleic acid probe; and a second detection reagent linked to a second nucleic acid probe.

Yet another kit that can be used to perform the binding assays described herein includes, in one or more vials, containers, or compartments, a surface comprising a capture reagent for the analyte and an anchoring reagent; a first detection reagent for the analyte comprising a first proximity probe; a second detection reagent for the analyte comprising a second proximity probe; and a connector sequence comprising (i) an interior sequence complementary to the second proximity probe and (ii) two end sequences complementary to non-overlapping regions of the first proximity probe. Alternatively, a kit may instead include a surface comprising a capture reagent for the analyte, and an anchoring reagent; a first detection reagent for the analyte comprising a first proximity probe; a second detection reagent for the analyte comprising a second proximity probe; and (i) a first connector oligonucleotide and (ii) a second connector oligonucleotide, wherein (x) a first end of the first connector and a first end of the second connector are complementary to two non-overlapping regions of the first proximity probe and (y) a second end of the first connector and a second end of the second connector are complementary to two non-overlapping regions of the first proximity probe. In addition, the anchoring reagents in either or both of these kits can include an anchoring oligonucleotide sequence.

Moreover, the methods described herein can be performed using a kit including, in one or more vials, containers, or compartments, a first detection reagent comprising a first detectable label; a second detection reagent comprising a second detectable label; a plurality of reaction vessels configured to contain one or fewer analyte molecules; and optionally, a surface comprising a capture reagent.

Finally, a kit for the detection of an analyte using the methods described herein can include, in one or more vials, containers, or compartments, a surface comprising an immobilized capture reagent; a first detection reagent having a first detectable label; a second detection reagent having a second detectable label; and a cross-linking agent reactive with the first and second detection reagents. The cross-linking agent can include a multifunctional cross-linking agent that links reactive moieties attached to the detection reagents or a multivalent binding partner of binding moieties attached to the detection reagents. Suitable multi-functional cross-linking agents include but are not limited to, amines, thiols, hydrazides, aldehydes, esters, iodoacetamides, maleimides, click chemistry reagents, and combinations thereof. Likewise, an example of a multivalent binding partner is a multivalent anti-species antibody targeting detection reagents that are antibodies of that animal species. The cross-linking agent can also include streptavidin, avidin, or biotin, when paired with a companion binding partner attached to the detection reagents. The cross-linking agent can also be an oligonucleotide including a sequence complementary to a nucleic acid probe bound, directly or indirectly, to a component of the kit. In a specific embodiment a kit used in the methods described herein includes, in one or more vials, containers, or compartments, a surface comprising an immobilized capture reagent; a first detection reagent having a first detectable label and a first nucleic acid probe; a second detection reagent having a second detectable label and a second nucleic acid probe; and a third nucleic acid having regions complementary to the first and second nucleic acid probes.

The surfaces of the kits described herein can include a plurality of capture reagents for one or more analyte molecules, wherein the capture reagents are distributed across a plurality of resolvable binding regions or reaction vessels positioned on the surface, e.g., in an array, a multi-well plate, or a micro- or nano-well plate. In addition, the surface can also include a plurality of particles each comprising a plurality of capture reagents for an analyte molecule.

The kits described hereinabove can further include one or more of the following: one or more additional reagents, buffers, polymerase, ligase, and/or dNTPs (labeled or unlabeled). In addition, if the one or more detection reagents comprise a detectable label, the kit can also include a co-reactant for the detectable label employed in the kit. Alternatively, if the one or more detection reagents are components of a coupled enzyme reaction system, then each of the detection reagents comprise first and second enzymes and the kit further includes, in one or more containers, vials or compartments, one or more substrates for the coupled enzyme reaction system, and optionally, a labeled component configured to bind to a product of the coupled enzyme reaction system. For example, the first enzyme can be an oxidase, the second enzyme a peroxidase, and the kit further includes an oxidase substrate and a labeled tyramide derivative. In another embodiment, the first and second detectable reagents can be comprise components of a proximity-dependent detection system, e.g., a FRET donor and a FRET acceptor, or luminescent labels that differ from one another with respect to their spectral properties.

Additional Alternative Embodiments

A further embodiment is illustrated in FIG. 7. A portion of each of the proximity probes in the sandwich immunoassay complex in panel (a) are temporarily protected by short strands of RNA hybridized to each segment. The RNA strands are enzymatically removed so that each of the proximity probes can hybridize to one another and the chain is extended by polymerase extension using biotinylated dNTPs (panel (b)). Each biotinylated base incorporated into the chain is bound to streptavidin labeled with a detectable label (panel (c)).

Yet another approach is illustrated in FIG. 8. Proximity probes can be attached to the anchoring reagent and a detection reagent (as shown in panel (a)) or each of the proximity probes can be attached to two detection reagents as described hereinabove (not shown). Much like the method illustrated in FIG. 7, a portion of each of the proximity probes are temporarily protected by short strands of RNA hybridized to each segment. The RNA strands are enzymatically removed so that each of the proximity probes can hybridize to one another and the chain is extended by polymerase extension using biotinylated dNTPs (panel (b)). Each biotinylated base incorporated into the chain is bound to streptavidin labeled with a detectable label (panel (c)).

Figure 18:
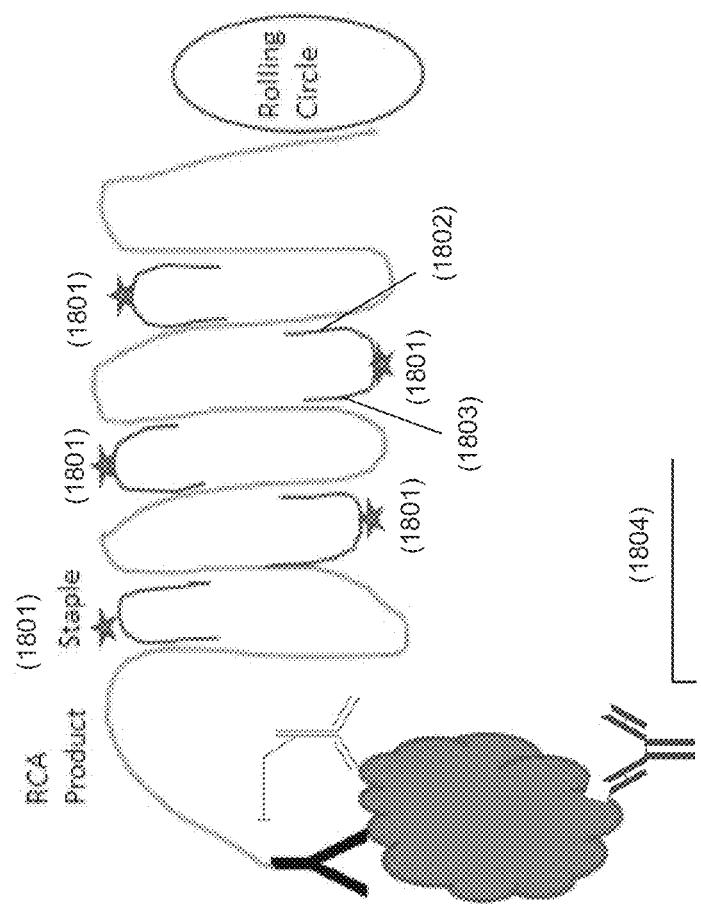
FIG. 18 is a schematic representation of an assay method that incorporates the use of a plurality of staple sequences to adhere to the amplicon, thereby forming a more compact structure on the surface.

An additional embodiment is shown in FIG. 18. In this embodiment, a plurality of short oligonucleotides are used as staple sequences (1801) to hybridize to a portion of the amplicon and thereby fold the product into a compact structure that is easily imaged. Each staple sequence comprises at least two sequences (1802 and 1803, respectively) that are each complimentary to a sequence of the amplicon and when each staple sequence hybridizes to its complement, the amplicon is folded back onto itself as shown in FIG. 18. In addition, the amplicon can also be adhered to the surface via an anchoring interaction with an anchoring reagent (1804) as described herein above. The stapling process can be performed in situ by adding the staple sequences to the reaction mixture during the amplification step. Therefore, as each cycle of amplification is completed, the staple sequences are free to hybridize to the newly formed amplicon and cause it to fold. The staples can also be added after the amplification process is completed, causing the linear amplicon to fold into a coil or flat sheet, depending on the design of the staple sequences and their corresponding complements. The label molecule, e.g., ECL or fluorescence, can be incorporated into the staple sequence (or it may be incorporated into the amplicon as described above). This embodiment would yield a three dimensional structure on the surface, producing smaller features of higher signal density which allows for easier imaging of the amplicons on the surface.

EXAMPLES

Example 1. General Protocol for Proximity Ligation and Rolling Circle Amplification A pair of detection antibodies to a target analyte was modified by the addition of proximity probes 1 and 2 as follows: to 200 ug first detection antibody in 100 uL buffer, 1.74 uL 23 mM sulfo-SMCC was added, diluted in 150 mM Phosphate buffer, and incubated at room temperature for 30 minutes. Free sulfo-SMCC was removed by size exclusion chromatography. The final concentration of the detection antibody was 2 mg/mL or slightly lower. Ninety-five (95) uL of 300 uM thiol-modified oligonucleotide (proximity probe 1 and 2) was reduced with 5 uL of 1 mM DTT in 100 mM phosphate buffer, 0.5 mM EDTA, pH 8.4, for 1 hour at room temperature. The sequences of proximity probes 1 and 2 are:

```
                        (SEQ ID No. 1; wherein the three U resides are 2'
                                                         O-methyl RNA)
Thiol-modified proximity probe 1: SH-AAA AAA AAA

AGA CGC TAA TAG TTA AGA CGC TTU UU (SEQ ID No. 2)
Thiol-modified proximity probe 2: SH-AAA AAA AAA

ATA TGA CAG AAC TAG ACA CTC TT.
```

Excess Sulfo-SMCC and DTT were removed, e.g., by using three spin column separates and antibody and DNA were pooled for covalent conjugation. The solution was incubated for 1 hour at room temperature with mixing. Antibody-proximity probe conjugates were purified, e.g, by size exclusion chromatography to remove unconjugated antibodies and oligonucleotides.

An MSD Technology MULTI-SPOT® plate was blocked for 1 hour with appropriate MSD® blocking solution and washed. Each binding domain on the plate included a capture antibody and an anchoring moiety (immobilized as a BSA-oligonucleotide conjugate, the oligonucleotide selected to be specific for a rolling circle amplicon). The sequence of the anchoring oligonucleotide used in this example was 5'-AAGAGAGTAGTACAGCAGCCGT-CAAAAAAAAAAAA-/3ThioMC3-D/-3'(SEQ ID NO: 3). Twenty-five (25) µl each assay diluent and calibrator, or sample (diluted as appropriate) (resulting in 50 ul total volume) was added to each well. The plate was incubated with shaking for 1-3 hours and each well was washed. A solution of detection antibodies labeled with proximity probes 1 and 2, prepared as described above, was added to each well (25 uL per well), and incubated with shaking for 1-2 hours (alternatively, each individual detection antibody can be sequentially added, with each addition followed by a 1 hour incubation). A ligation mix was added to each well including the following components: (i) circularization oligonucleotide 1 (4 nM), circularization oligonucleotide 2 (4 nM), ligation buffer, ATP (1 mM), T4 DNA ligase (0.15 U/uL), wherein the each of the circularization oligonucleotides were:

```
                                                 (SEQ ID No. 4)
Circularization oligonucleotide I: Phosphate-CTA

TTA GCG TCC AGT GAA TGC GAG TCC GTC TAA GAG AGT

AGT AGA GCA GCC GTC AAG AGT GTC TA.

(SEQ ID No. 5)
Circularization oligonucleotide 2: Phosphate-GTT

CTG TCA TAT TTA AGC GTC TTA A.
```

The plate was incubated with the ligation mix for 30 minutes at room temperature, washed to remove excess circularization oligonucleotides, and incubated with RCA mixture for 1.5 hour at 37 C, wherein the RCA mixture contained RCA buffer, dNTP (250 uM of each), Phi29 DNA polymerase (0.125 U/ml). The plate was washed and a mixture of detection probes were added and incubated for 30 minutes at 37 C, wherein the detection probe mixture includes: 20 mM Tris, 1 mM SDTA, 250 mM NaCl, 0.01% Triton, BSA (200 ug/ml), Tween 20 (0.05%), detection probes (6.25 nM). The detection probe was the sequence CAG TGA ATG CGA GTC CGT CT (SEQ ID NO: 6). To incorporate the electrochemiluminescence label SULFO-TAG™ (Meso Scale Diagnostics), the detection probe was synthesized with a terminal biotin label and was pre-bound to SULFO-TAG™ labeled streptavidin. The plate was washed and filled with 150 µl MSD read buffer and read immediately on MSD SECTOR® 6000 Plate Reader (plates and reader supplied by Meso Scale Discovery, Rockville, Md.).

Figure 9:
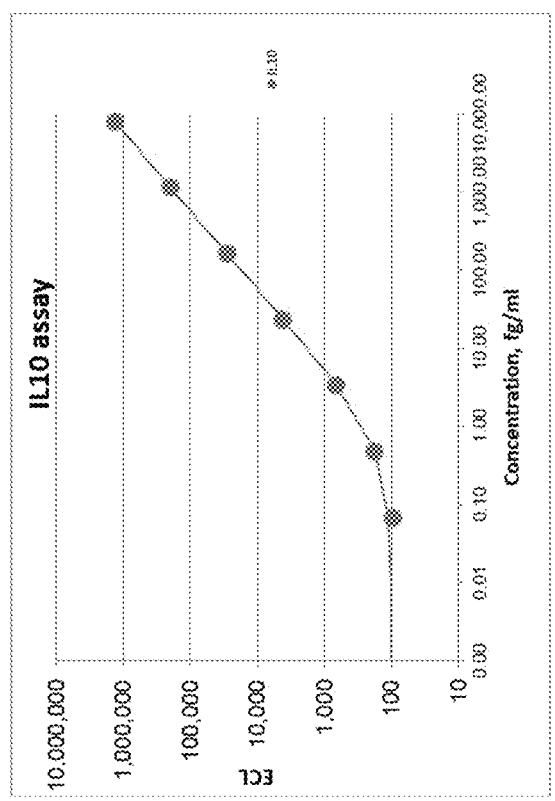
FIG. 9 shows a calibration curve for an IL-10 assay conducted using the method described in Example 1.

This general procedure was used to detect the following analytes: troponin I, Akt (total), phospho-Akt (473), phospho-Akt (308), Influenza A nucleoprotein (NP), IL-12p40, IL-12p70, Abeta1-42, bridging and isotyping Ig assays using TNFalpha model system, bridging and isotyping Ig assays using Hepatitis B surface antigen, and bridging and isotyping Ig assays using Lyme C6. The increases in ECL signal and assay sensitivity relative to a standard sandwich immunoassay varied between assays, but improvements as high as 100-fold were observed. For certain assays tested, e.g., Troponin-I, Akt (total), IL-12p40, IL-12p70, and Abeta1-42, the presence of anchoring moiety improved signal and/or dilution linearity, by preventing the dissociation of the detection complex during the amplification step. A calibration curve for an IL-10 assay conducted according to the procedure described above is shown in FIG. 9. In addition, Table 2 (below) shows the LOD for a set of representative assays conducted according to the procedure described above (column 2, "3-AB RCA/PLA Assay") relative to the LOD for a standard two antibody immunoassay protocol from Meso Scale Diagnostics (MSD), Rockville, Md., www.mesoscale.com (column 3, "MSD V-Plex 2-AB Immunoassay protocol").

TABLE 2

| Analyte | 3-AB RCA/PLA Assay LOD (fg/mL) | MSD V-Plex 2-AB Immunoassay protocol (fg/mL) |
| --- | --- | --- |
| IL-1b | 2-5 | 80 |
| IL-2 | 4 | 180 |
| IL-4 | 0.7 | 40 |
| IL-6 | 0.6 | 120 |
| IL-10 | 2 | 60 |

Example 2. Assay Protocol with and without Anchoring Reagent

An MSD 7-spot MULTI-SPOT® plate was coated as described above in Example 1 with Troponin I capture antibodies (220 ug/mL) each. Capture antibodies were co-spotted with or without an anchoring moiety, BSA, to which an oligonucleotide specific for an amplicon was covalently attached (5 ug/mL anchor, if present). Twenty five (25) µl each assay diluent, calibrator, or sample (diluted as appropriate) was added to each well (50 ul total). The plate was incubated with shaking for 2 hours and each well was washed. A solution of detection antibodies labeled with proximity probes 1 and 2, prepared as described above, was added to each well (25 uL per well), and incubated with shaking for 1 hour. A ligation mix was added to each well as described above in Example 1. The plate was incubated with the ligation mix for 30 minutes at room temperature, washed to remove excess circularization oligonucleotides, and incubated with RCA mixture for 1.5 hour at 37 C as described above in Example 1. The plate was washed and a mixture of detection probes were added and incubated for 30 minutes at 37 C as described above in Example 1. The plate was washed and filled with 150 µl MSD read buffer and read immediately on MSD SECTOR® 6000 Plate Reader. The MSD electrode was removed from the plate top for fluorescence imaging and kept wet with PBS and a cover slip. The surface was viewed on a microscope with a Zyla camera, 20× objective, 2×2 binning, customer filter set, with a 2 second exposure.

As shown in Table 3 (below), ECL values were 4-5 times higher in the presence of the anchoring reagent and the detection limit was three times lower (more sensitive).

TABLE 3

| Cal Conc (pg/ml) | +Anchor | No Anchor |
| --- | --- | --- |
| 500 | 134,705 | 29,818 |
| 50 | 12,713 | 2,486 |
| 5 | 1,121 | 270 |
| 0.5 | 150 | 60 |
| 0.05 | 92 | 43 |
| 0.005 | 40 | 86 |
| 0.0005 | 56 | 30 |
| 0 | 71 | 37 |
| Detection Limit | 0.36 | 1.16 |

FIGS. 10 (a) and (b) show fluorescence microscopy images of plate surfaces with 5 ug/mL anchoring reagent (panel (a)) and without (panel (b)). The image shows bright fluorescent spots associated with individual binding events and confirms that RCA amplification in the presence of the anchor reagent was more efficient at generating observable binding events.

Example 3. Comparison of One Vs. Two Connector Oligonucleotides

Figure 11A:
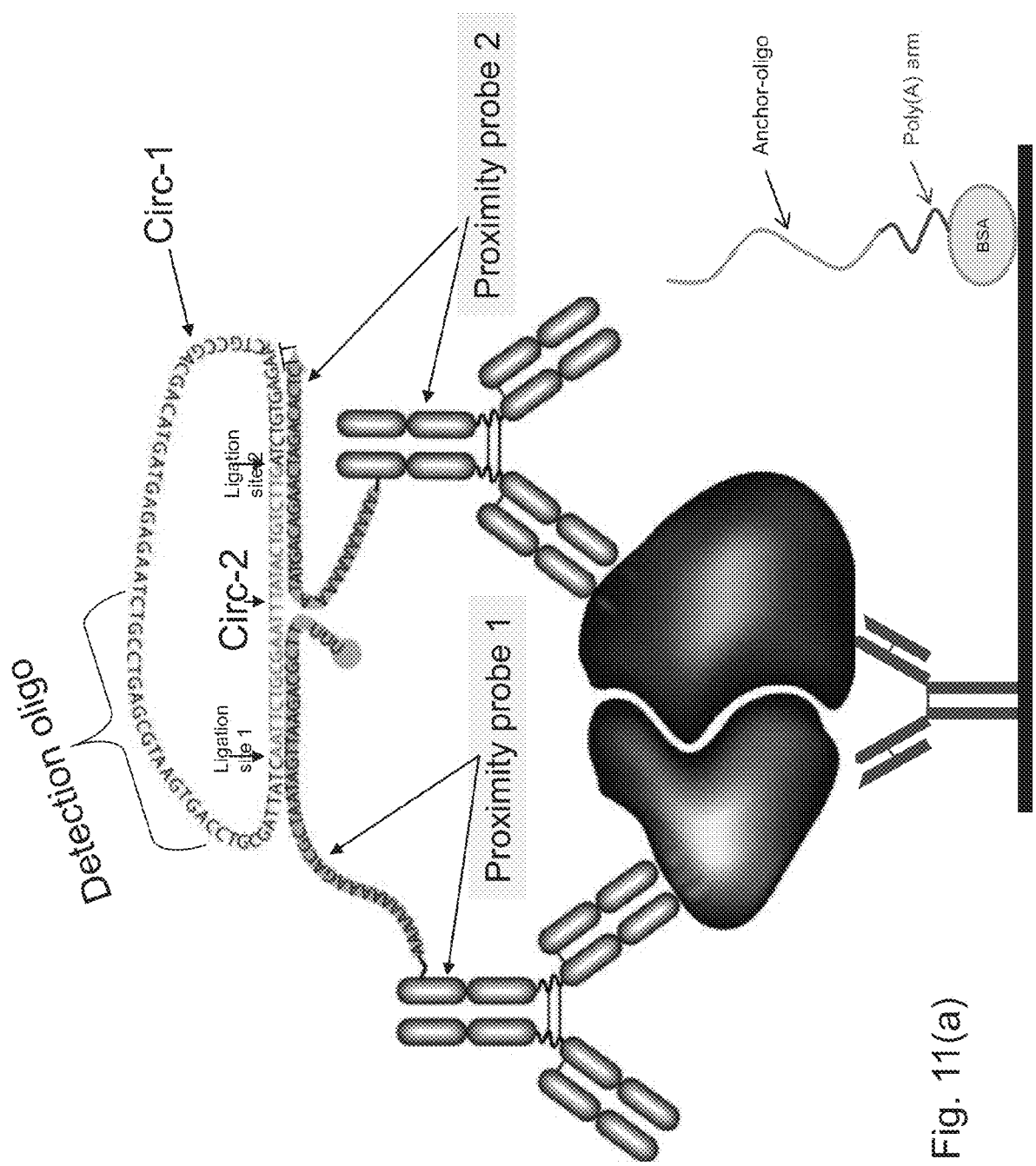
FIG. 11(a) shows the configuration of a single linear connector oligonucleotide sequence including either ligation site 1 or 2 and the use of these connectors in an assay of the invention. Circ-1, SEQ ID NO: 4; Circ-2, SEQ ID NO: 5; Proximity probe 1, SEQ ID NO: 1; Proximity probe 2, SEQ ID NO: 2.
Figure 11B:
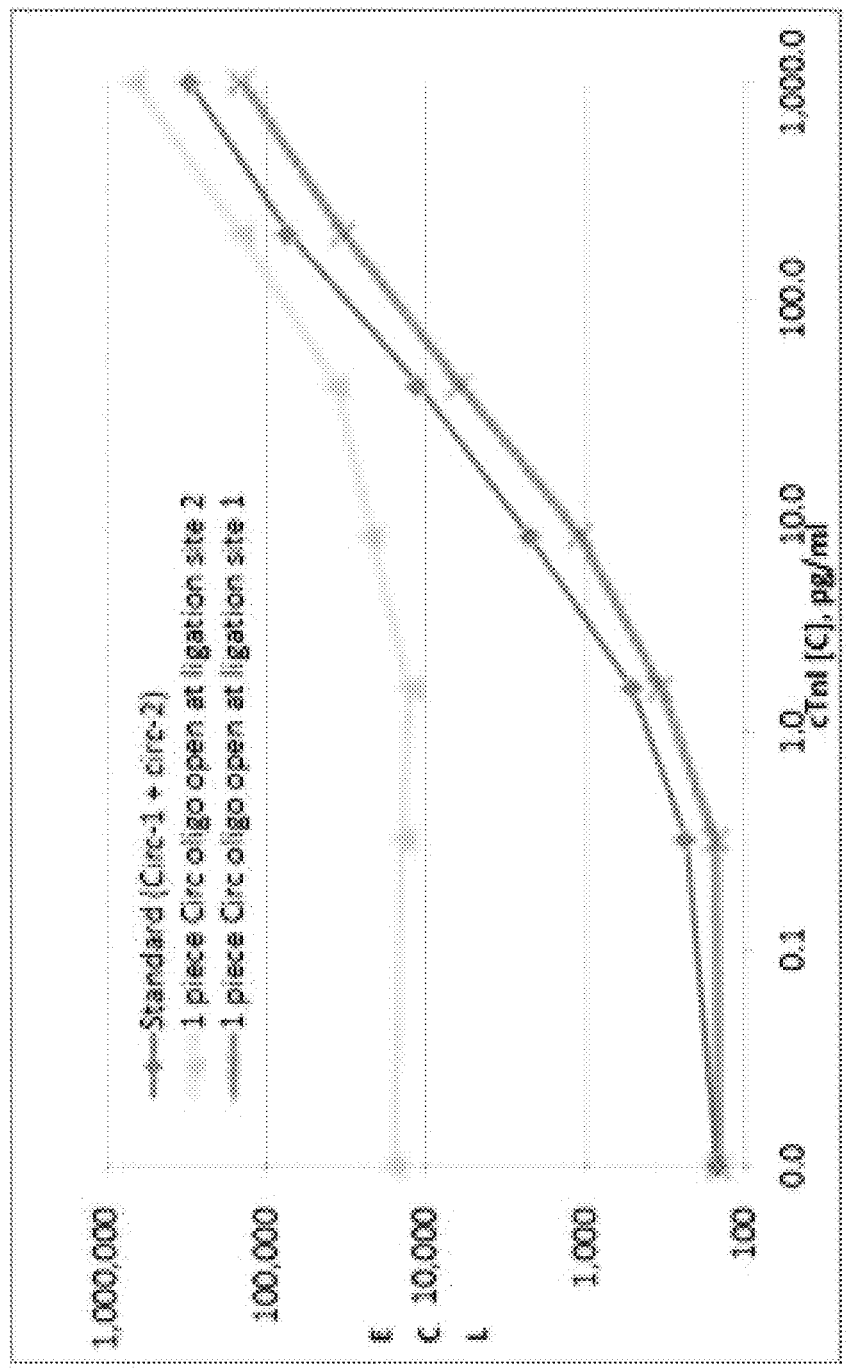
FIG. 11(b) shows comparative performance data for an assay using a combination of Circ-1 and Circ-2 vs. either a single linear connector oligonucleotide sequence including ligation site 1 or a single linear connector oligonucleotide sequence including ligation site 2.

The assay described in Example 2 was repeated using a single linear connector oligonucleotide with one ligation site to form a circular template instead of two connector oligonucleotides with two separate ligation sites. As shown in FIG. 11(a), a single linear connector oligonucleotide was prepared that was open at ligation site 1 or ligation site 2. Both single linear connector oligonucleotides were tested side by side with the combination of oligonucleotides used in Examples 1 and 2, Circ-1 and Circ-2. The protocol described in Example 2 was employed and in addition, the single linear connector oligonucleotides were tested at three concentrations: 125 nM, 62.5 nM, and 31 nM, while the standard assay using the combination of Circ-1 and Circ-2 oligonucleotides were tested at 125 nM. As shown in FIG. 11(b), the two single linear connector oligonucleotides were successfully incorporated into RCA amplification products with roughly the same efficiency as the two-part connector oligonucleotide mix (Circ-1 and Circ-2). The single linear connector oligonucleotide that was open at ligation site 1 had performance comparable to the two-part connector mix, based on signal intensity, non-specific background and overall sensitivity. As expected, the single linear connector oligonucleotide that was open at ligation site 2 had higher non-specific background and lower sensitivity. In this latter case, both ligation and priming was only dependent on the presence of proximity probe #1; therefore some of the specificity benefits of the proximity amplification approach was lost.

Example 4. Three-Antibody Assays Conducted Using Alternative Proximity Probe, Anchor Oligonucleotide, and Connector Sequences An assay was conducted using the protocol outlined in Example 1, using the following alternative sets of reagents:

TABLE 4

| Sequence Description | Sequence |
|---|---|
| Alternate Set (a) | |
| Detection oligo | 5'-/5Biosg/ACATCGGTAGTT-3' (SEQ ID NO: 7) |
| Proximity oligo 1 | /5ThioMC6-D/aaaaaaaaaaCACTAAGCTGTTAGTCCATTACCGmUmUmU (SEQ ID NO: 8) |
| Proximity oligo 2 | /5ThioMC6-D/aaaaaaaaaaGCTGGAGGTTCAGACGATTTTGCG (SEQ ID NO: 9) |
| Circ-1 | /5Phos/AACAGCTTAGTGACATCGGTAGTTAACAGATTGATCTTGACACATCGGTAGTTCGCAAAATCGTC (SEQ ID NO: 10) |
| Circ-2 | /5Phos/TGAACCTCCAGCTTTCGGTAATGGACT (SEQ ID NO: 11) |
| Anchor oligo | 5'ACAGATTGATCTTGAAAA AAA AAA AAA AAA AAA AA/3ThioMC3-D/ (SEQ ID NO: 12) |
| Alternate Set (b) | |
| Detection oligo | 5'-/5Biosg/ACATCGGTAGTT-3' (SEQ ID NO: 7) |
| Proximity oligo 1 | /5ThioMC6-D/aaaaaaaaaaAGAGTCCAGAGGCAAAGCGTGAATmUmUmU (SEQ ID NO: 13) |
| Proximity oligo 2 | /5ThioMC6-D/aaaaaaaaaaGATAAGGAAGGGGCCTTAGCGACA (SEQ ID NO: 14) |
| Circ-1 | /5Phos/CCTCTGGACTCTACATCGGTAGTTTGGAACATTTTATTCTAACATCGGTAGTTTGTCGCTAAGGC (SEQ ID NO: 15) |
| Circ-2 | /5Phos/CCCTTCCTTATCTTTATTCACGCTTTG (SEQ ID NO: 16) |
| Anchor oligo | 5'GGAACATTTTATTCTAAA AAA AAA AAA AAA AAA AA/3ThioMC3-D/ (SEQ ID NO: 17) |
| Alternate Set (c) | |
| Detection oligo | 5'-/5Biosg/ACATCGGTAGTT-3' (SEQ ID NO: 7) |
| Proximity oligo 1 | /5ThioMC6-D/aaaaaaaaaaAACAACTCCGATTGCTTGCTTCTTmUmUmU (SEQ ID NO: 18) |
| Proximity oligo 2 | /5ThioMC6-D/aaaaaaaaaaTAGCCCTACGTGCCCTGCATAGAC (SEQ ID NO: 19) |
| Circ-1 | /5Phos/ATCGGAGTTGTTACATCGGTAGTTCGCGCAGGTCGGGATTACATCGGTAGTTGTCTATGCAGGG (SEQ ID NO: 20) |
| Circ-2 | /5Phos/CACGTAGGGCTATTTAAGAAGCAAGCA (SEQ ID NO: 21) |
| Anchor oligo | 5'GCGCAGGTCGGGAATAAA AAA AAA AAA AAA AAA AA/3ThioMC3-D/ (SEQ ID NO: 22) |

The results in Table 5 below are for a troponin assay in which the concentration of troponin was 500 pg/mL and each well of a MULTI-SPOT® plate included one capture spot with anchor oligonucleotide from one of the sets listed in Table 4. The assay used one proximity probe (1) and one proximity probe (2), at the same concentrations as described in Example 1. Non-specific binding for sets (a)-(c) was higher because they had 9 times greater concentration of detection oligonucleotide-SA-STAG compared to that described in Example 1. The higher concentration of detection oligonucleotide-SA-STAG resulted from titration of the pre-bound complex together, rather than titration of SA-STAG alone, as in Example 1.

TABLE 5

| PLA Sets | (a) | (b) | (c) | Example 1 |
|---|---|---|---|---|
| Troponin | 178,560 | 138,540 | 189,166 | 273,261 |
| Zero Troponin | 412 | 314 | 545 | 88 |

Example 5. Three-Antibody Assays Conducted on Additional Immunoassay Platforms (a) Bead-Based Immunoassay Format Using Coded Particles All assay steps are performed in a 96-well filter plate. Remove liquid from the plate with a vacuum manifold (not exceeding 10 In. of Hg). Never turn the plate over. If clogging should occur, use the pointed end of a 15 ml conical tube to gently press the area under the clogged well and then use a 1 ml Pasteur pipette rubber bulb or place thumb over clogged well to dislodge clog by generating pressure. Following final aspiration step, lightly tap bottom of plate on a stack of paper towels and then dab the bottom of the filter plate with a Kimwipe to remove residual liquid/droplets.

Wash Solution Preparation: Prepare 1× Working Wash Solution by diluting the entire contents of the 20× Wash Solution bottle with 285 ml deionized water.

Assay Standard Preparation: Reconstitute the lyophilized standard in 100% Assay Diluent (serum and plasma samples) or 50% Assay Diluent/50% tissue culture media (tissue culture supernatants); Reconstitution Volumes: (i) 1 vial: 1 ml; (ii) 2 vials: 0.5 ml per vial. Rehydrate at room temperature for 8-10 minutes. Gently invert the vial(s) several times and allow the vials to sit an additional 3-5 minutes to ensure complete hydration. If more than 1 standard is used, combine equal volumes of each standard and gently mix. Perform 3-fold serial dilutions of the reconstituted standard to prepare a seven point standard curve.

Analyte Capture:

(1) Vortex (30 sec) and sonicate (30 sec) the 10× Capture Bead stock. In a foil wrapped tube, dilute the 10× Capture Bead stock (2.5 µl per well) in Working Wash Solution (25 µl per well 2,000 to 5,000 beads/assay). For higher multiplexing adjust the volume of Working Wash Solution to account for the extra volumes of 10× Capture Bead stocks retained.

(2) Pre-wet the standard and sample wells with 200 µl Working Wash Solution.

(3) Vortex (30 sec) and sonicate (30 sec) the diluted Capture Bead solution. Immediately add 25 µl to each assay well followed by 200 µL of 1× Wash Solution. Aspirate and repeat the wash with 200 µL of Working Wash Solution. Tap and dab the bottom of the filter plate as needed.

(4) Add 50 µl Incubation Buffer to all assay wells.

(5) Add 100 µl standard into designated wells. For wells designated for samples, add 50 µl Assay Diluent followed by 50 µl sample. Cover and incubate the plate for 2 hours at room temperature on an orbital plate shaker (500-600 rpm). Cover the assay plate with an opaque lid during all incubations to protect from light. The speed may need to be adjusted depending upon the radius of the orbital shaker.

Analyte Detection (6) Prepare 1× mixture of fluorescently labeled detection antibodies: Dilute the 10× detection antibody mixture (10 µl per well) in diluent (100 µl per well). The mixture includes a pair of detection antibodies specific for the analyte of interest, one labeled with Alexa Fluor 350 (blue fluorescent label) and the other labeled with Alexa Fluor 594 (red fluorescent label) (each of these fluorescent labels are available from Life Technologies, Grand Island, N.Y., www.lifetechnologies.com). For higher multiplexing, adjust the volume of diluent to account for the extra volumes of 10× antibody mixture stocks required. Aspirate and wash the assay wells twice with 200 µl Working Wash Solution. Add 100 µl diluted detection antibody mixture to each assay well. Cover and incubate the plate for 1 hour on a plate shaker (500-600 rpm).

Assay Reading (8) Aspirate and wash the assay wells 3 times with 200 µl Working Wash Solution. Dry the bottom of the filter plate with clean paper towels to completely remove all residual droplets. Add 100 µl Working Wash Solution to each assay well and place the plate on the plate shaker (500-600 rpm) for 2-3 minutes.

(9) Analyze the bead suspension in a multi-color fluorescence particle analyzer (such as a FACS system or modified xMAP instrument) that includes color channels for each fluorescent label. For maximal sensitivity, the assay is run under conditions where any particle is likely to have only zero or one bound analyte and the amount of analyte is quantitated by counting the number of particles specific for a given analyte (based on particle coding) that comprise both fluorescent labels. Optionally, the assay can be run in a multiplex format using coded beads where the code indicates the analyte specificity of the capture antibody on a bead, and additional pairs of detection antibodies for each analyte. Where coding is determined, as in xMAP using additional fluorescence colors incorporated in the beads, the analyzer should have additional detection channels for measuring the additional colors and identifying the bead code.

(b) Bead-Based Immunoassay Format Using Coded Particles Including an Anchoring Moiety, Using Two Detection Reagents Modified with Nucleic Acid Probes As outlined in Example 5(a), all assay steps are performed in a 96-well filter plate. Wash solution and assay standard is prepared as described in Example 5(a) and a pair of detection antibodies to a target analyte are modified by the addition of proximity probes 1 and 2 as described in Example 1. Analyte is captured on capture beads as described in Example 5(a). Capture beads include an anchoring moiety, immobilized to the bead surface as a BSA-oligonucleotide conjugate, with the oligonucleotide selected to be specific for a rolling circle amplicon. The sequence of the anchoring oligonucleotide used is SEQ ID NO: 3.

Twenty-five (25) µl assay diluent, calibrator, or sample (diluted as appropriate) is mixed with a mixture of capture beads. The mixture is incubated with shaking for 1-3 hours and washed. A solution of detection antibodies labeled with proximity probes 1 and 2, prepared as described above, is added to the mixture, and incubated with shaking for 1-2 hours (alternatively, each individual detection antibody can be sequentially added, with each addition followed by a 1 hour incubation). The ligation mix described in Example 1 is added. The mixture is incubated with the ligation mix for 30 minutes at 37 C, washed to remove excess circularization oligonucleotides, and incubated with RCA mixture for 1.5 hour at 37 C, wherein the RCA mixture is described above in Example 1. The mixture is washed and a mixture of fluorescein-labeled detection probes is added and incubated for 30 minutes at 37 C, wherein the detection probe mixture is described above. The mixture is washed and the particles are aspirated into a multi-channel fluorescence particle analyzer.

(c) Bead-Based Format and Separation of Capture Analyte Molecules into Individual Nanowells Sample is prepared in 100 ul of 25% bovine serum (2-4 fold dilution) and 500K beads (paramagnetic 2.7 um, optionally fluorescently coded) coated with capture antibody are added to the sample. The sample is incubated for about 2 hrs at 23° C. The sample is washed three times with PBS (5×, 0.1% Tween-20), and a mixture of labeled detection antibodies is added (a mixture including a first biotinylated detection antibody and a hapten-conjugated antibody). The mixture is incubated for about 1 hr at 23° C. The mixture is washed three times with PBS (5×, 0.1% Tween-20), enzyme label is added, streptavidin-beta-galactosidase (40 pM), anti-hapten conjugated enzyme is also added, and the mixture is incubated for about 30 min at 23° C. (or 3 min in a Simoa analyzer). The mixture is washed seven times with PBS (5×, 0.1% Tween-20) and enzyme substrate is added, 15 ul of resorufin-beta-d-galactopyranoside (100 uM, in loading buffer).

The mixture is drawn over an array of nanowells (provided by Quanterix in a DVD format, made from a cyclic olefin polymer, with 24-samples per disc) and allowed to settle for about 2 minutes. The array is flushed with buffer, the array is sealed with fluorocarbon oil, incubated for 2-5 min at 23° C., and the results are read on a multicolor fluorescence imager. Image analysis is used to count the number of nanowells that contain both fluorescent enzyme products and thereby provide a value that correlates with the concentration of analyte in the sample.

(d) Flow Cell Analyzed, Bead Based Immunoassay Format

First incubation: 10 ul of sample, a biotinylated monoclonal analyte-specific capture antibody (working solution at 2.6 mg/1), and a mixture of monoclonal analyte-specific antibodies, each conjugated to oligonucleotides (working solution at 0.3 mg/1) react to form a sandwich complex. The mixture of monoclonal analyte-specific antibodies are prepared as in Example 1 and the mixture includes a pair of antibodies conjugated to proximity probes 1 and 2 as described above in Example 1.

Second incubation: after the addition of streptavidin-coated microparticles (Dynal M280, 2.8 um, 0.72 mg/ml, binding capacity for biotin 470 ng/mg), the complex becomes bound to the solid phase via interactions between biotin and streptavidin. A ligation mix is added to the mixture, wherein the ligation mix is prepared according to the protocol described in Example 1. The mixture is incubated with the ligation mix for 30 minutes at 37 C, washed to remove excess circularization oligonucleotides, and incubated with RCA mixture as described in Example 1. The mixture is washed and a mixture of biotin-labeled detection probes are added and incubated for 30 minutes at 37 C, wherein the detection probe mixture is prepared as described in Example 1. To incorporate the electrochemiluminescence label SULFO-TAG™ (Meso Scale Diagnostics), the detection probe is synthesized with a terminal biotin label and pre-bound to SULFO-TAG™ labeled streptavidin.

The reaction mixture is aspirated into the measuring cell where the microparticles are magnetically captured onto the surface of the electrode. Unbound substances are then removed with ProCell (TPA containing buffer). Application of a voltage to the electrode then induces chemiluminescent emission which is measured by a photomultiplier. Results are determined via a calibration curve which is instrument specifically generated by 2-point calibration and a master curve provided via the reagent bar code.

Example 6. Detection of HIV-1 P24

Figure 12:
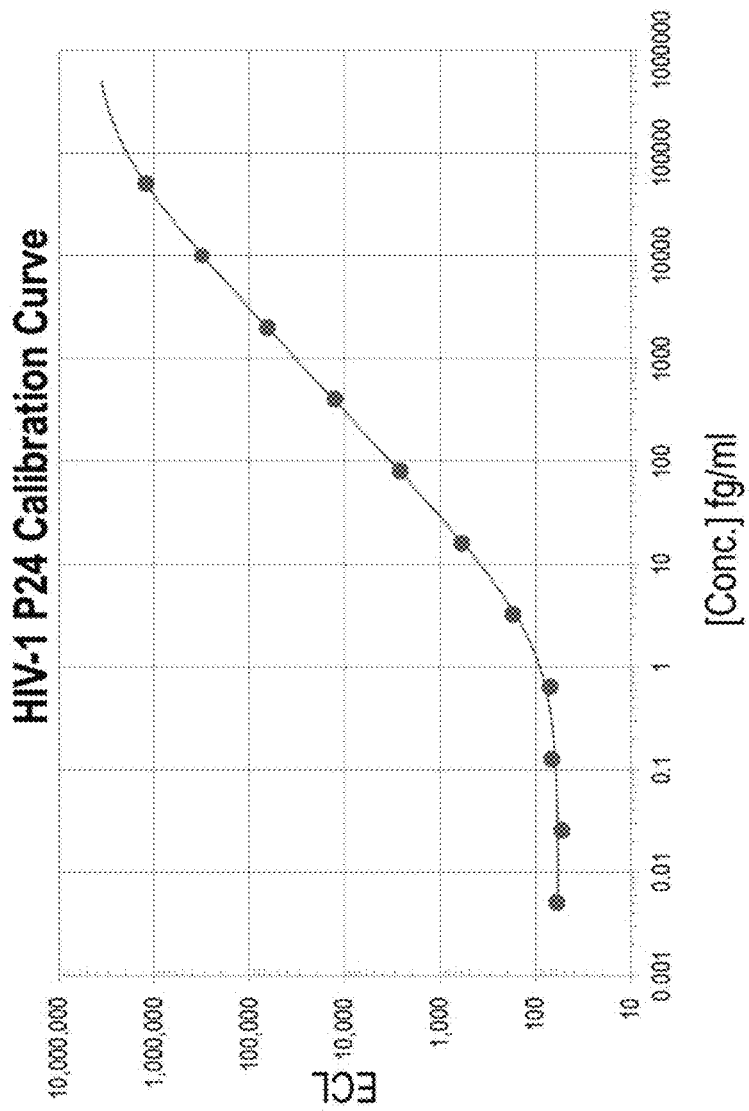
FIG. 12 shows a calibration curve for an HIV p24 assay conducted using the method described in Examples 1 and 6.

Materials, Methods, and Results:

The procedure described in Example 1 was used to detect HIV-1 p24. Approximately 64 serum or plasma samples were tested from an HIV-1 mixed titer performance panel (available from Seracare Life Sciences, www.seracarecatalog.com), HIV-1 seroconversion panel (also available from Seracare Life Sciences), HIV antibody positive samples (available from ProMedDx, LLC, www.promeddx.com), and normal matched samples (available from Bioreclamation, www.bioreclamation.com). A calibration curve for an HIV-1 p24 assay conducted according to the procedure described above is shown in FIG. 12. The LOD for the assay was found to be 1.3 fg/mL, LLOQ was 3.0 fg/mL, and ULOQ was 37,500 fg/mL. A detection limit of 1.3 fg/mL for a 25 uL sample corresponds to approximately 650 p24 molecules and each virus particle (molecule) produces approximately 2000 copies of p24 protein.

The mixed titer performance panel, PRA204(B), consisted of a set of ten specimens with reactivity ranging from weakly to strongly positive for HIV p24 antigen by commercially available assays (bioMerieux, Perkin Elmer, and Zeptometrix). Two negative specimens were included in the panel. The results of the assays are shown in Table 6 below:

TABLE 6

| Panel member | bioMerieux HIV Ag VIDAS p24 (pg/mL) | Perkin Elmer HIV Ag p24 (s/co) | Zeptometrix HIV Ag p24 (s/co) | MSD 3AB format (pg/mL) | MSD 3AB format (ECL) |
|---|---|---|---|---|---|
| PRA204(B)-09 | >400 | >42 | 75 | >38 | 1915873 |
| PRA204(B)-10 | <3 | 1 | 0 | 0.0 | 174 |
| PRA204(B)-11 | 85 | 18 | 16 | >38 | 1674519 |
| PRA204(B)-12 | 60 | 11 | 14 | >38 | 1601078 |
| PRA204(B)-13 | 170 | 47 | 41 | >38 | 1902237 |
| PRA204(B)-15 | 192 | 45 | 36 | >38 | 1884816 |
| PRA204(B)-17 | >400 | 42 | 61 | >38 | 1897359 |
| PRA204(B)-20 | <3 | 1 | 0 | 0.0 | 150 |
| PRA204(B)-21 | 68 | 14 | 18 | >38 | 1422070 |
| PRA204(B)-22 | 17 | 3 | 1 | 10 | 347517 |
| PRA204(B)-23 | 14 | 2 | 2 | 7 | 237726 |
| PRA204(B)-24 | 15 | 3 | 3 | 9 | 306728 |

HIV p24 levels were high and above the ULOQ for most of the samples. All ten positive samples were detectable and comparable to commercially available p24 kits, while negative samples (based on commercial assays, PRA204(B)-10 and -20, respectively) were quite low at approximately 3 and 2 fg/mL, respectively.

Figure 13:
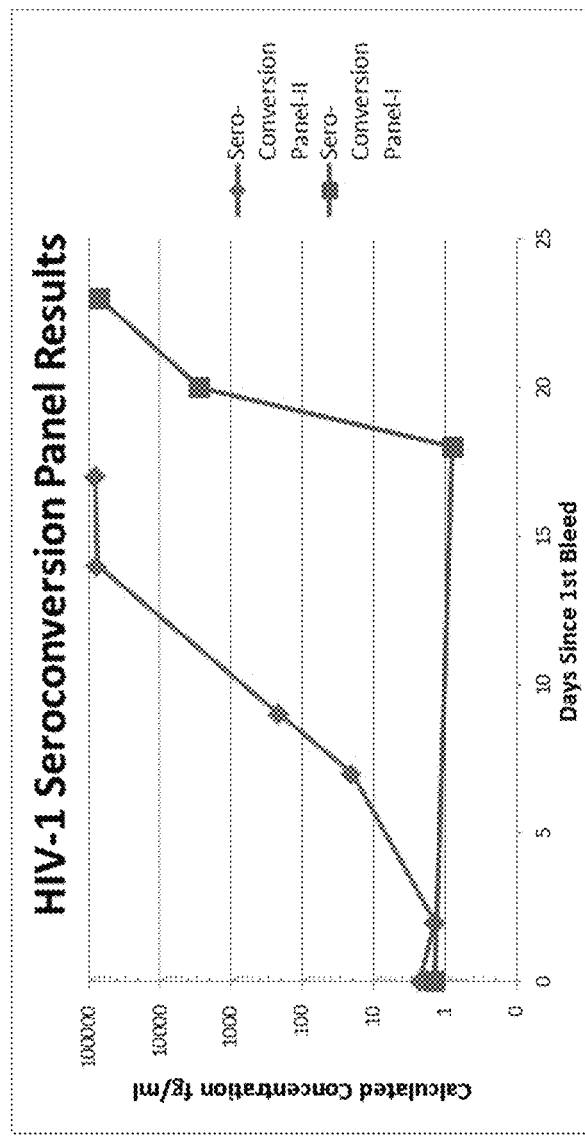
FIG. 13 shows the results of an analysis of a seroconversion panel using the method described in Examples 1 and 6.

The results for the analysis of the seroconversion panel are shown in FIG. 13. The 3-antibody assay format was found to be as sensitive as PCR and the estimated delay in the time to detect the first positive sample and the p24 levels in both samples from PRB948 and PRB962 panels compares with the PCR kit and performs better than other commercial p24 assays. The data are shown in Table 7.

TABLE 7

| Panel & member | Days since 1st bleed | Abbott BBI (s/co) | Coulter BBI (s/co) | DuPont BBI (s/co) | Inno. (s/co) | MSD 3AB (pg/mL) | MSD 3AB (ECL) | Roche PCR (co/mL) |
|---|---|---|---|---|---|---|---|---|
| Panel I-I, | 0 | 0.4 | 0 | 0.1 | 0.4 | 0.001 | 121 | BLD |

TABLE 7-continued

| | | | | | | | | |
|---|---|---|---|---|---|---|---|---|
| Panel I-I, PRB948-01 | 18 | 0.4 | 0 | 0.1 | 0.4 | 0.001 | 100 | BLD |
| Panel I-I, PRB948-01 | 20 | 0.5 | 0.2 | 0.5 | 1 | 3 | 97688 | $3 \times 10^4$ |
| Panel I-I, PRB948-01 | 23 | 5 | 23 | 15 | 31 | >38 | 1736809 | $6 \times 10^5$ |

| | Days since 1st bleed | Coulter (s/co)2 | PE (s/co)2 | Roche Elecsys (s/co)2 | Zepto (s/co)2 | MSD 3AB (pg/mL) | MSD 3AB (ECL) | Roche Ultra (co/mL) | Roche standard |
|---|---|---|---|---|---|---|---|---|---|
| Panel I-II, PRB962-01 | 0 | 0.3 | 0.3 | 0.1 | 0.1 | 0.002 | 149 | <50 | NT |
| Panel I-II, PRB962-02 | 2 | 0.2 | 0.2 | 0.2 | 0.2 | 0.001 | 120 | <50 | NT |
| Panel I-II, PRB962-03 | 7 | 0.2 | 0.2 | 0.2 | 0.2 | 0.021 | 778 | NT | $7.6 \times 10^2$ |
| Panel I-II, PRB962-04 | 9 | 0.6 | 0.3 | 0.3 | 0.3 | 0.2 | 7603 | NT | $7.7 \times 10^2$ |
| Panel I-II, PRB962-05 | 14 | >40 | 30 | 23 | 10 | >38 | 1808344 | NT | $7.0 \times 10^3$ |
| Panel I-II, PRB962-06 | 17 | >40 | >49 | 155 | 24 | >38 | 1863699 | NT | $1.2 \times 10^7$ |

Abbott BBI refers to Abbott BBI HIV-1 Antigen test.
Coulter BBI refers to Coulter BBI HIV-1 Antigen test.
DuPont BBI refers to DuPont BBI HIV-1 Antigen test.
Inno. refers to Innogenetics R129 HIV-1 Antigen test.
Roche PCR refers to Roche PCR HIV RNA BBI test.
Coulter refers to Coulter ELISA HIV-1 Antigen test.
PE refers to Perkin Elmer ELISA HIV-1 Antigen test.
Zepto. refers to Zeptometrix ELISA HIV-1 Antigen test.
Roche Ultra refers to Roche Ultrasensitive HIV-1 RNA test.
Roche standard refers to the Roche standard HIV-1 RNA test.
BLD = below detection limit and
NT = not tested.

CONCLUSIONS

Patients who have recently been infected with HIV contribute disproportionately to the spread of the disease. Viral loads are high in the first few weeks after infection, and newly infected patients are unlikely to be aware that they are infected and can spread the disease to others. Therefore, early detection of acute HIV infection is of great importance for public health. PCR methods are the gold standard with respect to sensitivity; they can detect as few as 60 HIV RNA copies per mL of serum or plasma (30 virus particles per mL). However, PCR technology is complex and expensive, and therefore not suitable for all settings. Immunoassays are simpler and cheaper, but the detection limit of current, $4^{th}$ generation p24 immunoassays is only about 10 pg/mL, or approximately 250 million capsid proteins per mL. On a per virus basis, these immunoassays are several thousand times less sensitive than PCR testing, despite the fact that there are about 2,000 p24 capsid proteins per virus.

As described herein, a next-generation electrochemiluminescence assay format based on MSD's MULTI-ARRAY® technology was developed and its performance characterized. The detection limit for this novel p24 immunoassay was approximately 1 fg/mL, 10,000 fold more sensitive than current p24 immunoassays. A sensitivity of 1 fg/mL corresponds to less than 1 virus particle in our sample volume of 25 uL. The lower and upper limits of quantitation were 3 fg/mL and 38,000 fg/mL, respectively. Within-plate CV was 7%, and total CV 15%. Spike recovery and dilution linearity were between 80% and 120%. p24 was undetectable in the serum or plasma of 32 apparently healthy donors. The p24 mixed titer panel showed good correlation between 3-AB HIVp24 assays and commercial p24 immunoassays. Two seroconversion panels were tested: SeraCare PRB948 (days 0 and 18, PCR negative; days 22 and 23, PCR positive) and PRB962 (days 0 and 2, PCR negative; days 7, 9, 14, and 17, PCR positive). In both cases, the 3AB HIVp24 assay result was negative for all PCR-negative samples and positive for all PCR-positive samples, and infection was detected well before conventional p24 immunoassays.

In conclusion, the 3-AB HIVp24 immunoassay described herein is 10,000 times more sensitive than the current limits of p24 ELISAs and comparable in sensitivity to PCR assays. The assay does not require specialized equipment and can be run on the MESO™ QuickPlex SQ 120, and SECTOR® Imagers.

Example 7. Concentration of Analyte, Followed by 3-AB RCA/PLA Assay (a) The conditions of the experiment are shown in Table 8(a), below:

TABLE 8(a)

| Reagent | Type | Amount | Binding Conditions |
|---|---|---|---|
| Reagents | | | |
| Magnetic beads | Dynabeads ® MyOne ™ Streptavidin T1 | 0.25 mg | NA |
| Capture oligonucleotide | PP1 complement | 100 pmol | Diluent 100 (1 hr) |
| Proximity Probe (PP)-analyte detection antibody | PP1-detection antibody specific for HIVp24 | 6.7 pmol | (1) 1M NaCl (40 min.) (2) 0.5M NaCl (40 min.) |
| Antigen | HIVp24 | 7 pg/ml | (1) 1M NaCl (overnight) (2) 0.5M NaCl (overnight) |
| Control | Beads w/o capture, including PP1 and antigen | .25 mg | Same binding conditions as testing samples, without release step |
| Release Conditions | | | |
| PP/Antigen complex | PP1/HIVp24 | 0 salt | 25 C. 30 C. 37 C. |
| | | 10 mM salt | 25 C. 30 C. 37 C. |

For the capture of relatively short oligonucleotide proximity probe sequences (e.g., from 9-13 nucleotides long), capture oligonucleotides complementary to a portion of proximity probe sequences were prepared and biotinylated at the 3' end. Table 8(b) shows the details of the proximity probe and capture oligonucleotide sequences:

TABLE 8(b)

| PP1 sequence | /5ThioMC6-D/AAAAAAAAAAGACGCTAATAGTTAAGACGCTTTmUmUmU (SEQ ID NO.: 23) | | |
|---|---|---|---|
| Capture oligo | Sequence Name | Sequence Length | Sequence (5'-3') 5'/Poly A (20 spacer Biotin/ |
| Capture oligo 1 | Cap-1: 16 | 16 | Aagcgtcttaactatt (SEQ ID NO.: 24) |
| Capture oligo 2 | Cap-1: 13 | 13 | Aagcgtcttaact (SEQ ID NO.: 25) |
| Capture oligo 3 | Cap-1: 12 | 12 | Aagcgtcttaac (SEQ ID NO.: 26) |
| Capture oligo 4 | Cap-1: 11 | 11 | Aagcgtcttaa (SEQ ID NO.: 27) |
| Capture oligo 5 | Cap-1: 10 | 10 | Aagcgtctta (SEQ ID NO.: 28) |
| Capture oligo 6 | Cap-1: 9 | 9 | Aagcgtctt (SEQ ID NO.: 29) |
| Capture oligo 7 | Cap-1: 8 | 8 | Aagcgtct (SEQ ID NO.: 30) |

The calculated melting temperatures are shown in Table 8(c):

| | Tm | | | |
|---|---|---|---|---|
| PP1 [C], nM | 10 | 10 | 10 | 10 |
| Cap [C], nM | 10 | 10 | 10 | 100 |
| Salt, mM | 1200 | 500 | 40 | 40 |
| Cap1-16 | 57 | 51 | 37 | 43 |
| Cap1-13 | 51 | 46 | 33 | 39 |

-continued

| | Tm | | | |
|---|---|---|---|---|
| Cap1-12 | 46 | 42 | 28 | 35 |
| Cap1-11 | 36 | 32 | 19 | 26 |
| Cap1-10 | 34 | 29 | 16 | 24 |
| Cap1-9 | 34 | 30 | 18 | 26 |
| Cap1-8 | 26 | 22 | 9 | 19 |

Beads modified with capture oligonucleotides were prepared as follows: fifty (50) ul of Dynal MyOne Streptavidin T1 bead slurry were added after vortexing to five 1.5 mL Eppendorf tubes, each having twice the amount required for division across two binding condition experiments. The beads were washed three times with 1 ml Diluent 100 (available from Meso Scale Discovery, Rockville, Md.) and 1.2 mL of each capture oligonucleotide was added to each vial at 200 pmol/ml of each capture oligonucleotide in Diluent 100 including EDTA. The solutions were incubated by rotating for 1 hour at room temperature and the solution in each tube was spiked with free biotin to 5 nmol/mL in Diluent 100 including EDTA. The solutions were incubated by rotating for 15 minutes at room temperature and the beads were washed three times with 1 mL of 0.5M NaCl/BSA solution. The tubes were filled with 1 mL 0.5 M NaCl/BSA, mixed, and each capture oligonucleotide-bead mixture was aliquoted into 2 vials, for a total of 10 vials.

Solution was aspirated from all vials and 1 mL PP1 (PP1 sequence bound to a detection antibody specific for HIVp24) at 1 ug/mL (6.7 pmol/mL) in 0.5 M and 1 M NaCl/BSA was added to each capture tube. The solutions were incubated for 40 minutes with rotation at room temperature. Each tube was washed three times with a salt solution (controls that do not include capture oligonucleotides were not washed). To four tubes, 1 mL HIVp24 was added at 7 pg/mL, while antigen was spiked from a stock solution into the no capture control tube. The solutions were incubated with rotation at 4 C overnight and each tube with capture oligonucleotide was washed three times with salt solution (1 mL each). Each tube was filled 1/3 with wash buffer (0.1× PBS, 500 mM NaCl, 1 mM EDTA, 0.1% Triton X-100, 2 mg/mL BSA), mixed, and an aliquot of 400 uL of beads was added into two vials for 2 release salt conditions for a total of 18 tubes. The wash buffer was removed from all vials except the no capture control tubes, and 400 uL 0.0M and 10 mM salt buffer was added to the tubes. The contents of the tubes were mixed and an aliquot of 100 uL from each tube (including control beans without capture) was added to three matrix plates for analysis of three temperature release conditions. The plates were incubated at 25 C, 30 C, and 37 C, respectively, in a thermoshaker with mixing for 5 minutes. The beads were magnetically separated and 25 uL of supernatant was added to a well of an assay plate spiked with 5 uL 6×PBS, including mIgG (three replicates per condition). The plate was incubated 1 hour at room temperature with shaking and washed three times in PBS buffer. As described in Example 1, each binding domain on the plate included a capture antibody and an anchoring moiety, and following the incubation step, a complex is formed at each binding domain that included a capture antibody bound to the antigen, which is bound to a detection antibody having a PP1sequence (except for control binding domains).

A solution of detection antibodies labeled with PP2 (or PP1+PP2 for controls) was added to each well (25 uL per well), and incubated with shaking for 1 hour, followed by a wash. As described in Example 1, ligation mix was added to each well and the plate was incubated with the ligation mix for 30 minutes at room temperature, washed to remove excess circularization oligonucleotides, and incubated with RCA mixture for 1.5 hour at 37 C. The plate was washed and a mixture of detection probes were added and incubated for 30 minutes at 37 C. The plate was washed and filled with 150 µl MSD read buffer and read immediately on a MSD SECTOR® Plate Reader.

The results of this experiment are shown in FIG. 14.

(b) An additional experiment was conducted to further evaluate analyte concentration conditions. The general experimental conditions are described in Table 9(a):

| Capture-Release with PP1 beads | | | |
|---|---|---|---|
| Buffer | Volume | Time, temperature | Concentration factor |
| Liquid Phase Binding | | | |
| Diluent 2 (available from Meso Scale Discovery, Rockville, MD) | 5 mL | Overnight, 4 C. | NA |
| Release | | | |
| 0 salt solution (1 mM EDTA, 2 mg/mL BSA) | 100 uL | 6 minute, 25 C. | 50X |
| Control conditions | | | |
| No beads, no capture-release, antigen + PP1 | | | |
| Capture-release with beads, no concentration step | | | |
| Assay plate binding (solid phase conditions) | | | |
| 1X PBS | 3 uL 10X PBS/mIgG + 30 uL sample | 1.5 h, room temperature | NA |

Fifty (50) ul of Dynal MyOne Streptavidin T1 bead slurry were added after vortexing to a microcentrifuge tube. The beads were washed three times with 1 ml Diluent 100 and 1 mL of capture oligonucleotide Cap 1:9 was added Diluent 100 including EDTA. The solution was incubated by rotating for 1 hour at room temperature and the solution was spiked with free biotin to 10× excess in Diluent 100 including EDTA. The solution was incubated by rotating for 30 minutes at room temperature and the beads were washed three times with 1 mL of wash buffer. One (1.0) mL PP1 in binding buffer was added and the solution was incubated for 40 minutes with rotation at room temperature. The tube was washed three times with a wash buffer and 1 mL Diluent 2 was added to the beads, mixed, and the bead solution was divided across 12 tubes for 1×, 0.5×, 0.25×, and 0.125× bead-PP1 concentration at antigen levels 2-4. The required volume of bead-PP was transferred to a control tube. HIVp24 and Diluent 2 were added to bead solutions for required final concentrations of antigen and bead-PP at a total volume of 5 mL. No bead control tubes were spiked to include free PP1 at 1× concentration only and all 4 levels of antigen. The tubes were incubated with rotating at 4 C overnight, and 5 mL bead solutions were transferred to 1.5 mL Eppendorf tubes by transferring 1 mL at a time. Each tube was washed with wash buffer (three times). Control tubes without beads were not washed. After the third wash, 100 uL of 0 salt solution was added to test tubes, and 500 uL of 0 salt solution to control tubes, and the tubes were incubated at 25 C for 6 minutes. Supernatant was transferred to an assay plate and analyzed as in Example 7(a). The results are shown in Table 9(b)-(c):

TABLE 9(b)

| Sample # | [C], fg/ml | Cap-Release on beads Non-[C]ed | Cap-Release on beads 50X [C]-ed | No beads Cntrl | Signal increase, X |
|---|---|---|---|---|---|
| 1 | 120 | 3,764 | | 3,687 | |
| 2 | 12 | | 15,314 | 369 | 41.5 |
| 3 | 1.2 | | 1,941 | 71 | NA |
| 4 | 0.12 | | 280 | 32 | NA |
| Zero | | | | 32 | |

TABLE 9(c)

| Ag [C], fg/ml | ~virion number/ml | ~p24 #/ml | ~p24 # in 30 µl |
|---|---|---|---|
| 120 | 1000 | 3,000,000 | 90,000 |
| 12 | 100 | 300,000 | 9,000 |
| 1.2 | 10 | 30,000 | 900 |
| 0.12 | 1 | 3000 | 90 |

Figure 15:
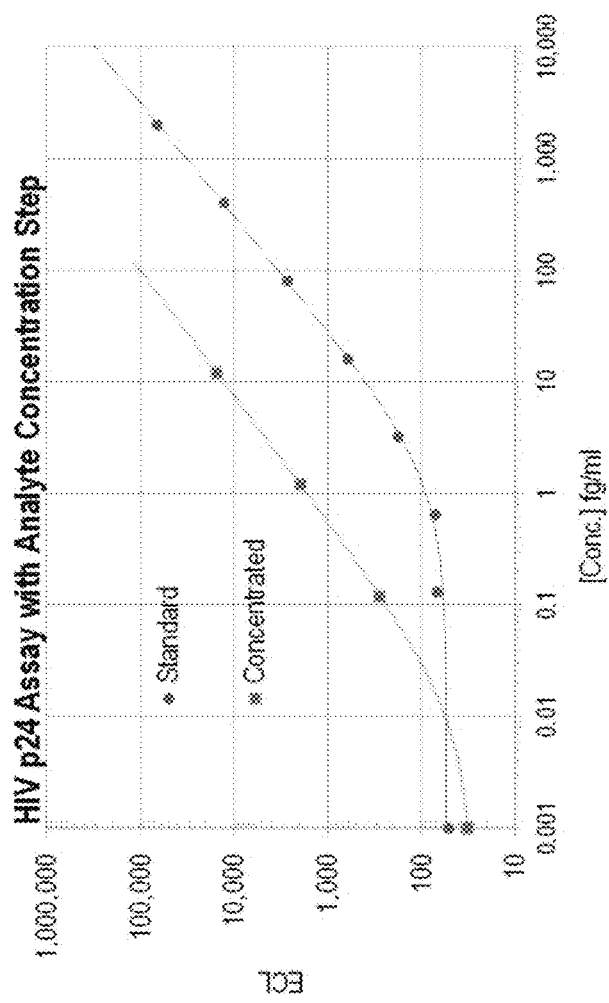
FIG. 15 shows a calibration curve for an HIVp24 assay including an analyte concentration step.

An increase in signal of approximately fifty fold was observed after analyte concentration with magnetic beads. Non-concentrated sample #1 showed results similar to Control #1 signals, which indicated release of PP-Antigen complex with the highest efficiency. Using analyte preconcentration, detection of less than 0.1 fg/mL was achieved, which is comparable to 1 virion/mL viral load. In contrast, commercial viral assays can reasonably detect approximately 50 copies/mL, which is equivalent to 25 virion/mL. A calibration curve with and without preconcentration for this experiment is shown in FIG. 15.

Example 8. 3-AB RCA/PLA Bead-Based Assay Using Bead Settling Protocol

A 3-AB RCA/PLA assay for IL-4 was conducted as described in Example 7, except that silica beads (available from _) were used instead of Dynabeads. RCA and detection incubations were performed in MSD large spot multi-well assay plates (available from Meso Scale Discovery, Rockville, Md.), stationary at 37° C. The beads did not include an anchoring reagent. Beads were allowed to settle slowly during the RCA incubation step by gravity onto the surface of a well, with an approximate settling time of 5-8 minutes, depending on the solution volume. The plates were washed by spinning the plates in a swinging bucket centrifuge. Preliminary testing indicated that the beads were uniformly dispersed after spinning with only a slight gradient across the well surface.

The protocol was tested with 15 vs. 90 minute RCA incubations. It was found that the sensitivity and dynamic range of the assay were improved approximately 10-fold with a 15 minute RCA incubation using the bead settling protocol compared to magnetic capture. Sensitivity was further improved with a 90 minute RCA incubation step (up to approximately 50-100 fold).

Alternatively, a 3-AB RCA/PLA assay is performed as described herein, in which the bead includes anchoring reagent and a blocking agent (approximately 2.5 mg/ml) is added during the ligation step to decrease non-specific binding. A variety of blocking agents can be used, including but not limited to, mBSA, sheared poly(A), polyBSA-I, mIgG, Tween, polyBSA-II, yeast RNA, mBSA+poly(a), and/or polyBSA+poly(A).

Example 9. Modified Bridging Immunoassay Format

Figure 19:
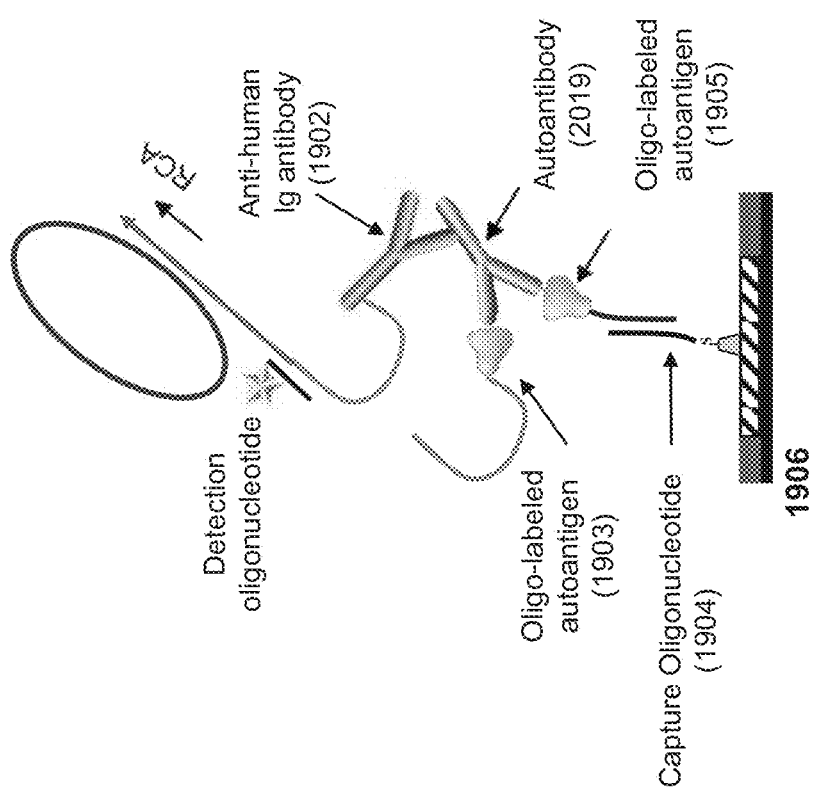
FIG. 19 is a schematic representation of a bridging immunoassay format incorporating 3AB PLA-RCA technique and the use of a targeting moiety and its complement to bind the capture reagent to the surface.

As stated above, the procedure described in Example 1 was used in bridging and isotyping Ig assays using TNFalpha model system, bridging and isotyping Ig assays using Hep B surface antigen, and bridging and isotyping Ig assays using Lyme C6. A modification to this procedure is shown in FIG. 19 in which an autoantibody (1901) was detected using (i) a PP2-modified anti-human Ig antibody (1902), and (ii) a PP1-labeled autoantigen (1903), followed by PLA-RCA as described in Example 1. The format shown in FIG. 19 also shows the use of a targeting moiety (1904) and its complement bound to autoantigen (1905) as a means of adhering a capture moiety, in this case, autoantigen, to the surface (1906).

Likewise, an immunoassay for an antibody, e.g., an autoantibody, can be conducted as described in Example 1 wherein antigen for that antibody is used as the capture moiety (directly attached to the surface or via a targeting moiety and its complement), and the two detection species are an isotype antibody attached to PP1, and antigen attached to PP2 (or vice versa). The sandwich complex is formed, followed by PLA-RCA as described in Example 1. These modified assay formats can also include an anchor moiety to adhere the amplicon to the surface.

Example 10. Biosynthetic Method for the Generation of Proximity Ligation Rolling Circle Templates Proximity ligation rolling circle templates can be generated biosynthetically. This method makes use of an initially highly purified and well-characterized template to generate an RCA product in an efficient solution-based ligation and RCA reaction series. This process can also be done on beads to enhance the selectivity of the reactions.

Figure 20A:
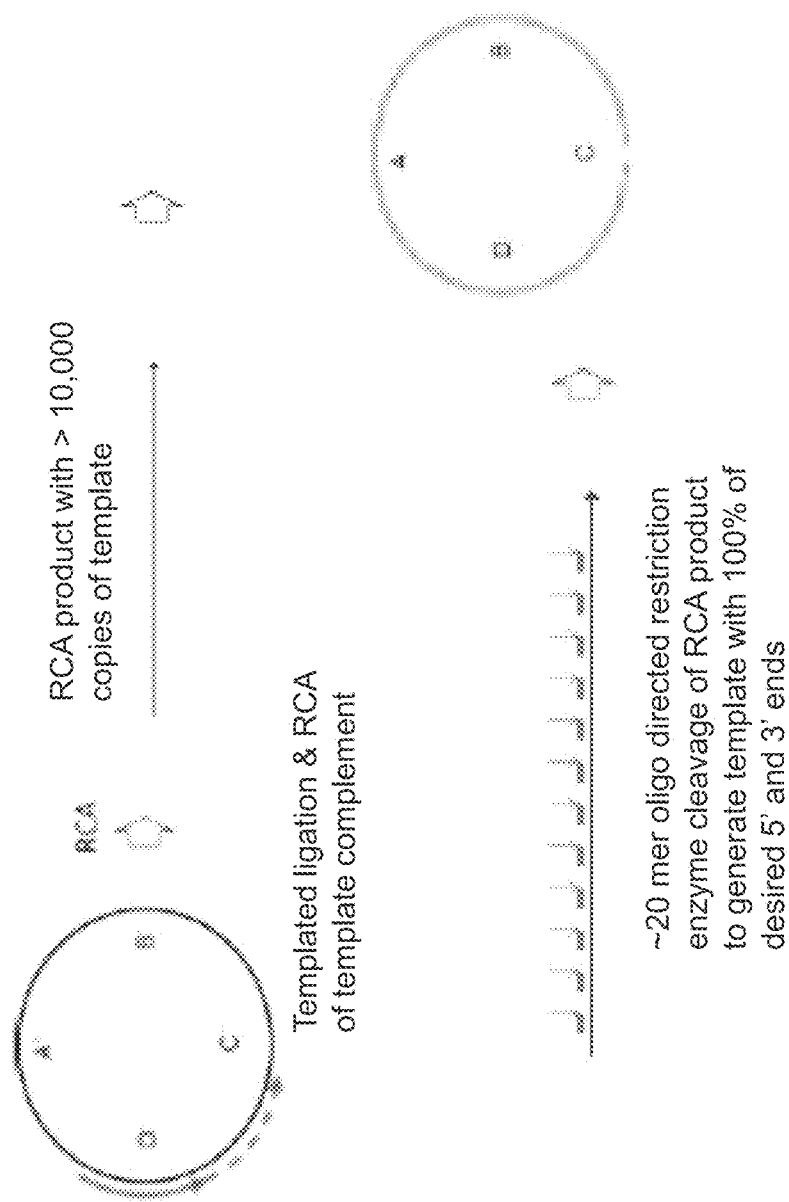
FIGS. 20(a)-(b) are schematic representations of biosynthetic methods for template formation.
Figure 20B:
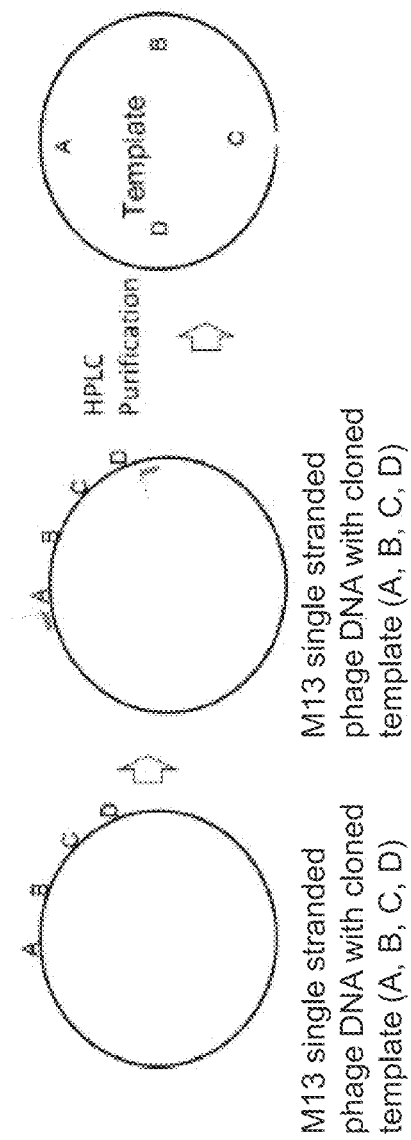

Following the amplification of the seed RCA template, the single stranded product is subjected to site specific cleavage using a unique restriction enzyme in combination with a short synthetic sequence. Therefore, the RCA template is generated from its own product. The biosynthetically generated RCA template is subjected to HPLC or gel purification to generate a product that contains 100% of the correct 5' and 3' termini. This method is illustrated in FIG. 20(a). This approach requires the addition of a restriction site into the RCA template to direct cleavage at the desired ligation site. Restriction enzymes such as those cutting approximately 14-20 bases away from the restriction site, are preferable. Alternatively the single stranded template can also be generated in milligram amounts using this approach in combination with single stranded DNA from M13 phage, or similar. This approach can obviate the need to carry out an RCA-based amplification of the RCA template, only requiring the cloning of the template into an M13 vector for DNA production. This is illustrated in FIG. 20(b).

Example 11. Sample Multiplexing

The methods described herein are used to multiplex samples based on the use of spectral signatures. Multiplexing samples offers the user the ability to do internal calibration and control, reduce costs and increase throughput. The ability to multiplex analytes through the use of unique signatures based spatial and spectral signatures, coded to that analyte can also be used to multiplex samples.

Figure 21:
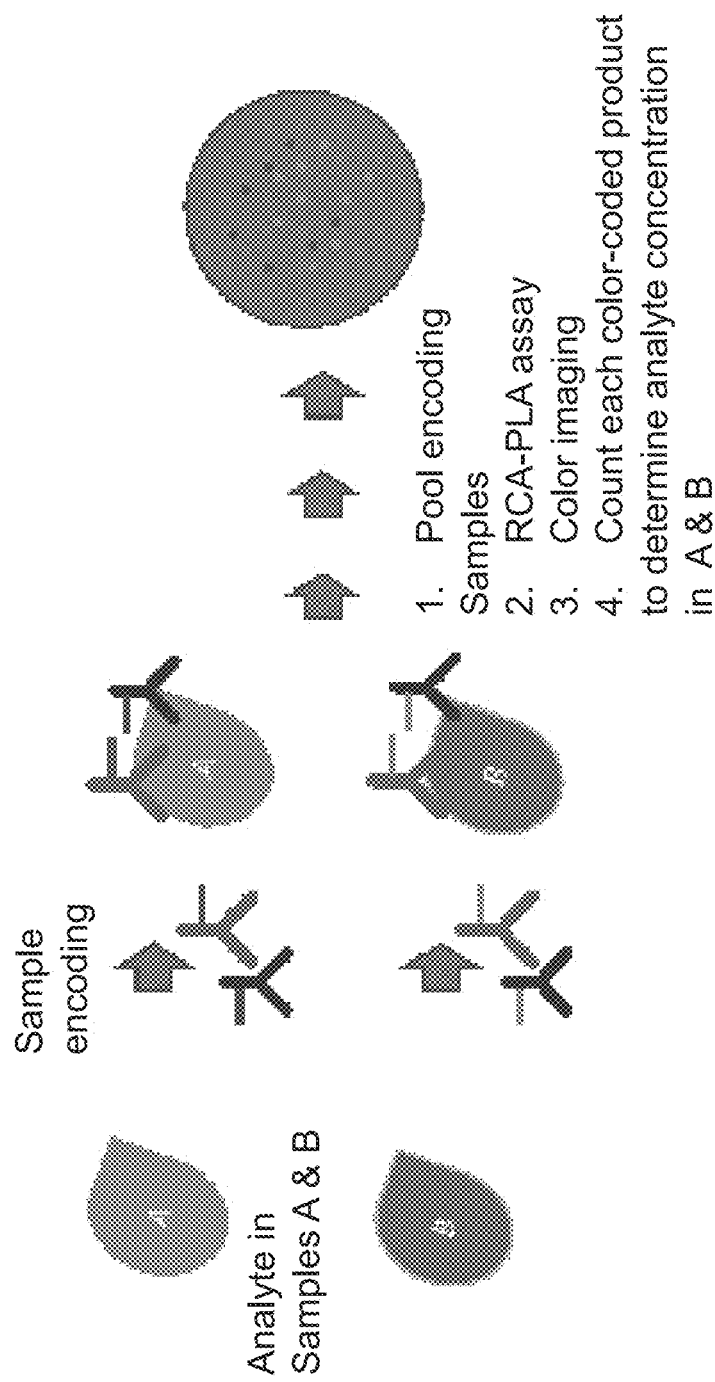
FIG. 21 is a schematic representation of sample multiplexing.

Samples are multiplexed using a fluorescent dye ratio coding of imaged amplified products. For each analyte in a sample, a set of unique assay reagents able to produce unique rolling circle products are employed, each detectable with a unique detection oligonucleotide. The synthesis and use of a set of unique assay reagents can be done according to the procedure described, e.g., in Example 1. As illustrated in FIG. 21, each sample, A and B, containing analyte of interest is incubated with the two detection antibodies specific for that analyte, each bearing a unique proximity probe. This incubation step links a set of unique proximity probes with the analyte in that sample, thereby forming a two antibody complex with the analyte and "encoding" the samples. Following this incubation, the encoding samples are pooled, added as a mixture to a single capture antibody surface, incubated and washed.

Following the wash step, the captured three antibody complexes, the linear rolling circle templates for each set of proximity probes are added, and the mixture is subjected to hybridization conditions as described in Example 1. This mixture is ligated to generate the rolling circle template, washed, subjected to rolling circle amplification, and washed. Each rolling circle amplicon is hybridized to a complementary and unique detection oligonucleotide, encoded with a unique spectral signature based on the ratio(s) of 2 or more fluorescent labels. Following the hybridization of the detection probes, the assay surface is imaged and each rolling circle product is decoded based on its spectral signature, e.g., the ratio(s) of the 2 or more fluorescent labels, and counted. This allows for the determination of analyte levels in multiple samples. Using this approach, a user can combine sample and analyte multiplexing, allowing multiple analytes to be tested in test and control samples simultaneously.

Example 12. Detection of Lipoprotein Complexes

The methods described herein are used to detect and quantify sets of protein complexes present in lipoprotein complexes, e.g., HDL and LDL. For example, using the method described in Example 1, three differing proteins and/or epitopes are detected within a lipoprotein complex, and therefore, a profile of the proteins within a patient's lipoproteins can be analyzed.

In humans blood lipoproteins are classified into 5-major groups, HDL, LDL, IDL, VLDL and chylomicrons. Of these, the HDL and LDL fractions have received the most clinical interest, as risk markers of cardiovascular health. These key lipoproteins are composed of complexes of multiple proteins and lipids. The proteins associated with these lipoproteins consist of proteins integral to their function and passenger proteins. These lipoproteins may also be subjected to modifications, such as oxidation, that modify the risk profile of an individual. For example, higher levels of oxidized HDL and LDL are associated with an increased risk of adverse cardiovascular events. LDL is typically composed of two core proteins Apo(a) and ApoB, and lipids. Elevated Apo(a) is associated with increased risk of heart disease; in addition, variations in the length of the Apo(a) protein are also associated with altered risk profiles. Apo(a) proteins vary in size due to a size polymorphism, which is caused by a variable number of so-called kringle repeats in the LPA gene. ApoB in the LDL particle carries the ligand for the LDL receptors in various tissues. High levels of ApoB are also associated with plaque formation, leading to cardiovascular disease. HDL is typically composed of a set of core proteins including; ApoA1, ApoE, ApoC and ApoA-II. In addition to these core proteins, HDL is also known to be associated with additional proteins that also have clinical value. For example, HDL associated SAA and SP-B have been demonstrated to be associated with cardiac events and mortality. Variations in HDL composition, through elevated ApoA-II, have also been linked to atherogenic risk.

Figure 22:
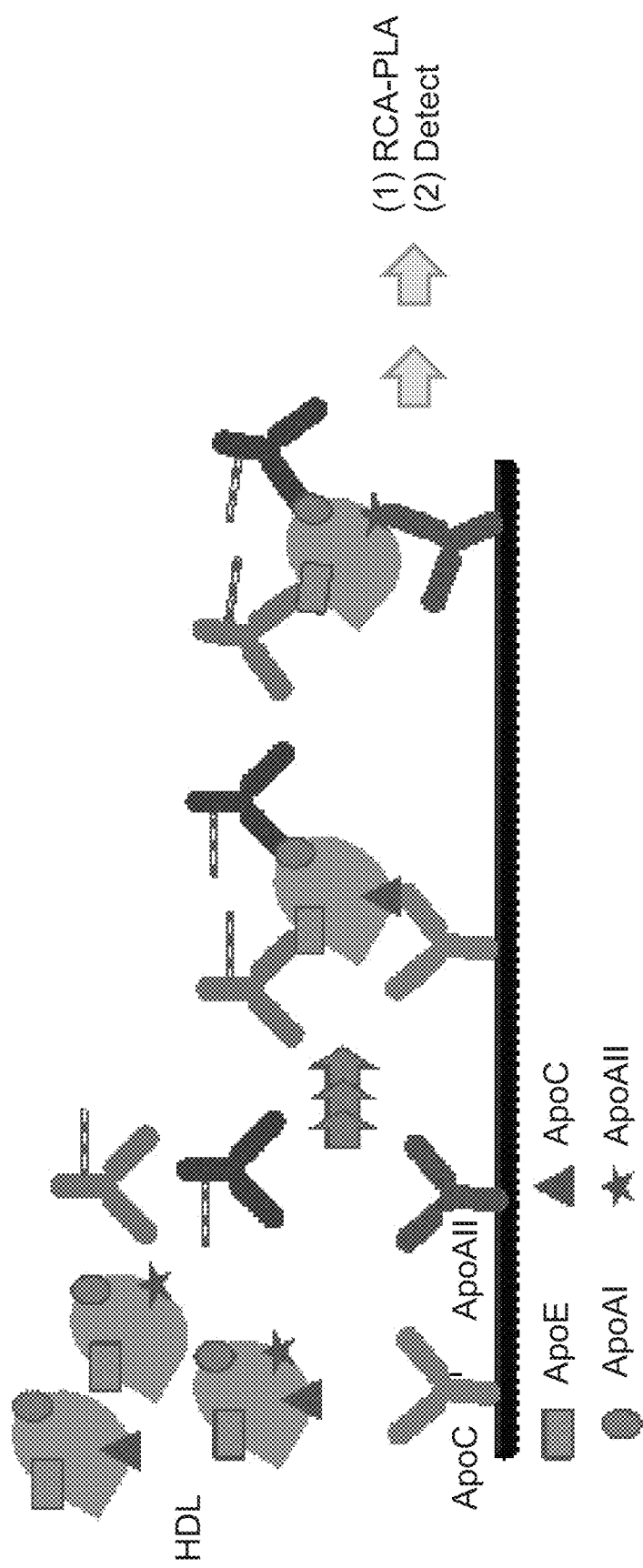
FIG. 22 is a schematic representation of the detection of lipoprotein complexes using the methods described herein.

Following the procedure described in Example 1, a multiplexed proximity assay for lipoprotein complexes is conducted as outlined in FIG. 22. FIG. 22 illustrates the detection of HDL lipoprotein complexes, wherein capture antibodies specific for each of the core proteins are immobilized to a surface to bind the lipoprotein complex to the surface. Detection antibodies specific for the additional core proteins are added, each bearing a proximity probe. The assay is completed as described in Example 1.

The present invention is not to be limited in scope by the specific embodiments described herein. Indeed, various modifications of the method in addition to those described herein will become apparent to those skilled in the art from the foregoing description and accompanying figures. Such modifications are intended to fall within the scope of the claims. Various publications are cited herein, the disclosures of which are incorporated by reference in their entireties.

REFERENCES

1. U.S. Pat. No. 7,306,904
2. U.S. Pat. No. 7,320,860
3. U.S. Pat. No. 7,351,528
4. U.S. Pat. No. 7,192,703
5. U.S. Pat. No. 6,878,515
6. Zhou et al., Genome Biology (2004), 5: R28
7. Dean et al., Genome Research (2001), 11: 1095-1099
8. Soderberg et al., Methods (2008), 45: 227-232
9. Fredriksson et al., Nature Biotech (2002), 20: 473-477
10. Fredriksson et al., Nature Methods (2007), 4(4): 327-329
11. Vincent et al., EMBO Reports (2005), 5(8): 795-800
12. Gajadjar et al., Biotechniques (1010), 48(22): 145-152
13. Schallmeiner et al, Nature Methods (2007) 4(2): 135-137
14. Ericsson et al., Nucl. Acids Research (2008), 36(8): e45
15. Darmanis et al., Biotechniques (2007), 43: 443-450
16. Dahl et al., Proc. Natl. Acad. Sci. (2004), 101(13): 4548-4553
17. Weibrecht et al., Expert Rev. Proteomics (2010), 7(3): 401-409
18. Spits et al., Nature Protocols (2005), 1(4): 1965-1970
19. Nordengrahn et al., Vet. Microbio (2008), 127: 227-236
20. Vuoriluoto et al., Mol. Oncology (2011), 5: 105-111
21. Zhang et al., Clinica Chimica Acta (2006), 363: 61-70
22. Andras et al., Mol. Biotech. (2001), 19: 29-44
23. Schweltzer et al., Proc. Natl. Acad. Sci. (2000), 97(18): 10113-10119
24. Jeong, et al., Cell. Mol. Life Sci. (2009), 66: 3325-3336
25. Gill et al., Nucleosides, Nucleotides, and Nucleic Acids (2008), 27: 224-245
26. Gullberg, et al., Current Op. in Biotech. (2003), 14: 82-86
27. Gustafsdottir, et al., Clinical Chemistry (2006), 52(6): 1152-1160
28. U.S. Patent Publication No. 20100075862
29. U.S. Pat. No. 8,222,047
30. U.S. Pat. No. 8,236,574
31. U.S. Pat. No. 8,338,776
32. U.S. Patent Publication No. 20110212537
33. U.S. Patent Publication No. 20120196774
34. U.S. Patent Publication No. 20120289428
35. Kopecky, C., et al., Clin. J. Am. Soc. Nephrol. 2014 Nov. 25
36. Watanabe, J., et al., Arthritis Rheum. 2012 June; 64(6): 1828-37
37. Ribas, V., et al., Circ. Res. 2004 Oct. 15: 95(8): 789-97

The invention claimed is:

1. A kit for detecting an analyte of interest in a sample comprising, in one or more vials, containers, or compartments:
   a) a surface comprising (i) a capture reagent for the analyte, and (ii) an anchoring reagent comprising an anchoring oligonucleotide, wherein the capture reagent and the anchoring reagent are immobilized on the surface;
   b) a detection reagent for the analyte that is linked to a nucleic acid probe, wherein the nucleic acid probe is capable of being extended to form an extended sequence comprising an anchoring oligonucleotide complement, wherein the anchoring oligonucleotide complement is complementary to the anchoring oligonucleotide; and
   c) a template oligonucleotide that is capable of hybridizing to the nucleic acid probe and that comprises a first region comprising a same sequence as the anchoring oligonucleotide.

2. The kit of claim 1, wherein the surface comprises a particle.

3. The kit of claim 1, wherein the surface comprises a well of a multi-well plate.

4. The kit of claim 3, wherein the well comprises a plurality of distinct binding domains and the capture reagent and the anchoring reagent are located on two distinct binding domains within the well.

5. The kit of claim 3, wherein the well comprises a plurality of distinct binding domains and the capture reagent and the anchoring reagent are located on the same binding domain within the well.

6. The kit of claim 1, wherein the surface comprises a plurality of distinct binding domains and the capture reagent and the anchoring reagent are located on two distinct binding domains on the surface.

7. The kit of claim 1, wherein the surface comprises a plurality of distinct binding domains and the capture reagent and the anchoring reagent are located on the same binding domain on the surface.

8. The kit of claim 1, wherein the surface comprises an electrode.

9. The kit of claim 1, wherein the capture reagent is selected from a group consisting of an antibody, an antigen, a ligand, a receptor, an oligonucleotide, a hapten, an epitope, a mimotope, and an aptamer.

10. The kit of claim 1, wherein the detection reagent is selected from the group consisting of an antibody, an antigen, a ligand, a receptor, an oligonucleotide, a hapten, an epitope, a mimotope, and an aptamer.

11. The kit of claim 1, wherein the capture reagent and the detection reagent are both antibodies to the analyte.

12. The kit of claim 1, further comprising a buffer, a polymerase, a ligase, a labeled or unlabeled dNTP, a detectable label, a co-reactant for a detectable label, a blocking agent, a stabilizing agent, a detergent, a salt, a pH buffer, a preservative, a labeled probe, an assay diluent, a calibrator, or a combination thereof.

13. The kit of claim 1, wherein the analyte of interest comprises an exosome.

14. The kit of claim 13, wherein the detection reagent is a first detection reagent linked to a first nucleic acid probe, and wherein the kit further comprises a second detection reagent linked to a second nucleic acid probe.

15. The kit of claim 14, wherein the capture reagent, the first detection reagent, and the second detection reagent are antibodies to a target molecule in or on a surface of the exosome.

16. The kit of claim 15, wherein the capture reagent is capable of binding to a common exosome target protein selected from one or more of CD9, CD63, CD81, Hsp70, PDCD6IP, and Tsg101.

17. The kit of claim 15, wherein at least one of the first detection reagent and the second detection reagent is an antibody to a disease-specific target molecule in or on the surface of the exosome.

18. The kit of claim 15, wherein the first detection reagent and the second detection reagent each binds to one of a pair of interacting exosome target molecules.

19. The kit of claim 18, wherein the pair of interacting exosome target molecules comprise a ligand-receptor pair, an mRNA and an RNA-binding protein, or both.

20. The kit of claim 1, wherein the template oligonucleotide further comprises a second region comprising a detection oligonucleotide complement, wherein the extended sequence further comprises a detection oligonucleotide, and wherein the kit further comprises a labeled probe that comprises (i) a same sequence as the detection oligonucleotide complement and that is capable of binding to the detection oligonucleotide; and (ii) a detectable label.

21. A kit for detecting an analyte of interest in a sample comprising, in one or more vials, containers, or compartments:
   a) a capture reagent for the analyte, wherein the capture reagent is capable of being immobilized to a surface,
   b) an anchoring reagent comprising an anchoring oligonucleotide, wherein the anchoring reagent is capable of being immobilized to a surface;
   c) a detection reagent for the analyte that is linked to a nucleic acid probe, wherein the nucleic acid probe is capable of being extended to form an extended sequence comprising an anchoring oligonucleotide complement, wherein the anchoring oligonucleotide complement is complementary to the anchoring oligonucleotide; and
   d) a template oligonucleotide that is capable of hybridizing to the nucleic acid probe and that comprises a first region comprising a same sequence as the anchoring oligonucleotide.

22. The kit of claim 21, further comprising the surface to which the capture reagent and the anchoring reagent are capable of being immobilized.

23. The kit of claim 22, wherein the surface comprises a particle.

24. The kit of claim 22, wherein the surface comprises a well of a multi-well plate.

25. The kit of claim 24, wherein the well comprises a plurality of distinct binding domains, and the capture reagent and the anchoring reagent are located on two distinct binding domains on the well.

26. The kit of claim 24, wherein the well comprises a plurality of distinct binding domains, and the capture reagent and the anchoring reagent are located on the same binding domain on the well.

27. The kit of claim 22, wherein the surface comprises a plurality of distinct binding domains, and the capture reagent and the anchoring reagent are located on two distinct binding domains on the surface.

28. The kit of claim 22, wherein the surface comprises a plurality of distinct binding domains, and the capture reagent and the anchoring reagent are located on the same binding domain on the surface.

29. The kit of claim 22, wherein the surface comprises an electrode.

30. The kit of claim 22, wherein each of the capture reagent and the detection reagent is independently selected from a group consisting of an antibody, an antigen, a ligand, a receptor, an oligonucleotide, a hapten, an epitope, a mimotope, and an aptamer.

31. The kit of claim 21, wherein each of the capture reagent and the detection reagent is an antibody to the analyte.

32. The kit of claim 21, further comprising a buffer, a polymerase, a ligase, a labeled or unlabeled dNTP, a detectable label, a co-reactant for a detectable label, a blocking agent, a stabilizing agent, a detergent, a salt, a pH buffer, a preservative, a labeled probe, an assay diluent, a calibrator, or a combination thereof.

33. The kit of claim 21, wherein the analyte of interest comprises an exosome.

34. The kit of claim 33, wherein the detection reagent is a first detection reagent linked to a first nucleic acid probe, and wherein the kit further comprises a second detection reagent linked to a second nucleic acid probe.

35. The kit of claim 34, wherein the capture reagent, the first detection reagent, and the second detection reagent are antibodies to a target molecule in or on a surface of the exosome.

36. The kit of claim 35, wherein the capture reagent is capable of binding to a common exosome target protein selected from one or more of CD9, CD63, CD81, Hsp70, PDCD6IP, and Tsg101.

37. The kit of claim 35, wherein at least one of the first detection reagent and the second detection reagent is an antibody to a disease-specific target molecule in or on the surface of the exosome.

38. The kit of claim 35, wherein the first detection reagent and the second detection reagent each binds to one of a pair of interacting exosome target molecules.

39. The kit of claim 38, wherein the pair of interacting exosome target molecules comprise a ligand-receptor pair, an mRNA and an RNA-binding protein, or both.

40. The kit of claim 21, wherein the template oligonucleotide further comprises a second region comprising a detection oligonucleotide complement, wherein the extended sequence further comprises a detection oligonucleotide, and wherein the kit further comprises a labeled probe that comprises (i) a same sequence as the detection oligonucleotide complement and that is capable of binding to the detection oligonucleotide; and (ii) a detectable label.

* * * * *